(12) United States Patent
Davicioni et al.

(10) Patent No.: US 9,994,907 B2
(45) Date of Patent: Jun. 12, 2018

(54) THYROID CANCER DIAGNOSTICS

(71) Applicant: GENOMEDX BIOSCIENCES, INC., Vancouver (CA)

(72) Inventors: Elai Davicioni, La Jolla, CA (US); Zaid Haddad, Burnaby (CA)

(73) Assignee: GenomeDx Biosciences, Inc., Vancouver (CA)

( * ) Notice: Subject to any disclaimer, the term of this patent is extended or adjusted under 35 U.S.C. 154(b) by 419 days.

(21) Appl. No.: 14/020,183

(22) Filed: Sep. 6, 2013

(65) Prior Publication Data

US 2014/0080731 A1 Mar. 20, 2014

Related U.S. Application Data

(60) Provisional application No. 61/703,553, filed on Sep. 20, 2012.

(51) Int. Cl.
*C12Q 1/68* (2018.01)
(52) U.S. Cl.
CPC ..... *C12Q 1/6886* (2013.01); *C12Q 2600/158* (2013.01); *C12Q 2600/178* (2013.01)
(58) Field of Classification Search
None
See application file for complete search history.

(56) References Cited

U.S. PATENT DOCUMENTS

2012/0115743 A1 5/2012 Davicioni et al.

FOREIGN PATENT DOCUMENTS

| EP | 2366800 A1 | 9/2011 |
| WO | WO 2010/056374 A2 | 5/2010 |
| WO | WO 2010/124372 A1 | 11/2010 |

OTHER PUBLICATIONS

Griffith, O. et al.: *Meta-analysis and meta-review of thyroid cancer gene expression profiling studies identifies important diagnostic biomarkers*; Journal of Clinical Oncology. Nov. 1, 2006, vol. 24, No. 31, pp. 5043-5051, ISSN 0732-183X.
International Search Report Regarding PCT/CA2013/050686.
Yukinawa, Naoto et al.: "*A multi-class predictor based on a probabilistic model: application to gene expression profiling-based diagnosis of thyroid tumors*"; BMC Genomics, vol. 7, No. 1, Jul. 27, 2006, 13 pgs.
Extended European Search Report dated Apr. 22, 2016, regarding EP 13838743.6.

*Primary Examiner* — Nancy A Treptow
(74) *Attorney, Agent, or Firm* — DLA Piper LLP (US)

(57) ABSTRACT

Disclosed herein, in certain instances, are methods for the diagnosis, prognosis and determination of cancer progression of a cancer in a subject. Further disclosed herein, in certain instances, are methods for determining the treatment modality of a cancer in a subject. The methods comprise expression-based analysis of targets. Further disclosed herein, in certain instances, are probe sets for use in assessing a cancer status in a subject.

11 Claims, 8 Drawing Sheets

Figure 1A. Unsupervised Analysis - Training Path Review Dx
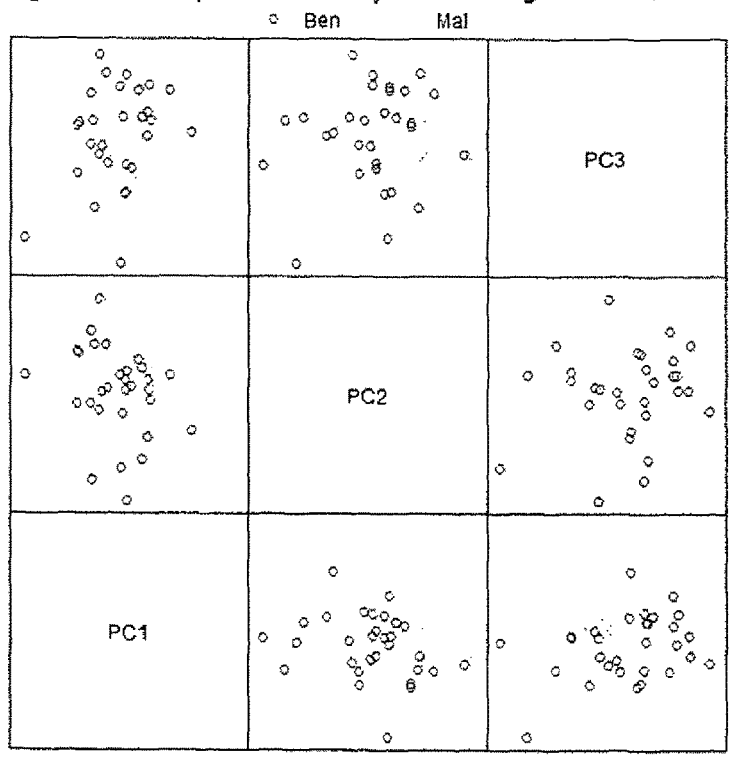
Figure 1B. Unsupervised Analysis - Training FNA Dx
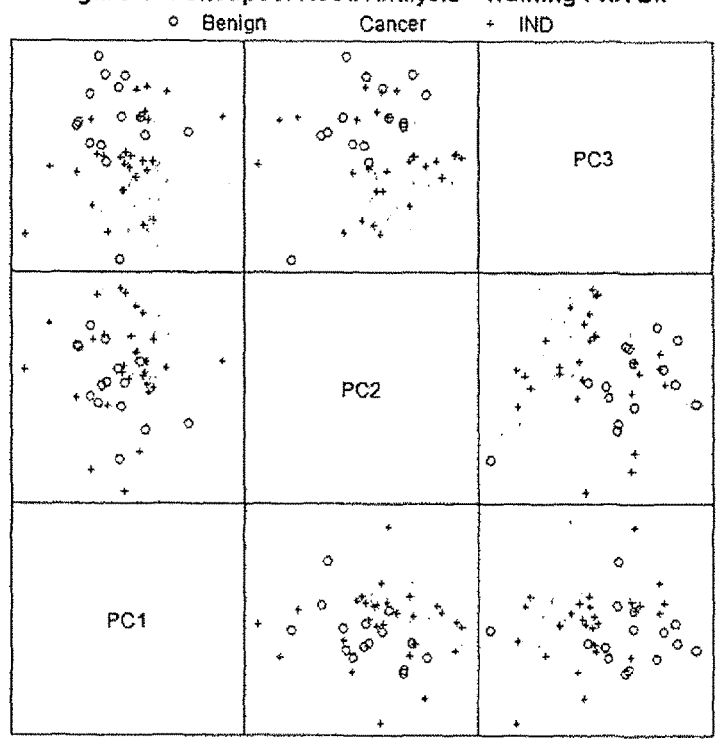

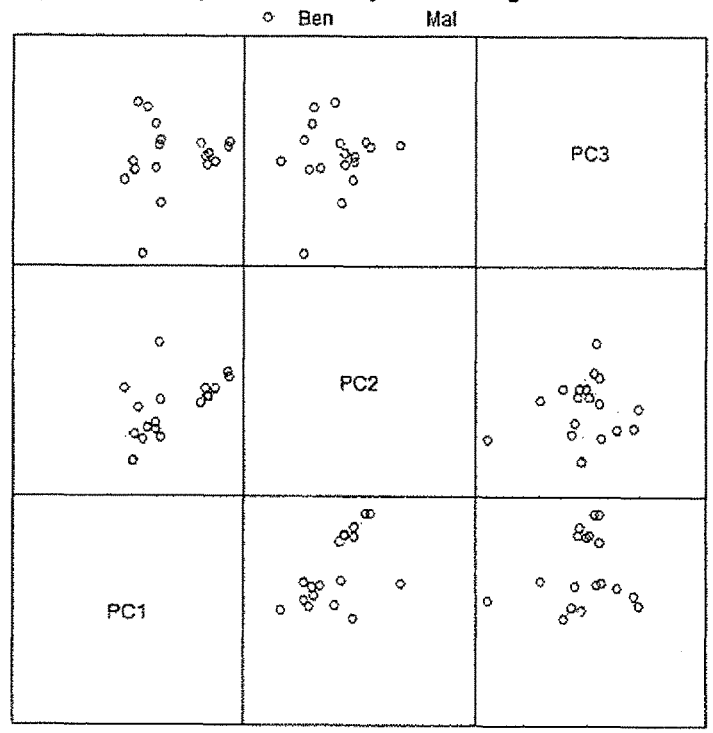
Figure 1C. Unsupervised Analysis - Testing Path Review Dx
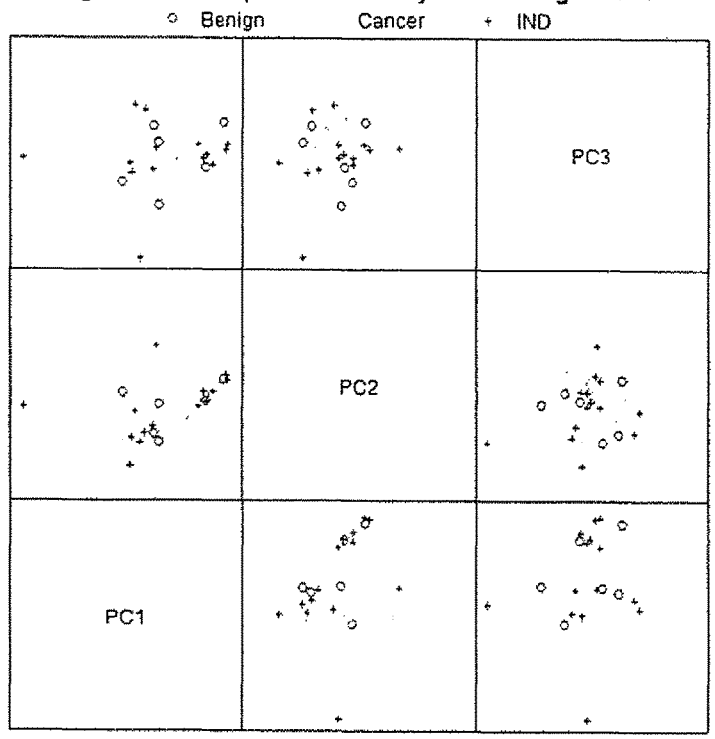
Figure 1D. Unsupervised Analysis - Testing FNA Dx

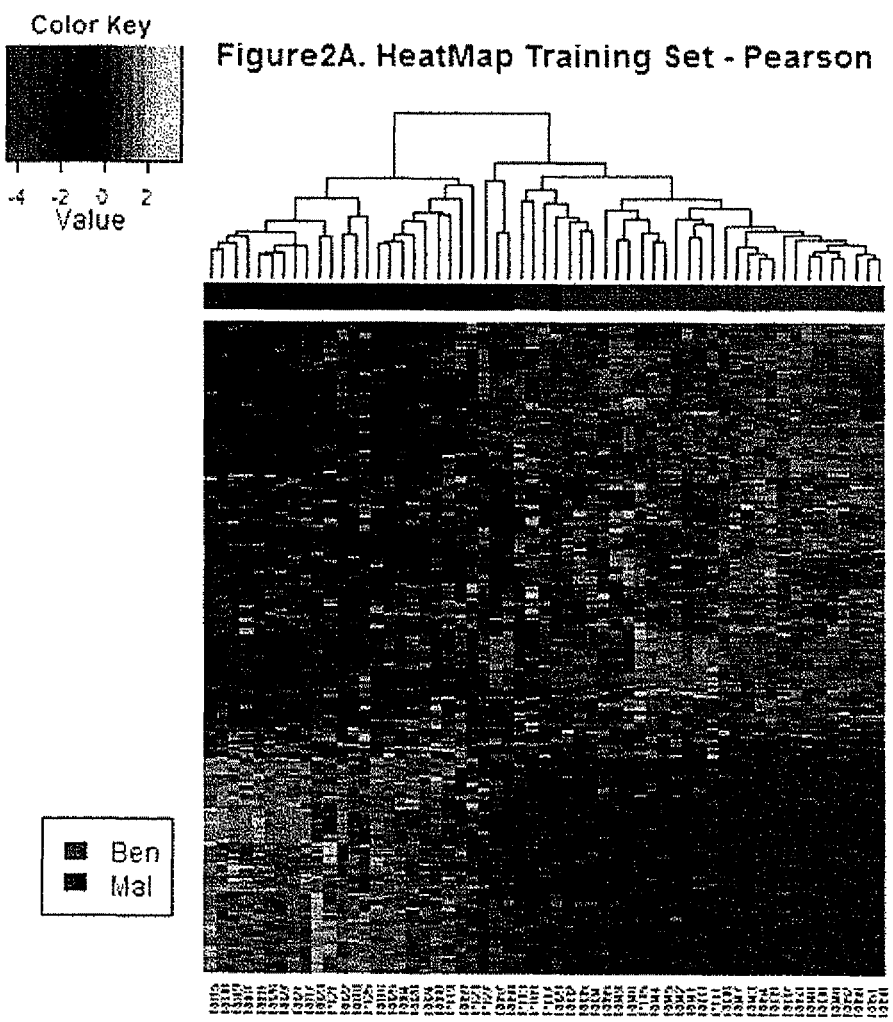

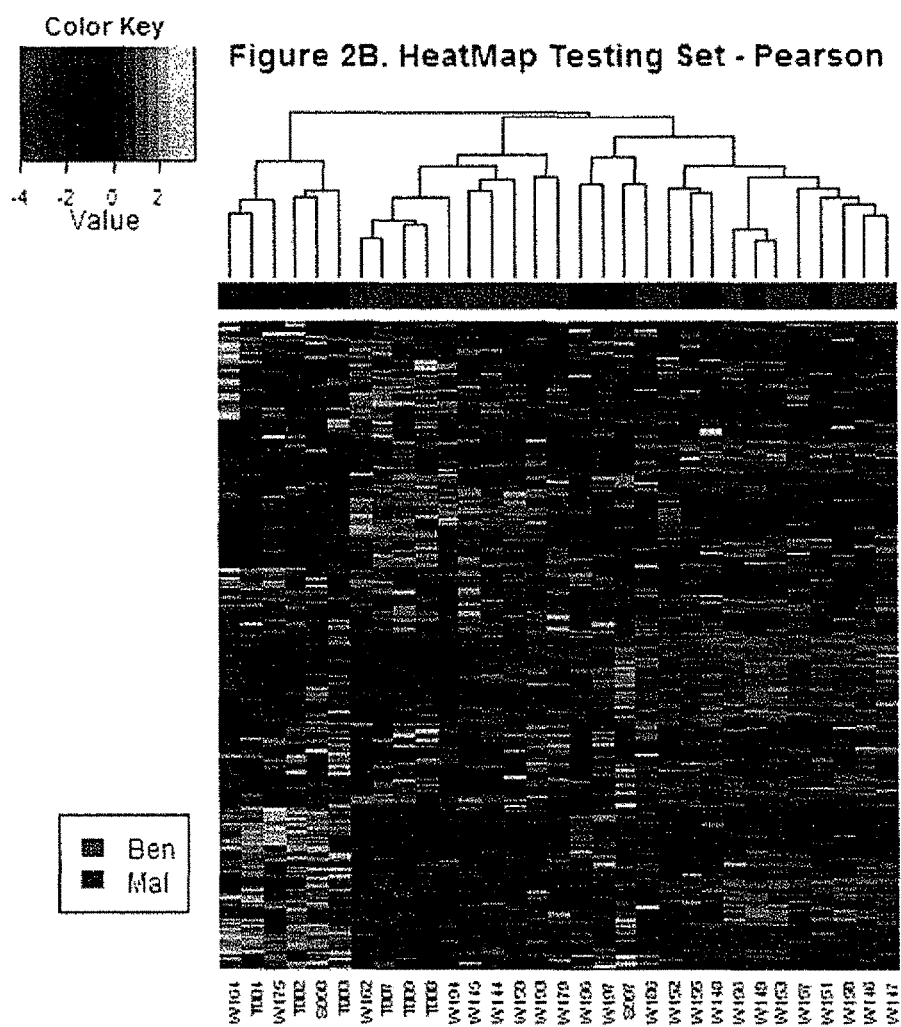

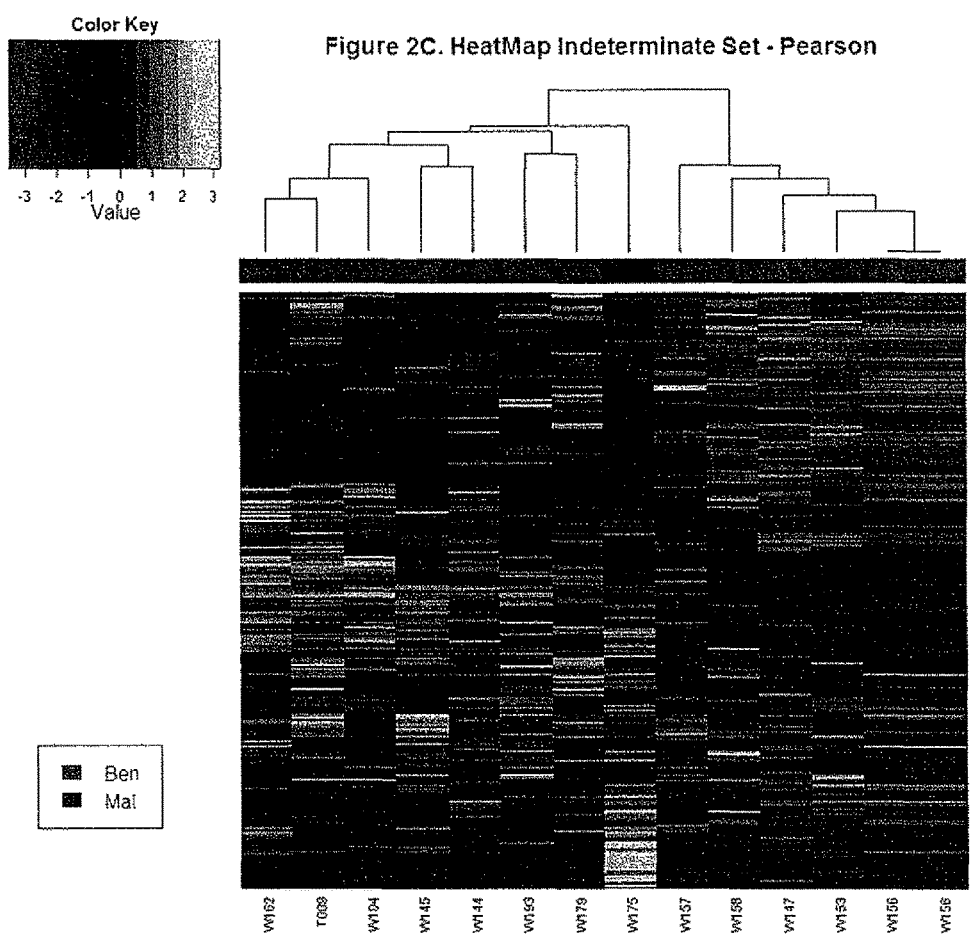

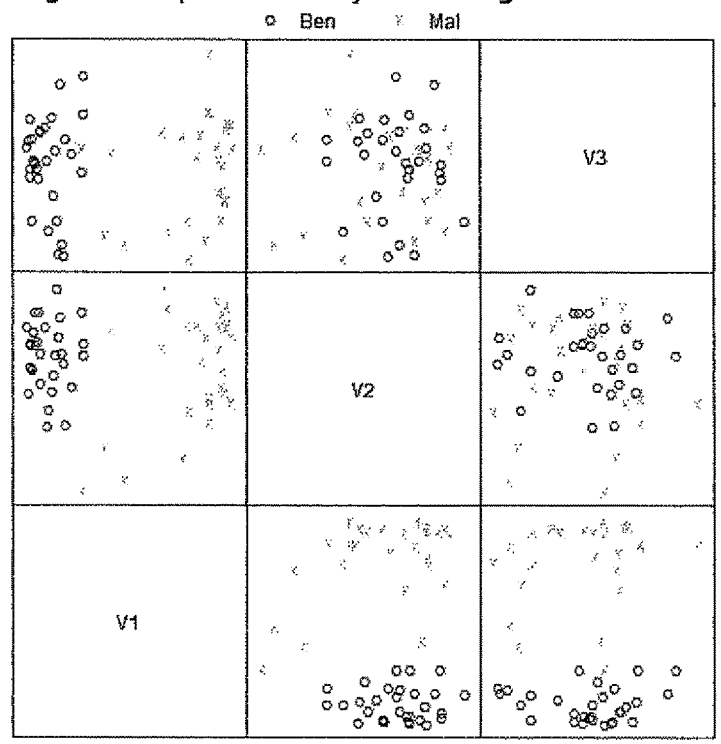
Figure 3A. Supservised Analysis - Training Path Review Dx
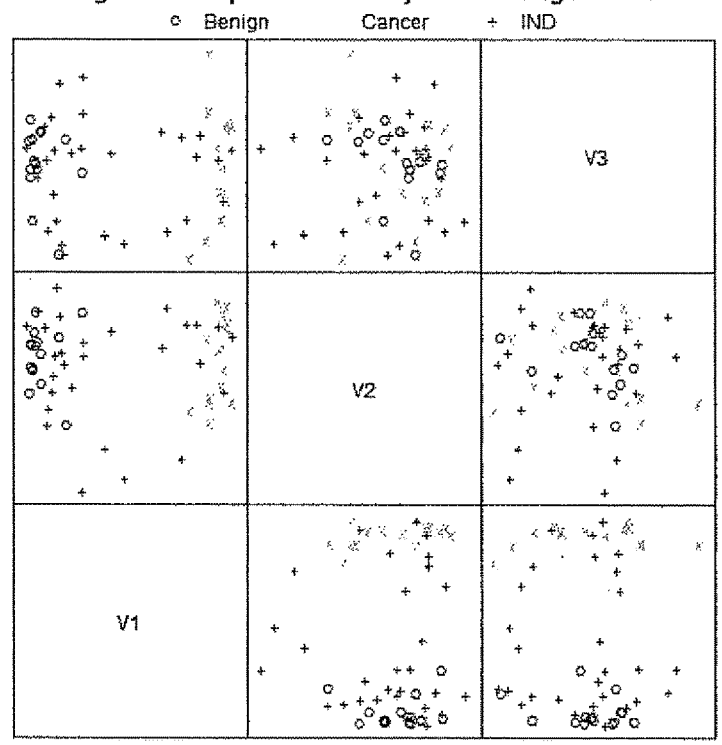
Figure 3B. Supservised Analysis - Training FNA Dx

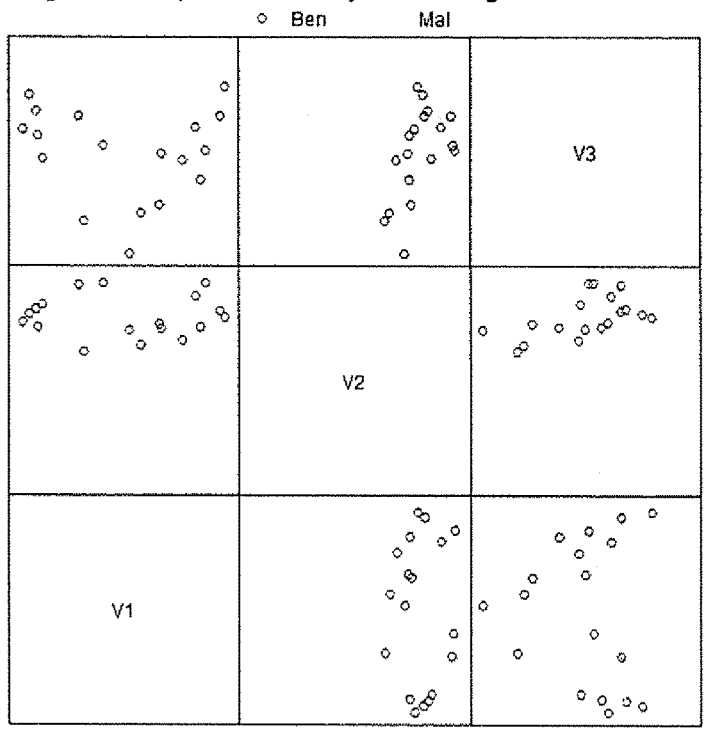
Figure 3C. Supservised Analysis - Testing Path Review Dx
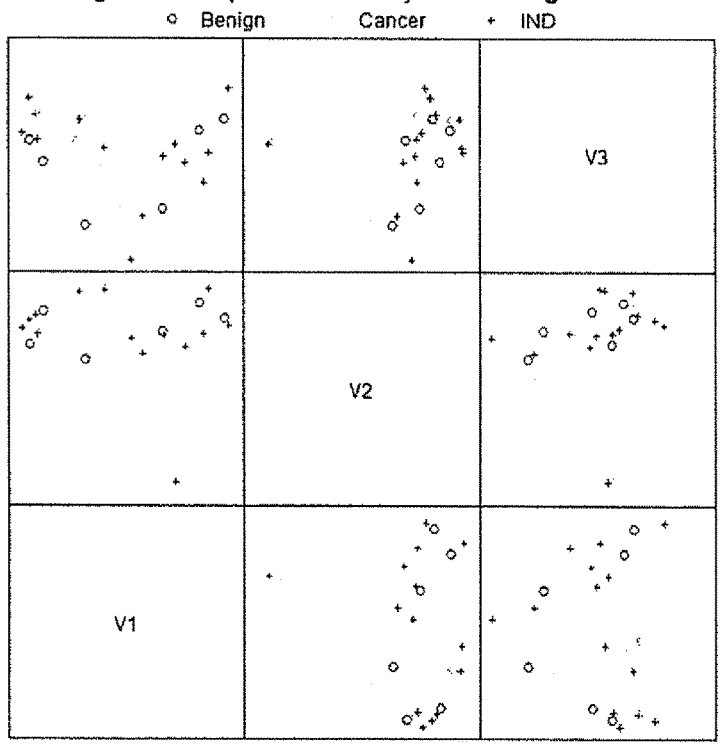
Figure 3D. Supservised Analysis - Testing FNA Dx

THYROID CANCER DIAGNOSTICS

CROSS REFERENCE TO RELATED APPLICATION(S)

This application is a Utility application which claims the benefit of priority under 35 U.S.C. § 119(e) of U.S. Ser. No. 61/703,553 filed Sep. 20, 2012. The disclosure the prior application is considered part of, and is incorporated by reference in, the disclosure of this application.

BACKGROUND OF THE INVENTION

Cancer is the uncontrolled growth of abnormal cells anywhere in a body. The abnormal cells are termed cancer cells, malignant cells, or tumor cells. Many cancers and the abnormal cells that compose the cancer tissue are further identified by the name of the tissue that the abnormal cells originated from (for example, breast cancer, lung cancer, colon cancer, prostate cancer, pancreatic cancer, thyroid cancer). Cancer is not confined to humans; animals and other living organisms can get cancer. Cancer cells can proliferate uncontrollably and form a mass of cancer cells. Cancer cells can break away from this original mass of cells, travel through the blood and lymph systems, and lodge in other organs where they can again repeat the uncontrolled growth cycle. This process of cancer cells leaving an area and growing in another body area is often termed metastatic spread or metastatic disease. For example, if breast cancer cells spread to a bone (or anywhere else), it can mean that the individual has metastatic breast cancer.

Standard clinical parameters such as tumor size, grade, lymph node involvement and tumor-node-metastasis (TNM) staging (American Joint Committee on Cancer at the world wide web at cancerstaging.org) may correlate with outcome and serve to stratify patients with respect to (neo)adjuvant chemotherapy, immunotherapy, antibody therapy and/or radiotherapy regimens. Incorporation of molecular markers in clinical practice may define tumor subtypes that are more likely to respond to targeted therapy. However, stage-matched tumors grouped by histological or molecular subtypes may respond differently to the same treatment regimen. Additional key genetic and epigenetic alterations may exist with important etiological contributions. A more detailed understanding of the molecular mechanisms and regulatory pathways at work in cancer cells and the tumor microenvironment (TME) could dramatically improve the design of novel anti-tumor drugs and inform the selection of optimal therapeutic strategies. The development and implementation of diagnostic, prognostic and therapeutic biomarkers to characterize the biology of each tumor may assist clinicians in making important decisions with regard to individual patient care and treatment. Thus, disclosed herein are methods, compositions and systems for the analysis of targets for the diagnosis, prognosis, monitoring, and treatment of a cancer.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

Disclosed herein are compositions, systems, and methods for diagnosing, predicting, and/or monitoring the status or outcome of a cancer in a subject. Disclosed herein, in some embodiments, is a method comprising (a) assaying an expression level in a sample from the subject for a plurality of targets, wherein the plurality of targets comprises one or more targets selected from (i) a target listed in Table 6; (ii) a target comprising a sequence selected from SEQ ID NOs: 1-153; (iii) a target comprising a sequence that is a complement of a sequence selected from SEQ ID NOs: 1-153; (iv) a target comprising a sequence that is a reverse complement of a sequence selected from SEQ ID NOs: 1-153; or (v) a combination of (i-iv); and diagnosing, prognosing, determining progression the cancer, or predicting benefit from therapy in a subject based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a thyroid cancer. In some embodiments, the plurality of targets comprises a nucleic acid sequence. In some embodiments, the nucleic acid sequence is a DNA sequence. In some embodiments, the nucleic acid sequence is an RNA sequence. In some instances, the plurality of targets comprises a non-coding RNA transcript. In some instances, the non-coding RNA transcript is non-polyadenylated. In some instances, the plurality of targets comprises a polyadenylated target. In some embodiments, the plurality of targets comprises an intronic sequence, a sequence within the UTR, non-coding RNA transcript, or a portion thereof. In some embodiments, the plurality of targets comprises an intronic sequence or a portion of an intronic sequence. In some embodiments, the plurality of targets comprises a UTR sequence or a portion of a UTR sequence. In some embodiments, the plurality of targets comprises non-coding RNA transcript. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the plurality of targets comprises an exon-coding transcript or a portion of an exon-coding transcript. In some embodiments, the exon-coding transcript is an exonic sequence. In some embodiments, the plurality of targets comprises two or more targets. In some embodiments, the plurality of targets comprises three or more targets. In some embodiments, the plurality of targets comprises five or more targets. In some embodiments, the plurality of targets comprises ten or more targets. In some embodiments, the plurality of targets comprises twenty or more targets. In some embodiments, the plurality of targets comprises thirty or more targets. In some embodiments, the plurality of targets comprises forty or more targets. In some embodiments, the plurality of targets comprises fifty or more targets. In some embodiments, the plurality of targets comprises sixty or more targets. In some embodiments, the plurality of targets comprises two or more targets selected from a target listed in Table 6. In some embodiments, the plurality of targets comprises three or more targets selected from a target listed in Table 6. In some embodiments, the plurality of targets comprises five or more targets selected from a target listed in Table 6. In some embodiments, the plurality of targets comprises ten or more targets selected from a target listed in Table 6. In some embodiments, the plurality of targets comprises twenty or more targets selected from a target listed in Table 6. In some embodiments, the plurality of targets comprises thirty or more targets selected from a target listed in Table 6. In some embodiments, the plurality of targets comprises two or more targets comprising a sequence selected from SEQ ID NOs: 1-153. In some embodiments, the plurality of targets comprises three or more targets comprising a sequence selected from SEQ ID NOs: 1-153. In some embodiments, the plurality of targets comprises five or more targets comprising a sequence selected from SEQ ID NOs: 1-153. In some embodiments, the plurality of targets comprises ten or more targets comprising a sequence selected from SEQ ID NOs: 1-153. In some embodiments, the plurality of targets comprises twenty or more targets comprising a sequence selected from SEQ ID NOs: 1-153. In some embodiments, the plurality of targets comprises thirty or more targets comprising a sequence selected from SEQ ID NOs: 1-153. In some embodiments, the plurality of targets comprises two or more targets comprising a sequence that is a complement of a sequence selected from SEQ ID NOs: 1-153. In some embodiments, the plurality of targets comprises three or more targets comprising a sequence that is a complement of a sequence selected from SEQ ID NOs: 1-153. In some embodiments, the plurality of targets comprises five or more targets comprising a sequence that is a complement of a sequence selected from SEQ ID NOs: 1-153. In some embodiments, the plurality of targets comprises ten or more targets comprising a sequence that is a complement of a sequence selected from SEQ ID NOs: 1-153. In some embodiments, the plurality of targets comprises twenty or more targets comprising a sequence that is a complement of a sequence selected from SEQ ID NOs: 1-153. In some embodiments, the plurality of targets comprises thirty or more targets comprising a sequence that is a complement of a sequence selected from SEQ ID NOs: 1-153. In some embodiments, the plurality of targets comprises two or more targets comprising a sequence that is a reverse complement of a sequence selected from SEQ ID NOs: 1-153. In some embodiments, the plurality of targets comprises three or more targets comprising a sequence that is a reverse complement of a sequence selected from SEQ ID NOs: 1-153. In some embodiments, the plurality of targets comprises five or more targets comprising a sequence that is a reverse complement of a sequence selected from SEQ ID NOs: 1-153. In some embodiments, the plurality of targets comprises ten or more targets comprising a sequence that is a complement of a sequence selected from SEQ ID NOs: 1-153. In some embodiments, the plurality of targets comprises twenty or more targets comprising a sequence that is a reverse complement of a sequence selected from SEQ ID NOs: 1-153. In some embodiments, the plurality of targets comprises thirty or more targets comprising a sequence that is a reverse complement of a sequence selected from SEQ ID NOs: 1-153. In some instances, the plurality of targets comprises at least ten consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least twenty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least thirty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least forty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least fifty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least sixty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least seventy consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least 80, 90, 100, 120, 140, 160, 180, 200, 250, 300, 350, 400, 450, or 500 consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least 600, 700, 800, 900, 1000, 1100, 1200, 1300, or 1400 consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some embodiments, the method further comprises assaying an expression level of a miRNA. In some embodiments, the method further comprises assaying an expression level of a siRNA. In some embodiments, the method further comprises assaying an expression level of a snoRNA. In some embodiments, the method further comprises assaying an expression level of a lincRNA. In some embodiments, the method further comprises amplifying the plurality of targets. In some embodiments, the method further comprises conducting a multiplexed reaction. In some embodiments, the method further comprises sequencing the plurality of targets. In some embodiments, the method further comprises quantifying the plurality of targets. In some embodiments, the method further comprises hybridizing a label to a plurality of targets. In some embodiments, the method does not comprise amplifying the plurality of targets. In some embodiments, the method comprises reverse transcribing the plurality of targets. In some embodiments, the method comprises hybridizing a probe to the plurality of targets. In some embodiments, the probe is labeled. In some embodiments, the plurality of targets is labeled. In some embodiments, the method further comprises attaching the plurality of targets to a solid support. In some embodiments, the method further comprises attaching a probe or probe set to a solid support. In some embodiments, the solid support is an array. In some embodiments, the solid support is a bead. In some embodiments, the solid support is a plate. In some embodiments, the solid support is a microwell plate. In some embodiments, diagnosing, prognosing, determining progression the cancer, or predicting benefit from therapy comprises determining the malignancy of the cancer. In some embodiments, diagnosing, prognosing, determining progression the cancer, or predicting benefit from therapy comprises determining the stage of the cancer. In some embodiments, diagnosing, prognosing, determining progression the cancer, or predicting benefit from therapy comprises assessing the risk of cancer recurrence. In some embodiments, diagnosing, prognosing, determining progression the cancer, or predicting benefit from therapy comprises determining the cancer status of the subject. In some instances, the expression level determines the cancer status of the subject with at least 50% specificity. In some instances, the expression level determines the cancer status of the subject with at least 60% specificity. In some instances, the expression level determines the cancer status of the subject with at least 65% specificity. In some instances, the expression level determines the cancer status of the subject with at least 70% specificity. In some instances, the expression level determines the cancer status of the subject with at least 75% specificity. In some instances, the expression level determines the cancer status of the subject with at least 80% specificity. In some instances, the expression level determines the cancer status of the subject with at least 85% specificity. In some instances, assaying the expression level of a plurality of targets comprises the use of a probe set. Alternatively, assaying the expression level comprises the use of a classifier. In some instances, the classifier comprises a probe selection region (PSR). Alternatively, the classifier comprises the use of an algorithm. In some instances, the algorithm comprises a machine learning algorithm. In some instances, assaying the expression level comprises sequencing the plurality of targets. In some instances, assaying the expression level comprises quantifying the plurality of targets.

Further disclosed herein, in some embodiments, is a method comprising: (a) assaying an expression level in a sample from the subject for a plurality of targets, wherein the plurality of targets comprises one or more targets selected from (i) a target listed in Table 6; (ii) a target comprising a sequence selected from SEQ ID NOs: 1-153; (iii) a target comprising a sequence that is a complement of a sequence selected from SEQ ID NOs: 1-153; (iv) a target comprising a sequence that is a reverse complement of a sequence selected from SEQ ID NOs: 1-153; or (v) a combination of (i-iv); and (b) determining the treatment for the cancer based on the expression level of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a thyroid cancer. In some embodiments, the plurality of targets comprises a nucleic acid sequence. In some embodiments, the nucleic acid sequence is a DNA sequence. In some embodiments, the nucleic acid sequence is an RNA sequence. In some instances, the plurality of targets comprises a non-coding RNA transcript. In some instances, the non-coding RNA transcript is non-polyadenylated. In some instances, the plurality of targets comprises a polyadenylated target. In some embodiments, the plurality of targets comprises an intronic sequence, a sequence within the UTR, non-coding RNA transcript, or a portion thereof. In some embodiments, the plurality of targets comprises an intronic sequence or a portion of an intronic sequence. In some embodiments, the plurality of targets comprises a UTR sequence or a portion of a UTR sequence. In some embodiments, the plurality of targets comprises non-coding RNA transcript. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the plurality of targets comprises an exon-coding transcript or a portion of an exon-coding transcript. In some embodiments, the exon-coding transcript is an exonic sequence. In some embodiments, the plurality of targets comprises two or more targets. In some embodiments, the plurality of targets comprises three or more targets. In some embodiments, the plurality of targets comprises five or more targets. In some embodiments, the plurality of targets comprises ten or more targets. In some embodiments, the plurality of targets comprises twenty or more targets. In some embodiments, the plurality of targets comprises thirty or more targets. In some embodiments, the plurality of targets comprises forty or more targets. In some embodiments, the plurality of targets comprises fifty or more targets. In some embodiments, the plurality of targets comprises sixty or more targets. In some embodiments, the plurality of targets comprises two or more targets selected from a target listed in Table 6. In some embodiments, the plurality of targets comprises three or more targets selected from a target listed in Table 6. In some embodiments, the plurality of targets comprises five or more targets selected from a target listed in Table 6. In some embodiments, the plurality of targets comprises ten or more targets selected from a target listed in Table 6. In some embodiments, the plurality of targets comprises twenty or more targets selected from a target listed in Table 6. In some embodiments, the plurality of targets comprises thirty or more targets selected from a target listed in Table 6. In some embodiments, the plurality of targets comprises two or more targets comprising a sequence selected from SEQ ID NOs: 1-153. In some embodiments, the plurality of targets comprises three or more targets comprising a sequence selected from SEQ ID NOs: 1-153. In some embodiments, the plurality of targets comprises five or more targets comprising a sequence selected from SEQ ID NOs: 1-153. In some embodiments, the plurality of targets comprises ten or more targets comprising a sequence selected from SEQ ID NOs: 1-153. In some embodiments, the plurality of targets comprises twenty or more targets comprising a sequence selected from SEQ ID NOs: 1-153. In some embodiments, the plurality of targets comprises thirty or more targets comprising a sequence selected from SEQ ID NOs: 1-151 In some embodiments, the plurality of targets comprises two or more targets comprising a sequence that is a complement of a sequence selected from SEQ ID NOs: 1-153. In some embodiments, the plurality of targets comprises three or more targets comprising a sequence that is a complement of a sequence selected from SEQ ID NOs: 1-153. In some embodiments, the plurality of targets comprises five or more targets comprising a sequence that is a complement of a sequence selected from SEQ ID NOs: 1-153. In some embodiments, the plurality of targets comprises ten or more targets comprising a sequence that is a complement of a sequence selected from SEQ ID NOs: 1-153. In some embodiments, the plurality of targets comprises twenty or more targets comprising a sequence that is a complement of a sequence selected from SEQ ID NOs: 1-153. In some embodiments, the plurality of targets comprises thirty or more targets comprising a sequence that is a complement of a sequence selected from SEQ ID NOs: 1-153. In some embodiments, the plurality of targets comprises two or more targets comprising a sequence that is a reverse complement of a sequence selected from SEQ ID NOs: 1-153. In some embodiments, the plurality of targets comprises three or more targets comprising a sequence that is a reverse complement of a sequence selected from SEQ ID NOs: 1-153. In some embodiments, the plurality of targets comprises five or more targets comprising a sequence that is a reverse complement of a sequence selected from SEQ ID NOs: 1-153. In some embodiments, the plurality of targets comprises ten or more targets comprising a sequence that is a complement of a sequence selected from SEQ ID NOs: 1-153. In some embodiments, the plurality of targets comprises twenty or more targets comprising a sequence that is a reverse complement of a sequence selected from SEQ ID NOs: 1-153. In some embodiments, the plurality of targets comprises thirty or more targets comprising a sequence that is a reverse complement of a sequence selected from SEQ ID NOs: 1-153. In some instances, the plurality of targets comprises at least ten consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least twenty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least thirty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least forty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least fifty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least sixty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least seventy consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least 80, 90, 100, 120, 140, 160, 180, 200, 250, 300, 350, 400, 450, or 500 consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least 600, 700, 800, 900, 1000, 1100, 1200, 1300, or 1400 consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some embodiments, the method further comprises assaying an expression level of a miRNA. In some embodiments, the method further comprises assaying an expression level of a siRNA. In some embodiments, the method further comprises assaying an expression level of a snoRNA. In some embodiments, the method further comprises assaying an expression level of a lincRNA. In some embodiments, the method further comprises amplifying the plurality of targets. In some embodiments, the method further comprises conducting a multiplexed reaction. In some embodiments, the method further comprises sequencing the plurality of targets. In some embodiments, the method further comprises quantifying the plurality of targets. In some embodiments, the method further comprises hybridizing a label to a plurality of targets. In some embodiments, the method does not comprise amplifying the plurality of targets. In some embodiments, the method comprises reverse transcribing the plurality of targets. In some embodiments, the method comprises hybridizing a probe to the plurality of targets. In some embodiments, the probe is labeled. In some embodiments, the plurality of targets is labeled. In some embodiments, the method further comprises attaching the plurality of targets to a solid support. In some embodiments, the method further comprises attaching a probe or probe set to a solid support. In some embodiments, the solid support is an array. In some embodiments, the solid support is a bead. In some embodiments, the solid support is a plate. In some embodiments, the solid support is a microwell plate. In some embodiments, determining the treatment for the cancer comprises determining the efficacy of treatment. In some instances, assaying the expression level of a plurality of targets comprises the use of a probe set. Alternatively, assaying the expression level comprises the use of a classifier. In some instances, the classifier comprises a probe selection region (PSR). Alternatively, the classifier comprises the use of an algorithm. In some instances, the algorithm comprises a machine learning algorithm. In some instances, assaying the expression level comprises sequencing the plurality of targets. In some instances, assaying the expression level comprises quantifying the plurality of targets.

Disclose herein, in some embodiments, is a probe set for assessing a cancer status of a subject comprising a plurality of probes, wherein the probes in the set are capable of detecting an expression level of one or more targets, wherein the expression level determines the cancer status of the subject with at least 40% specificity; and wherein at least one or more targets are selected from: (a) a target listed in Table 6; (b) a target comprising a sequence selected from SEQ ID NOs: 1-153 listed in Table 7; (c) a target comprising a sequence that is a complement of a sequence selected from SEQ ID NOs: 1-153 listed in Table 7; (d) a target comprising a sequence that is a reverse complement of a sequence selected from SEQ ID NOs: 1-153 listed in Table 7; or (e) a combination of (a-d). In some instances, the cancer is selected from the group consisting of a carcinoma, sarcoma, leukemia, lymphoma, myeloma, and a CNS tumor. In some instances, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some instances, the cancer is a prostate cancer. In some instances, the cancer is a pancreatic cancer. In some instances, the cancer is a thyroid cancer. In some instances, assessing the cancer status includes assessing cancer recurrence risk. In some instances, the assessing the cancer status includes determining a treatment modality. In some instances, assessing the cancer status includes determining the efficacy of treatment. In some instances, the one or more targets comprise a nucleic acid sequence. In some instances, the nucleic acid sequence is a DNA sequence. In some instances, the nucleic acid sequence is an RNA sequence. In some instances, the one or more targets are a non-coding RNA transcript. In some instances, the non-coding RNA transcript is non-polyadenylated. In some instances, the one or more targets are polyadenylated targets. In some embodiments, the one or more targets comprise an intronic sequence, a sequence within the UTR, or a non-coding RNA transcript. In some embodiments, the one or more targets comprise an intronic sequence or a portion of an intronic sequence. In some embodiments, the one or more of targets comprises a UTR sequence a portion of a UTR sequence. In some embodiments, the one or more targets comprise non-coding RNA transcript. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the one or more targets comprise an an exon-coding transcript. In some embodiments, the exon-coding transcript is an exonic sequence. In some embodiments, the probes in the set are capable of detecting an expression level of two or more targets. In some embodiments, the probes in the set are capable of detecting an expression level of three or more targets. In some embodiments the probes in the set are capable of detecting an expression level of five or more targets. In some embodiments, the probes in the set are capable of detecting an expression level of ten or more targets. In some embodiments, the probes in the set are capable of detecting an expression level of twenty or more targets. In some embodiments, the probes in the set are capable of detecting an expression level of thirty or more targets. In some embodiments, the probes in the set are capable of detecting an expression level of forty or more targets. In some embodiments, the probes in the set are capable of detecting an expression level of fifty or more targets. In some embodiments, the probes in the set are capable of detecting an expression level of sixty or more targets. In some embodiments, the probes in the set are capable of detecting an expression level of two or more targets selected from a target listed in Table 6. In some embodiments, the probes in the set are capable of detecting an expression level of three or more targets selected from a target listed in Table 6. In some embodiments, the probes in the set are capable of detecting an expression level of five or more targets selected from a target listed in Table 6. In some embodiments, the probes in the set are capable of detecting an expression level often or more targets selected from a target listed in Table 6. In some embodiments, the probes in the set are capable of detecting an expression level of twenty or more targets selected from a target listed in Table 6. In some embodiments, the probes in the set are capable of detecting an expression level of thirty or more targets selected from a target listed in Table 6. In some embodiments, the probes in the set are capable of detecting an expression level of two or more targets comprising a sequence selected from SEQ ID NOs: 1-153. In some embodiments, the probes in the set are capable of detecting an expression level of three or more targets comprising a sequence selected from SEQ ID NOs: 1-153. In some embodiments, the probes in the set are capable of detecting an expression level of five or more targets comprising a sequence selected from SEQ ID NOs: 1-153. In some embodiments, the probes in the set are capable of detecting an expression level of ten or more targets comprising a sequence selected from SEQ ID NOs: 1-153. In some embodiments, the probes in the set are capable of detecting an expression level of twenty or more targets comprising a sequence selected from SEQ ID NOs: 1-153. In some embodiments, the probes in the set are capable of detecting an expression level of thirty or more targets comprising a sequence selected from SEQ ID NOs: 1-153. In some embodiments, the probes in the set are capable of detecting an expression level of two or more targets comprising a sequence that is a complement of a sequence selected from SEQ ID NOs: 1-153. In some embodiments, the probes in the set are capable of detecting an expression level of three or more targets comprising a sequence that is a complement of a sequence selected from SEQ ID NOs: 1-153. In some embodiments, the probes in the set are capable of detecting an expression level of five or more targets comprising a sequence that is a complement of a sequence selected from SEQ ID NOs: 1-153. In some embodiments, the probes in the set are capable of detecting an expression level of ten or more targets comprising a sequence that is a complement of a sequence selected from SEQ ID NOs: 1-153. In some embodiments, the probes in the set are capable of detecting an expression level of twenty or more targets comprising a sequence that is a complement of a sequence selected from SEQ ID NOs: 1-153. In some embodiments, the probes in the set are capable of detecting an expression level of thirty or more targets comprising a sequence that is a complement of a sequence selected from SEQ ID NOs: 1-153. In some embodiments, the probes in the set are capable of detecting an expression level of two or more targets comprising a sequence that is a reverse complement of a sequence selected from SEQ ID NOs: 1-153. In some embodiments, the probes in the set are capable of detecting an expression level of three or more targets comprising a sequence that is a reverse complement of a sequence selected from SEQ ID NOs: 1-153. In some embodiments, the probes in the set are capable of detecting an expression level of five or more targets comprising a sequence that is a reverse complement of a sequence selected from SEQ ID NOs: 1-153. In some embodiments, the probes in the set are capable of detecting an expression level of ten or more targets comprising a sequence that is a complement of a sequence selected from SEQ ID NOs: 1-153. In some embodiments, the probes in the set are capable of detecting an expression level of twenty or more targets comprising a sequence that is a reverse complement of a sequence selected from SEQ ID NOs: 1-153. In some embodiments, the probes in the set are capable of detecting an expression level of thirty or more targets comprising a sequence that is a reverse complement of a sequence selected from SEQ ID NOs: 1-153. In some instances, the probes are between about 15 nucleotides and about 500 nucleotides in length. In some instances, the probes are between about 15 nucleotides and about 450 nucleotides in length. In some instances, the probes are between about 15 nucleotides and about 400 nucleotides in length. In some instances, the probes are between about 15 nucleotides and about 350 nucleotides in length. In some instances, the probes are between about 15 nucleotides and about 300 nucleotides in length. In some instances, the probes are between about 15 nucleotides and about 250 nucleotides in length. In some instances, the probes are between about 15 nucleotides and about 200 nucleotides in length. In some instances, the probes are at least 15 nucleotides in length. In some instances, the probes are at least 25 nucleotides in length. In some instances, the expression level determines the cancer status of the subject with at least 50% specificity. In some instances, the expression level determines the cancer status of the subject with at least 60% specificity. In some instances, the expression level determines the cancer status of the subject with at least 65% specificity. In some instances, the expression level determines the cancer status of the subject with at least 70% specificity. In some instances, the expression level determines the cancer status of the subject with at least 75% specificity. In some instances, the expression level determines the cancer status of the subject with at least 80% specificity. In some instances, the expression level determines the cancer status of the subject with at least 85% specificity.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

FIG. 1. Principal Component Analysis (PCA) of 57 training and 31 validation samples. The sources of variation between the samples was assessed by Pearson's correlation coefficient of the expression values of 1,137,256 filtedark grey probe sets showing a splom plot representation of the data. A: The training samples are color coded by the post-operative thyroidectomy review pathology diagnosis-malignant (x), benign (circle) thyroid nodule disease. B: The training samples are color coded by the pre-operative fine-needle aspirate cytology diagnosis-cancer (x), benign (circle), and 'suspicious for cancer' (+). C: The validation samples are color coded by the post-operative thyroidectomy review pathology diagnosis-malignant (x), benign (circle) thyroid nodule disease. D: The validation samples are color coded by the pre-operative fine-needle aspirate cytology diagnosis-cancer (x), benign (circle), and 'suspicious for cancer' (+).

FIG. 2. Hierarchical Clustering: Heat Maps of the 57 training and 31 validation samples. Hierarchical clustering of the samples computed using Pearson's correlation and complete distance metric of the 249-marker RNA expression signature. A: Heat Map for the training set, samples are color coded by the post-operative thyroidectomy review pathology diagnosis-malignant (dark grey), benign (light grey). B: Heat Map for the validation subset, samples are color coded by the post-operative thyroidectomy review pathology diagnosis-malignant (dark grey), benign (light grey). White/Light grey and dark grey represent over expression and under expression of one group over the other, respectively. C: Heat Map for the indeterminate subset of the validation subset color coded by the post-operative thyroidectomy review pathology diagnosis-malignant (dark grey), benign (light grey). White/Light grey and dark grey represent over expression and under expression of one group over the other, respectively.

FIG. 3. Multidimensional Scaling (MDS) of 57 training and 31 validation samples. The similarity of the expression profiles between samples was assessed by Pearson's correlation coefficient of the expression values of the 249-marker RNA expression signature. A: The training samples are color-coded by the post-operative thyroidectomy review pathology diagnosis-malignant (x), benign (circle) thyroid nodule disease. B: The training samples are color coded by the pre-operative fine-needle aspirate cytology diagnosis-cancer (x), benign (circle), and 'suspicious for cancer' (x). C: The validation samples are color coded by the post-operative thyroidectomy review pathology diagnosis-malignant (x), benign (circle) thyroid nodule disease. D: The validation samples are color coded by the pre-operative fine-needle aspirate cytology diagnosis-cancer (x), benign (circle), and 'suspicious for cancer' (+).

Figure 4:
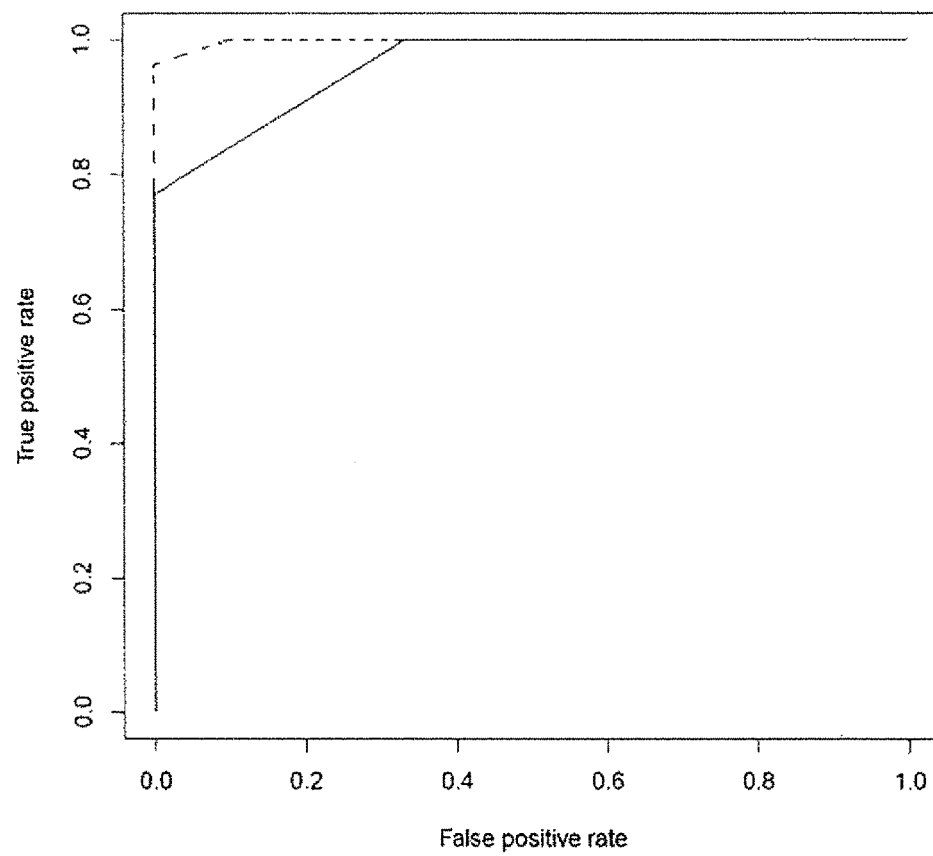
FIG. 4. Receiver Operating Characteristic (ROC) curve derived from the 249-marker RNA expression signature. The dotted and solid lines represent the training and validation set, respectively.

Table 1. Description of specimens utilized in Example 1
Table 2. Characteristics of samples used in Example 1
Table 3. Differential expression analysis of the training subset
Table 4. Training subset and Validation subset KNN values
Table 5. Specimen Clinical Data and KNN Score
Table 6. List of biomarkers
Table 7. List of Coding, Non-coding, and Non-exonic Transcript Sequences

DETAILED DESCRIPTION OF THE INVENTION

The present invention discloses systems and methods for diagnosing, predicting, and/or monitoring the status or outcome of a cancer in a subject using expression-based analysis of coding targets, non-coding targets, and/or non-exonic transcripts. Generally, the method comprises (a) optionally providing a sample from a subject suffering from a cancer; (b) assaying the expression level for a plurality of targets in the sample; and (c) diagnosing, predicting and/or monitoring the status or outcome of the cancer based on the expression level of the plurality of targets.

Assaying the expression level for a plurality of targets in the sample may comprise applying the sample to a microarray. In some instances, assaying the expression level may comprise the use of an algorithm. The algorithm may be used to produce a classifier. Alternatively, the classifier may comprise a probe selection region. Assaying the expression level for a plurality of targets may comprise detecting and/or quantifying the plurality of targets.

In some instances, the plurality of targets comprises one or more targets selected from Table 6. Alternatively, the plurality of targets comprises one or more targets comprising a sequence selected from SEQ ID NOs: 1-153. In some instances, the plurality of targets comprises one or more targets comprising a sequence that overlaps or partially overlaps with a sequence selected from SEQ ID NOs: 1-153. In some instances, the plurality of targets comprises one or more targets comprise a sequence that comprising 10 or more consecutive nucleotides of a sequence selected from SEQ ID NOs: 1-153. In some instances, the plurality of targets comprises one or more targets comprising a sequence that is complementary or reverse complementary to a sequence selected from SEQ ID NOs: 1-153. In some instances, the plurality of targets comprises one or more targets comprising a sequence that is complementary or reverse complementary to at least a portion of a sequence selected from SEQ ID NOs: 1-153. In some instances, the plurality of targets comprises one or more targets comprising a sequence that is substantially complementary or reverse complementary to at least a portion of a sequence selected from SEQ ID NOs: 1-153.

Further disclosed herein, is a probe set for diagnosing, predicting, and/or monitoring a cancer in a subject. In some instances, the probe set comprises a plurality of probes capable of detecting an expression level of one or more targets, wherein the expression level determines the cancer status of the subject with at least about 45% specificity. In some instances, the one or more targets are selected from a target listed in Table 6. Alternatively, the one or more targets comprise a sequence selected from SEQ ID NOs: 1-153. In some instances, the one or more targets comprise a sequence that overlaps or partially overlaps with a sequence selected from SEQ ID NOs: 1-153. In some instances, the one or more targets comprise a sequence that comprises 10 or more consecutive nucleotides of a sequence selected from SEQ ID NOs: 1-153. In some instances, the one or more targets comprise a sequence that is complementary or reverse complementary to a sequence selected from SEQ ID NOs: 1-153. In some instances, the one or more targets comprise a sequence that is complementary or reverse complementary to at least a portion of a sequence selected from SEQ ID NOs: 1-153. In some instances, the one or more targets comprise a sequence that is substantially complementary or reverse complementary to at least a portion of a sequence selected from SEQ ID NOs: 1-153.

Further disclosed herein are methods for characterizing a patient population. Generally, the method comprises: (a) providing a sample from a subject; (b) assaying the expression level for a plurality of targets in the sample; and (c) characterizing the subject based on the expression level of the plurality of targets. In some instances, the plurality of targets comprises one or more targets selected from Table 6. Alternatively, the plurality of targets comprises one or more targets comprising a sequence selected from SEQ ID NOs: 1-153. In some instances, the plurality of targets comprises one or more targets comprising a sequence that overlaps or partially overlaps with a sequence selected from SEQ ID NOs: 1-153. In some instances, the plurality of targets comprises one or more targets comprise a sequence that comprising 10 or more consecutive nucleotides of a sequence selected from SEQ ID NOs: 1-153. In some instances, the plurality of targets comprises one or more targets comprising a sequence that is complementary or reverse complementary to a sequence selected from SEQ ID NOs: 1-153. In some instances, the plurality of targets comprises one or more targets comprising a sequence that is complementary or reverse complementary to at least a portion of a sequence selected from SEQ ID NOs: 1-153. In some instances, the plurality of targets comprises one or more targets comprising a sequence that is substantially complementary or reverse complementary to at least a portion of a sequence selected from SEQ ID NOs: 1-153.

In some instances, characterizing the subject comprises determining whether the subject would respond to an anti-cancer therapy. Alternatively, characterizing the subject comprises identifying the subject as a non-responder to an anti-cancer therapy. Optionally, characterizing the subject comprises identifying the subject as a responder to an anti-cancer therapy.

Before the present invention is described in further detail, it is to be understood that this invention is not limited to the particular methodology, compositions, articles or machines described, as such methods, compositions, articles or machines can, of course, vary. It is also to be understood that the terminology used herein is for the purpose of describing particular embodiments only, and is not intended to limit the scope of the present invention.

Definitions

Unless defined otherwise or the context clearly dictates otherwise, all technical and scientific terms used herein have the same meaning as commonly understood by one of ordinary skill in the art to which this invention belongs. In describing the present invention, the following terms may be employed, and are intended to be defined as indicated below.

The term "polynucleotide" as used herein refers to a polymer of greater than one nucleotide in length of ribonucleic acid (RNA), deoxyribonucleic acid (DNA), hybrid RNA/DNA, modified RNA or DNA, or RNA or DNA mimetics, including peptide nucleic acids (PNAs). The polynucleotides may be single- or double-stranded. The term includes polynucleotides composed of naturally-occurring nucleobases, sugars and covalent internucleoside (backbone) linkages as well as polynucleotides having non-naturally-occurring portions which function similarly. Such modified or substituted polynucleotides are well known in the art and for the purposes of the present invention, are referred to as "analogues."

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarily exists when a polynucleotide may hybridize under selective hybridization conditions to its complement. Typically, selective hybridization may occur when there is at least about 65% complementarity over a stretch of at least 14 to 25 bases, for example at least about 75%, or at least about 90% complementarity.

"Preferential binding" or "preferential hybridization" refers to the increased propensity of one polynucleotide to bind to its complement in a sample as compared to a noncomplementary polymer in the sample.

Hybridization conditions may typically include salt concentrations of less than about 1M, more usually less than about 500 mM, for example less than about 200 mM. In the case of hybridization between a peptide nucleic acid and a polynucleotide, the hybridization can be done in solutions containing little or no salt. Hybridization temperatures can be as low as 5° C., but are typically greater than 22° C., and more typically greater than about 30° C., for example in excess of about 37° C. Longer fragments may require higher hybridization temperatures for specific hybridization as is known in the art. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

A "target sequence" as used herein (also occasionally referred to as a "PSR" or "probe selection region") refers to a region of the genome against which one or more probes can be designed. A "target sequence" may be a coding target or a non-coding target. A "target sequence" may comprise exonic and/or non-exonic sequences. Alternatively, a "target sequence" may comprise an ultraconserved region. An ultraconserved region is generally a sequence that is at least 200 base pairs and is conserved across multiple species. An ultraconserved region may be exonic or non-exonic. Exonic sequences may comprise regions on a protein-coding gene, such as an exon, UTR, or a portion thereof. Non-exonic sequences may comprise regions on a protein-coding, non protein-coding gene, or a portion thereof. For example, non-exonic sequences may comprise intronic regions, promoter regions, intergenic regions, a non-coding transcript, an exon anti-sense region, an intronic anti-sense region, UTR anti-sense region, non-coding transcript anti-sense region, or a portion thereof.

As used herein, a probe is any polynucleotide capable of selectively hybridizing to a target sequence or its complement, or to an RNA version of either. A probe may comprise ribonucleotides, deoxyribonucleotides, peptide nucleic acids, and combinations thereof. A probe may optionally comprise one or more labels. In some embodiments, a probe may be used to amplify one or both strands of a target sequence or an RNA form thereof, acting as a sole primer in an amplification reaction or as a member of a set of primers.

As used herein, a non-coding target may comprise a nucleotide sequence. The nucleotide sequence is a DNA or RNA sequence. A non-coding target may include a UTR sequence, an intronic sequence, or a non-coding RNA transcript. A non-coding target also includes sequences which partially overlap with a UTR sequence or an intronic sequence. A non-coding target also includes non-exonic transcripts.

As used herein, a non-coding RNA (ncRNA) transcript is an RNA transcript that does not encode a protein. ncRNAs include short ncRNAs and long ncRNAs (lncRNAs). Short ncRNAs are ncRNAs that are generally 18-200 nucleotides (nt) in length. Examples of short ncRNAs include, but are not limited to, microRNAs (miRNAs), piwi-associated RNAs (piRNAs), short interfering RNAs (siRNAs), promoter-associated short RNAs (PASRs), transcription initiation RNAs (tiRNAs), termini-associated short RNAs (TASRs), antisense termini associated short RNAs (aTASRs), small nucleolar RNAs (snoRNAs), transcription start site antisense RNAs (TSSa-RNAs), small nuclear RNAs (snRNAs), retroposon-derived RNAs (RE-RNAs), 3'UTR-derived RNAs (uaRNAs), x-ncRNA, human Y RNA (hY RNA), unusually small RNAs (usRNAs), small NF90-associated RNAs (snaRs), vault RNAs (vtRNAs), small Cajal body-specific RNAs (scaRNAs), and telomere specific small RNAs (tel-sRNAs). LncRNAs are cellular RNAS, exclusive of rRNAs, greater than 200 nucleotides in length and having no obvious protein-coding capacity (Lipovich L, et al., MacroRNA underdogs in a microRNA world: evolutionary, regulatory, and biomedical significance of mammalian long non-protein-coding RNA, *Biochim Biophys Acta*, 2010, 1799(9): 597-615). LncRNAs include, but are not limited to, large or long intergenic ncRNAs (lincRNAs), transcribed ultraconserved regions (T-UCRs), pseudogenes, GAA-repeat containing RNAs (GRC-RNAs), long intronic ncRNAs, antisense RNAs (aRNAs), promoter-associated long RNAs (PALRs), promoter upstream transcripts (PROMPTS), and long stress-induced non-coding transcripts (LSINCTs).

As used herein, a coding target includes nucleotide sequences that encode for a protein and peptide sequences. The nucleotide sequence is a DNA or RNA sequence. The coding target includes protein-coding sequence. Protein-coding sequences include exon-coding sequences (e.g., exonic sequences).

As used herein, diagnosis of cancer may include the identification of cancer in a subject, determining the malignancy of the cancer, or determining the stage of the cancer.

As used herein, prognosis of cancer may include predicting the clinical outcome of the patient, assessing the risk of cancer recurrence, determining treatment modality, or determining treatment efficacy.

"Having" is an open-ended phrase like "comprising" and "including," and includes circumstances where additional elements are included and circumstances where they are not.

"Optional" or "optionally" means that the subsequently described event or circumstance may or may not occur, and that the description includes instances where the event or circumstance occurs and instances in which it does not.

As used herein 'NED' describes a clinically distinct disease state in which patients show no evidence of disease (NED') at least 5 years after surgery, 'PSA' describes a clinically distinct disease state in which patients show biochemical relapse only (two successive increases in prostate-specific antigen levels but no other symptoms of disease with at least 5 years follow up after surgery; 'PSA') and 'SYS' describes a clinically distinct disease state in which patients develop biochemical relapse and present with systemic cancer disease or metastases ('SYS') within five years after the initial treatment with radical prostatectomy.

As used herein, the term "subject" refers to mammals or non-mammals. In some instances, the subject is a mammal, such as, a human, non-human primate (e.g., apes, monkeys, chimpanzees), cat, dog, rabbit, goat, horse, cow, pig, and sheep. In some instances, the subject is a human. The subject can be male or female; the subject can be a fetus, infant, child, adolescent, teenager or adult. In some instances, the subject is a non-mammal. Non-mammals include, but are not limited to, reptiles, amphibians, avians, and fish. A reptile may be a lizard, snake, alligator, turtle, crocodile, and tortoise. An amphibian may be a toad, frog, newt, and salamander. Examples of avians include, but are not limited to, ducks, geese, penguins, ostriches, and owls. Examples of fish include, but are not limited to, catfish, eels, sharks, and swordfish. In some instances, the subject is a patient or other individual undergoing a treatment regimen, or being evaluated for a treatment regimen (e.g., anti-cancer therapy). However, in some cases, the subject is not undergoing a treatment regimen.

As used herein, the term "about" refers to approximately a +/−10% variation from a given value. It is to be understood that such a variation is always included in any given value provided herein, whether or not it is specifically referred to.

Use of the singular forms "a," "an," and "the" include plural references unless the context clearly dictates otherwise. Thus, for example, reference to "a polynucleotide" includes a plurality of polynucleotides, reference to "a target" includes a plurality of such targets, reference to "a normalization method" includes a plurality of such methods, and the like. Additionally, use of specific plural references, such as "two," "three," etc., read on larger numbers of the same subject, unless the context clearly dictates otherwise.

Terms such as "connected," "attached," "linked" and "conjugated" are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each sub-range between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values, which are about the same quantity or amount as the recited value, are also within the scope of the invention, as are ranges based thereon. Where a combination is disclosed, each sub-combination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Targets

The methods disclosed herein often comprise assaying the expression level of a plurality of targets. The plurality of targets may comprise coding targets and/or non-coding targets of a protein-coding gene or a non protein-coding gene. In some instances, a protein-coding gene structure comprises an exon and an intron. The exon can further comprise a coding sequence (CDS) and an untranslated region (UTR). The protein-coding gene can be transcribed to produce a pre-mRNA and the pre-mRNA can be processed to produce a mature mRNA. The mature mRNA may be translated to produce a protein.

In some instances, a non protein-coding gene structure comprises an exon and intron. Usually, the exon region of a non protein-coding gene primarily contains a UTR. The non protein-coding gene may be transcribed to produce a pre-mRNA and the pre-mRNA may be processed to produce a non-coding RNA (ncRNA).

In some instances, a coding target comprises a coding sequence of an exon. In some instances, a non-coding target comprises a UTR sequence of an exon, intron sequence, intergenic sequence, promoter sequence, non-coding transcript, CDS antisense, intronic antisense, UTR antisense, non-coding transcript antisense, or any combination thereof. In some instances, a non-coding transcript comprises a non-coding RNA (ncRNA).

In some instances, the plurality of targets may be differentially expressed. In some instances, one or more targets are over-expressed. Alternatively, one or more targets are under-expressed. In some instances, differential expression is determined by comparing the expression of the plurality of targets from a subject to the expression of the plurality from a control sample. In some instances, the control sample is an untreated subject. In some instances, the control sample is from a treated subject. Alternatively, the control sample is from a healthy subject. In some instances, the control sample is from a subject suffering from a cancer.

In some instances, the plurality of targets comprises a coding target and/or a non-coding target. In some instances, a non-coding target comprises a UTR sequence, an intronic sequence, or a non-coding RNA transcript. In some instances, a non-coding target comprises sequences which partially overlap with a UTR sequence or an intronic sequence. A non-coding target can also include non-exonic transcripts. Exonic sequences may comprise regions on a protein-coding gene, such as an exon, UTR, or a portion thereof. Non-exonic sequences may comprise regions on a protein-coding, non protein-coding gene, or a portion thereof. For example, non-exonic sequences may comprise intronic regions, promoter regions, intergenic regions, a non-coding transcript, an exon anti-sense region, an intronic anti-sense region, UTR anti-sense region, non-coding transcript anti-sense region, or a portion thereof.

In some instances, the coding target and/or non-coding target is at least about 70% identical to a sequence selected from SEQ ID NOs: 1-153. Alternatively, the coding target and/or non-coding target are at least about 80% identical to a sequence selected from SEQ ID NOs: 1-153. In some instances, the coding target and/or non-coding target are at least about 85% identical to a sequence selected from SEQ ID NOs: 1-153. In some instances, the coding target and/or non-coding target are at least about 90% identical to a sequence selected from SEQ ID NOs: 1-153. Alternatively, the coding target and/or non-coding target are at least about 95% identical to a sequence selected from SEQ ID NOs: 1-153.

In some instances, the plurality of targets comprises one or more targets selected from Table 6. In some instances, the plurality of targets comprises at least 5, 10, 15, 20, 25, 30, 35, 40, 45, 50, 55, 60, 65, 70, 75, 80, 85, 90, 95, or 100 targets selected from Table 6. In some instances, the plurality of targets comprises at least 20 targets selected from Table 6.

Alternatively, the plurality of targets comprises one or more targets comprising a sequence selected from SEQ ID NOs: 1-153. In some instances, the plurality of targets comprises five or more targets comprising a sequence selected from SEQ ID NOs: 1-153. In some instances, the plurality of targets comprises ten or more targets comprising a sequence selected from SEQ ID NOs: 1-153. In some instances, the plurality of targets comprises fifteen or more targets comprising a sequence selected from SEQ ID NOs: 1-153. In some instances, the plurality of targets comprises twenty or more targets comprising a sequence selected from SEQ ID NOs: 1-153. In some instances, the plurality of targets comprises at least 30, 35, 40, 45, 50, 55, 60, 65, 70, 75, 80, 85, 90, 95, or 100 targets comprising a sequence selected from SEQ ID NOs: 1-153. In some instances, the plurality of targets comprises one or more targets comprising a sequence that overlaps or partially overlaps with a sequence selected from SEQ ID NOs: 1-153. In some instances, the plurality of targets comprises one or more targets comprising a sequence that is at least 70% identical to a sequence selected from SEQ ID NOs: 1-153. In some instances, the plurality of targets comprises one or more targets comprising a sequence that is at least 80% identical to a sequence selected from SEQ ID NOs: 1-153. In some instances, the plurality of targets comprises one or more targets comprising a sequence that is at least 85% identical to a sequence selected from SEQ ID NOs: 1-153. In some instances, the plurality of targets comprises one or more targets comprising a sequence that is at least 90% identical to a sequence selected from SEQ ID NOs: 1-153. In some instances, the plurality of targets comprises one or more targets comprising a sequence that is at least 95% identical to a sequence selected from SEQ ID NOs: 1-153. In some instances, the plurality of targets comprises one or more targets comprising a sequence that is at least 97% identical to a sequence selected from SEQ ID NOs: 1-153. In some instances, the plurality of targets comprises one or more targets comprising a sequence that is at least 99% identical to a sequence selected from SEQ ID NOs: 1-153.

In some instances, the plurality of targets comprises one or more targets comprising a sequence that comprising 10 or more consecutive nucleotides of a sequence selected from SEQ ID NOs: 1-153. In some instances, the plurality of targets comprises five or more targets comprising a sequence that comprises 10 or more consecutive nucleotides of a sequence selected from SEQ ID NOs: 1-153. In some instances, the plurality of targets comprises ten or more targets comprising a sequence that comprises 10 or more consecutive nucleotides of a sequence selected from SEQ ID NOs: 1-153. In some instances, the plurality of targets comprises fifteen or more targets comprising a sequence that comprises 10 or more consecutive nucleotides of a sequence selected from SEQ ID NOs: 1-153. In some instances, the plurality of targets comprises twenty or more targets comprising a sequence that comprises 10 or more consecutive nucleotides of a sequence selected from SEQ ID NOs: 1-153. In some instances, the plurality of targets comprises at least 30, 35, 40, 45, 50, 55, 60, 65, 70, 75, 80, 85, 90, 95, or 100 targets comprising a sequence that comprises 10 or more consecutive nucleotides of a sequence selected from SEQ ID NOs: 1-153. In some instances, the plurality of targets comprises a sequence that comprises 20 or more consecutive nucleotides of a sequence selected from SEQ ID NOs: 1-153. In some instances, the plurality of targets comprises a sequence that comprises 30 or more consecutive nucleotides of a sequence selected from SEQ ID NOs: 1-153. In some instances, the plurality of targets comprises a sequence that comprises 40 or more consecutive nucleotides of a sequence selected from SEQ ID NOs: 1-153. In some instances, the plurality of targets comprises a sequence that comprises 50 or more consecutive nucleotides of a sequence selected from SEQ ID NOs: 1-153. In some instances, the plurality of targets comprises a sequence that comprises 60 or more consecutive nucleotides of a sequence selected from SEQ ID NOs: 1-153. In some instances, the plurality of targets comprises a sequence that comprises at least 70, 80, 90, 100, 125, 150, 200, 250, or 300 consecutive nucleotides of a sequence selected from SEQ ID NOs: 1-153. In some instances, the plurality of targets comprises a sequence that comprises at least 350, 400, 450, 500, 600, 700, 800, 900, or 1000 consecutive nucleotides of a sequence selected from SEQ ID NOs: 1-153. In some instances, the plurality of targets comprises a sequence that comprises at least 1100, 1200, 1300, or 1400 consecutive nucleotides of a sequence selected from SEQ ID NOs: 1-153.

In some instances, the plurality of targets comprises one or more targets comprising a sequence that is complementary to a sequence selected from SEQ ID NOs: 1-153. In some instances, the plurality of targets comprises one or more targets comprising a sequence that is substantially complementary to a sequence selected from SEQ ID NOs: 1-153. In some instances, the plurality of targets comprises one or more targets comprising a sequence that is complementary to at least a portion of a sequence selected from SEQ ID NOs: 1-153. In some instances, the plurality of targets comprises one or more targets comprising a sequence that is substantially complementary to at least a portion of a sequence selected from SEQ ID NOs: 1-153.

In some instances, the plurality of targets comprises one or more targets comprising a sequence that is complementary to 10 or more consecutive nucleotides of a sequence selected from SEQ ID NOs: 1-153. In some instances, the plurality of targets comprises five or more targets comprising a sequence that is complementary to 10 or more consecutive nucleotides of a sequence selected from SEQ ID NOs: 1-153. In some instances, the plurality of targets comprises ten or more targets comprising a sequence that is complementary to 10 or more consecutive nucleotides of a sequence selected from SEQ ID NOs: 1-153. In some instances, the plurality of targets comprises fifteen or more targets comprising a sequence that is complementary to 10 or more consecutive nucleotides of a sequence selected from SEQ ID NOs: 1-153. In some instances, the plurality of targets comprises twenty or more targets comprising a sequence that is complementary to 10 or more consecutive nucleotides of a sequence selected from SEQ ID NOs: 1-153. In some instances, the plurality of targets comprises at least 30, 35, 40, 45, 50, 55, 60, 65, 70, 75, 80, 85, 90, 95, or 100 targets comprising a sequence that is complementary to 10 or more consecutive nucleotides of a sequence selected from SEQ ID NOs: 1-153. In some instances, the plurality of targets comprises a sequence that is complementary to 20 or more consecutive nucleotides of a sequence selected from SEQ ID NOs: 1-153. In some instances, the plurality of targets comprises a sequence that is complementary to 30 or more consecutive nucleotides of a sequence selected from SEQ ID NOs: 1-153. In some instances, the plurality of targets comprises a sequence that is complementary to 40 or more consecutive nucleotides of a sequence selected from SEQ ID NOs: 1-153. In some instances, the plurality of targets comprises a sequence that is complementary to 50 or more consecutive nucleotides of a sequence selected from SEQ ID NOs: 1-153. In some instances, the plurality of targets comprises a sequence that is complementary to 60 or more consecutive nucleotides of a sequence selected from SEQ ID NOs: 1-153. In some instances, the plurality of targets comprises a sequence that is complementary to at least 70, 80, 90, 100, 125, 150, 200, 250, or 300 consecutive nucleotides of a sequence selected from SEQ ID NOs: 1-153. In some instances, the plurality of targets comprises a sequence that is complementary to at least 350, 400, 450, 500, 600, 700, 800, 900, or 1000 consecutive nucleotides of a sequence selected from SEQ ID NOs: 1-153. In some instances, the plurality of targets comprises a sequence that is complementary to at least 1100, 1200, 1300, or 1400 consecutive nucleotides of a sequence selected from SEQ ID NOs: 1-153.

In some instances, the plurality of targets comprises one or more targets comprising a sequence that is reverse complementary to a sequence selected from SEQ ID NOs: 1-153. In some instances, the plurality of targets comprises one or more targets comprising a sequence that is reverse complementary to at least a portion of a sequence selected from SEQ ID NOs: 1-153.

In some instances, the plurality of targets comprises one or more targets comprising a sequence that is reverse complementary to 10 or more consecutive nucleotides of a sequence selected from SEQ ID NOs: 1-153. In some instances, the plurality of targets comprises five or more targets comprising a sequence that is reverse complementary to 10 or more consecutive nucleotides of a sequence selected from SEQ ID NOs: 1-153. In some instances, the plurality of targets comprises ten or more targets comprising a sequence that is reverse complementary to 10 or more consecutive nucleotides of a sequence selected from SEQ ID NOs: 1-153. In some instances, the plurality of targets comprises fifteen or more targets comprising a sequence that is reverse complementary to 10 or more consecutive nucleotides of a sequence selected from SEQ ID NOs: 1-153. In some instances, the plurality of targets comprises twenty or more targets comprising a sequence that is reverse complementary to 10 or more consecutive nucleotides of a sequence selected from SEQ ID NOs: 1-153. In some instances, the plurality of targets comprises at least 30, 35, 40, 45, 50, 55, 60, 65, 70, 75, 80, 85, 90, 95, or 100 targets comprising a sequence that is reverse complementary to 10 or more consecutive nucleotides of a sequence selected from SEQ ID NOs: 1-153. In some instances, the plurality of targets comprises a sequence that is reverse complementary to 20 or more consecutive nucleotides of a sequence selected from SEQ ID NOs: 1-153. In some instances, the plurality of targets comprises a sequence that is reverse complementary to 30 or more consecutive nucleotides of a sequence selected from SEQ ID NOs: 1-153. In some instances, the plurality of targets comprises a sequence that is reverse complementary to 40 or more consecutive nucleotides of a sequence selected from SEQ ID NOs: 1-153. In some instances, the plurality of targets comprises a sequence that is reverse complementary to 50 or more consecutive nucleotides of a sequence selected from SEQ ID NOs: 1-153. In some instances, the plurality of targets comprises a sequence that is reverse complementary to 60 or more consecutive nucleotides of a sequence selected from SEQ ID NOs: 1-153. In some instances, the plurality of targets comprises a sequence that is reverse complementary to at least 70, 80, 90, 100, 125, 150, 200, 250, or 300 consecutive nucleotides of a sequence selected from SEQ ID NOs: 1-153. In some instances, the plurality of targets comprises a sequence that is reverse complementary to at least 350, 400, 450, 500, 600, 700, 800, 900, or 1000 consecutive nucleotides of a sequence selected from SEQ ID NOs: 1-153. In some instances, the plurality of targets comprises a sequence that is reverse complementary to at least 1100, 1200, 1300, or 1400 consecutive nucleotides of a sequence selected from SEQ ID NOs: 1-153.

In some instances, the plurality of targets comprises one or more targets comprising a sequence that hybridizes to a sequence selected from SEQ ID NOs: 1-153, a complement of a sequence selected from SEQ ID NOs: 1-153, or a reverse complement of a sequence selected from SEQ ID NOs: 1-153. In some instances, the plurality of targets comprises one or more targets comprising a sequence that hybridizes to at least a portion of a sequence selected from SEQ ID NOs: 1-153, a complement of a sequence selected from SEQ ID NOs: 1-153, or a reverse complement of a sequence selected from SEQ ID NOs: 1-153. In some instances, the sequence hybridizes to at least 10 consecutive nucleotides of a sequence selected from SEQ ID NOs: 1-153, a complement of a sequence selected from SEQ ID NOs: 1-153, or a reverse complement of a sequence selected from SEQ ID NOs: 1-153. In some instances, the sequence hybridizes to at least 15 consecutive nucleotides of a sequence selected from SEQ ID NOs: 1-153, a complement of a sequence selected from SEQ ID NOs: 1-153, or a reverse complement of a sequence selected from SEQ ID NOs: 1-153. In some instances, the sequence hybridizes to at least 20 consecutive nucleotides of a sequence selected from SEQ ID NOs: 1-153, a complement of a sequence selected from SEQ ID NOs: 1-153, or a reverse complement of a sequence selected from SEQ ID NOs: 1-153. In some instances, the sequence hybridizes to at least 25 consecutive nucleotides of a sequence selected from SEQ ID NOs: 1-153, a complement of a sequence selected from SEQ ID NOs: 1-153, or a reverse complement of a sequence selected from SEQ ID NOs: 1-153. In some instances, the sequence hybridizes to at least 30, 40, 50, 60, 70, 80, 90, or 100 consecutive nucleotides of a sequence selected from SEQ ID NOs: 1-153, a complement of a sequence selected from SEQ ID NOs: 1-153, or a reverse complement of a sequence selected from SEQ ID NOs: 1-153. In some instances, the sequence hybridizes to at least 150, 200, 250, 300, 350, 400, 450, 500, 600, 700, 800, 900, or 1000 consecutive nucleotides of a sequence selected from SEQ ID NOs: 1-153, a complement of a sequence selected from SEQ ID NOs: 1-153, or a reverse complement of a sequence selected from SEQ ID NOs: 1-153. In some instances, the sequence hybridizes to a complement of a sequence selected from SEQ ID NOs: 1-153, a complement of a sequence selected from SEQ ID NOs: 1-153, or a reverse complement of a sequence selected from SEQ ID NOs: 1-153.

In some instances, the plurality of targets comprises two or more targets comprising sequences selected from (a) SEQ ID NOs: 1-153; (b) a sequence with at least 80% identity to sequences listed in (a); (c) a complement thereof; or (d) a reverse complement thereof. In some instances, the plurality of targets comprises three or more targets comprising sequences selected from (a) SEQ ID NOs: 1-153; (b) a sequence with at least 80% identity to sequences listed in (a); (c) a complement thereof; or (d) a reverse complement thereof. In some instances, the plurality of targets comprises five or more targets comprising sequences selected from (a) SEQ ID NOs: 1-153; (b) a sequence with at least 80% identity to sequences listed in (a); (c) a complement thereof; or (d) a reverse complement thereof. In some instances, the plurality of targets comprises six or more targets comprising sequences selected from (a) SEQ ID NOs: 1-153; (b) a sequence with at least 80% identity to sequences listed in (a); (c) a complement thereof; or (d) a reverse complement thereof. In some instances, the plurality of targets comprises ten or more targets comprising sequences selected from (a) SEQ ID NOs: 1-153; (b) a sequence with at least 80% identity to sequences listed in (a); (c) a complement thereof; or (d) a reverse complement thereof. In some instances, the plurality of targets comprises at least 15, 20, 25, 30, 35, 40, 50, 60, 70, 80, 90, or 100 targets comprising sequences selected from (a) SEQ ID NOs: 1-153; (b) a sequence with at least 80% identity to sequences listed in (a); (c) a complement thereof; or (d) a reverse complement thereof.

In some instances, plurality of targets comprises (a) one or more targets selected from Table 6; and (b) one or more targets not selected from Table 6. In some instances, the one or more targets not selected from Table 6 comprise a target disclosed in U.S. patent application Ser. Nos. 13/254,571 and 13/258,429. In some instances, plurality of targets comprises (a) one or more targets comprising a sequence selected from SEQ ID NOs: 1-153, an RNA form thereof; a complement thereof, a reverse complement thereof; and (b) one or more targets comprising a sequence not selected from SEQ ID NOs: 1-153. In some instances, the one or more targets comprising a sequence not selected from SEQ ID NOs: 1-153 comprise a sequence disclosed in U.S. patent application Ser. Nos. 13/254,571 and 13/258,429.

Non-Coding RNAs

In some instances, the plurality of targets comprises one or more targets comprising a non-coding RNA. Generally, non-coding RNAs (ncRNAs) are functional transcripts that do not code for proteins. ncRNAs are loosely grouped into two major classes based on transcript size: small ncRNAs and large ncRNAs (lncRNAs).

Small ncRNAs

In some instances, the non-coding RNA is a small ncRNA. Small ncRNAs are typically 18 to 200 nucleotides (nt) in size and may be processed from longer precursors. Examples of small ncRNAs include, but are not limited to, microRNAs (miRNAs), piwi-associated RNAs (piRNAs), short interfering RNAs (siRNAs), promoter-associated short RNAs (PASRs), transcription initiation RNAs (tiRNAs), termini-associated short RNAs (TASRs), antisense termini associated short RNAs (aTASRs), small nucleolar RNAs (snoRNAs), transcription start site antisense RNAs (TSSa-RNAs), small nuclear RNAs (snRNAs), retroposon-derived RNAs (RE-RNAs), 3'UTR-derived RNAs (uaRNAs), x-ncRNA, human Y RNA (hY RNA), unusually small RNAs (usRNAs), small NF90-associated RNAs (snaRs), vault RNAs (vtRNAs), small Cajal body-specific RNAs (scaR-NAs), and telomere specific small RNAs (tel-sRNAs).

miRNAs

In some instances, the non-coding RNA is a miRNA. miRNAs can be divided into two subclasses: canonical and non-canonical miRNAs. Canonical miRNAs may initially be transcribed as long RNAs that contain hairpins. The 60-75 nt hairpins can be recognized by the RNA-binding protein Dgcr8 (DiGeorge syndrome critical region 8), which may direct the RNase III enzyme Drosha to cleave the base of the hairpin. Following cleavage by the Drosha-Dgcr8 complex, also called the microprocessor, the released hairpin may be transported to the cytoplasm, where Dicer, another RNase III enzyme, then cleaves it into a single short 18-25 nt dsRNA. Non-canonical miRNAs may bypass processing by the microprocessor by using other endonucleases or by direct transcription of a short hairpin. The resulting pre-miRNAs can then be exported from the nucleus and cleaved once by Dicer.

piRNAs

In some instances, the non-coding RNA is a piRNA. The piRNAs may differ from the miRNAs and endo-siRNAs in that they often do not require Dicer for their processing. piRNAs may be 25-32 nt in length, and can be expressed in the germline in mammals. They may be defined by their interaction with the Piwi proteins, a distinct family of Argonaute proteins (including Miwi, Miwi2 and Mili in mouse; also known as Piwil1, Piwil4 and Piwil2, respectively). piRNAs can be generated from long single-stranded RNA precursors that are often encoded by complex and repetitive intergenic sequences.

siRNAs

In some instances, the non-coding RNA is a siRNA. siRNAs can be derived from long dsRNAs in the form of either sense or antisense RNA pairs or as long hairpins, which may then directly be processed by Dicer consecutively along the dsRNA to produce multiple siRNAs. Therefore, canonical miRNAs, non-canonical miRNAs and endo-siRNAs may involve Dicer processing and can be ~21 nt in length. Furthermore, in all three cases, one strand of the Dicer product may associate with an Argonaute protein (Ago 1-4 in mammals; also known as Eif2c1-4) to form the active RISC (RNA-induced silencing complex). Often, these ribonucleoprotein complexes may be able to bind to and control the levels and translation of their target mRNAs, if the match between the small RNA and its target is perfect, the target is cleaved; if not, the mRNA is destabilized through as yet unresolved mechanisms.

PASRs, tiRNAs, and TSSa-RNAs

In some instances, the non-coding RNA is a PASR. PASRs can be broadly defined as short transcripts, generally 20-200 nt long, capped, with 5' ends that coincide with the transcription start sites (TSSs) of protein and non-coding genes. TiRNAs are predominantly 18 nt in length and generally found downstream of TSSs. TSSa-RNAs can be 20-90 nt long and may be localized with −250 to +50 of transcription start sites (TSSs). PASRs, tiRNAs, and TSSa-RNAs may strongly associated with highly expressed genes and regions of RNA Polymerase II (RNAPII) binding, may be weakly expressed, and may show bidirectional distributions that mirror RNAPII (Taft J, et al., Evolution, biogenesis and function of promoter-associated RNAs, *Cell Cycle*, 2009, 8(15):2332-2338).

TASRs and aTASRs

In some instances, the non-coding RNA is a TASR. TASRs may be 22-200 nt in length and are found to cluster at 5' and 3' termini of annotated genes. In some instances, the non-coding RNA is an aTASR. aTASRs can be found within 50 bp and antisense to 3' UTRs of annotated transcripts.

snoRNAs

In some instances, the non-coding RNA is a snoRNA. SnoRNAs represent one of the largest groups of functionally diverse trans-acting ncRNAs currently known in mammalian cells. snoRNAs can range between 60-150 nucleotides in length. From a structural basis, snoRNAs may fall into two categories termed box C/D snoRNAs (SNORDs) and box H/ACA snoRNAs (SNORAs). SNORDs can serve as guides for the 2'-O-ribose methylation of rRNAs or snRNAs, whereas SNORAs may serve as guides for the isomerization of uridine residues into pseudouridine.

snRNAs

In some instances, the non-coding RNA is a snRNA. snRNAs, historically referred to as U-RNAs, may be less than 200 nt long and may play key roles in pre-mRNA splicing. snRNAs are further divided into two main categories based on shared sequences and associated proteins. Sm-class RNAs can have a 5' trimethylguanosine cap and bind several Sm proteins. Lsm-RNAs may possess a monomethylphosphate 5' cap and a uridine rich 3' end acting as a binding site for Lsm proteins. Sm class of snRNAs (U1, U2, U4 and U5) are synthesized by RNA Pol II. For Sin class, pre-snRNAs are transcribed and 5' monomethyl-guanosine capped in the nucleus, exported via multiple factors to the cytoplasm for further processing. After cytoplamic hypermethylation of 5' cap (trimethylguanosine) and 3' trimming, the snRNA is translocated back into the nucleus. snRNPs for Sm class snRNAs are also assembled in the cytosol. Lsm snRNA (U6 and other snoRNAs) are transcribed by Pol III and keep the monomethylguanosine 5' cap and in the nucleus. Lsm snRNAs never leave the nucleus.

lncRNAs

In some instances, the non-coding RNA is a lncRNA. LncRNAs are cellular RNAS, exclusive of rRNAs, greater than 200 nucleotides in length and having no obvious protein-coding capacity (Lipovich L, et al., MacroRNA underdogs in a microRNA world: evolutionary, regulatory, and biomedical significance of mammalian long non-protein-coding RNA, *Biochim Biophys Acta,* 2010, 1799(9): 597-615). LncRNAs include, but are not limited to, large or long intergenic ncRNAs (lincRNAs), transcribed ultraconserved regions (T-UCRs), pseudogenes, GAA-repeat containing RNAs (GRC-RNAs), long intronic ncRNAs, antisense RNAs (aRNAs), promoter-associated long RNAs (PALRs), promoter upstream transcripts (PROMPTs), and long stress-induced non-coding transcripts (LSINCTs).

T-UCRs

In some instances, the non-coding RNA is a T-UCR. T-UCRs are transcribed genomic elements longer than 200 base pairs (bp) (range: 200-779 bp) that are absolutely conserved (100% identity with no insertion or deletions) among mouse, rat, and human genomes. T-UCRs may be intergenic (located between genes), intronic, exonic, partially exonic, exon containing, or "multiple" (location varies because of gene splice variants).

Pseudogenes

In some instances, the non-coding RNA is a pseudogene. Pseudogenes are commonly defined as sequences that resemble known genes but cannot produce functional proteins. Pseudogenes can be broadly classified into two categories: processed and nonprocessed. Nonprocessed pseudogenes usually contain introns, and they are often located next to their paralogous parent gene. Processed pseudogenes are thought to originate through retrotransposition; accordingly, they lack introns and a promoter region, but they often contain a polyadenylation signal and are flanked by direct repeats.

Probes/Primers

The present invention provides for a probe set for diagnosing, monitoring and/or predicting a status or outcome of a cancer in a subject comprising a plurality of probes, wherein (i) the probes in the set are capable of detecting an expression level of one or more targets selected from Table 6 and/or one or more targets comprising a sequence selected from SEQ ID NOs: 1-153; and (ii) the expression level determines the cancer status of the subject with at least about 40% specificity.

The probe set may comprise one or more polynucleotide probes. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a target sequence in the probe set. Computer programs can also be employed to select probe sequences that may not cross hybridize or may not hybridize non-specifically.

In some instances, microarray hybridization of RNA, extracted from prostate cancer tissue samples and amplified, may yield a dataset that is then summarized and normalized by the fRMA technique. The raw expression probes are summarized and normalized into probe selection regions ("PSRs"). The cross-hybridizing PSRs, highly variable PSRs (variance above the 90th percentile), and PSRs containing more than 4 probes are removed or filtered. Following fRMA and filtration, the data can be decomposed into its principal components and an analysis of variance model is used to determine the extent to which a batch effect remains present in the first 10 principal components.

These remaining PSRs can then be subjected to filtration by a T-test between CR (clinical recurrence) and non-CR samples. A p-value cut-off of 0.01 can be used for further refinement of the PSRs. Feature selection can be performed by regularized logistic regression using the elastic-net penalty. The regularized regression can be bootstrapped over 1000 times using all training data; with each iteration of bootstrapping features that have non-zero co-efficient following 3-fold cross validation were tabulated. In some instances, features that were selected in at least 25% of the total runs were used for model building.

One skilled in the art understands that the nucleotide sequence of the polynucleotide probe need not be identical to its target sequence in order to specifically hybridize thereto. The polynucleotide probes of the present invention, therefore, comprise a nucleotide sequence that is at least about 65% identical to a region of the coding target or non-coding target. In another embodiment, the nucleotide sequence of the polynucleotide probe is at least about 70% identical a region of the coding target or non-coding target. In another embodiment, the nucleotide sequence of the polynucleotide probe is at least about 75% identical a region of the coding target or non-coding target. In another embodiment, the nucleotide sequence of the polynucleotide probe is at least about 80% identical a region of the coding target or non-coding target. In another embodiment, the nucleotide sequence of the polynucleotide probe is at least about 85% identical a region of the coding target or non-coding target. In another embodiment, the nucleotide sequence of the polynucleotide probe is at least about 90% identical a region of the coding target or non-coding target. In a further embodiment, the nucleotide sequence of the polynucleotide probe is at least about 95% identical to a region of the coding target or non-coding target.

Methods of determining sequence identity are known in the art and can be determined, for example, by using the BLASTN program of the University of Wisconsin Computer Group (GCG) software or provided on the NCBI website. The nucleotide sequence of the polynucleotide probes of the present invention may exhibit variability by differing (e.g., by nucleotide substitution, including transition or transversion) at one, two, three, four or more nucleotides from the sequence of the coding target or non-coding target.

Other criteria known in the art may be employed in the design of the polynucleotide probes of the present invention. For example, the probes can be designed to have <50% G content and/or between about 25% and about 70% G+C content. Strategies to optimize probe hybridization to the target nucleic acid sequence can also be included in the process of probe selection.

Hybridization under particular pH, salt, and temperature conditions can be optimized by taking into account melting temperatures and by using empirical rules that correlate with desired hybridization behaviors. Computer models may be used for predicting the intensity and concentration-dependence of probe hybridization.

The polynucleotide probes of the present invention may range in length from about 15 nucleotides to the full length of the target. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides in length. In some embodiments, the probes are at least 15 nucleotides in length. In some embodiments, the probes are at least 15 nucleotides in length. In some embodiments, the probes are at least 20 nucleotides, at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides, at least 275 nucleotides, at least 300 nucleotides, at least 325 nucleotides, at least 350 nucleotides, at least 375 nucleotides in length. Alternatively, the polynucleotide probes are at least about 400, 450, 500, 550, 600, 650, 700, 750, 800, 850, 900, 950, 1000, 1100, 1200, 1300, or 1400 nucleotides in length.

The polynucleotide probes of a probe set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability. The probe set may comprise a coding target and/or a non-coding target. Preferably, the probe set comprises a combination of a coding target and non-coding target.

The probe set may comprise at least about 5 coding targets and/or non-coding targets. Alternatively, the probe set may comprise at least about 10 coding targets and/or non-coding targets. The probe set may comprise at least about 15 coding targets and/or non-coding targets. In some instances, the probe set may comprise at least about 20 coding targets and/or non-coding targets. Alternatively, the probe set may comprise at least about 30 coding targets and/or non-coding targets. Alternatively, the probe set may comprise at least about 40, 50, 60, 70, 80, 90, 100, 110, 120, 130, 140, or 150 coding targets and/or non-coding targets. In some instances, the coding and/or non-coding targets are selected from a target listed in Table 6. In some instances, the coding and/or non-coding target comprises a sequence selected from Table 7, a sequence that is complementary to a sequence selected from Table 7, or a sequence that is reverse complementary to a sequence selected from Table 7.

The probe set may comprise at least about 20% non-coding targets. In some instances, the probe set comprises at least about 25% non-coding targets. The probe set may comprise at least about 30% non-coding targets. Alternatively, the probe set comprises at least about 35% non-coding targets. In some instances, the probe set comprises at least about 40% non-coding targets. In other instances, the probe set comprises at least about 45% non-coding targets. The probe set may comprise at least about 50% non-coding targets. Alternatively, the probe set comprises at least about 60% non-coding targets. The probe set may comprise at least about 75% non-coding targets. In some instances, the non-coding targets are selected from a target listed in Table 6. In some instances, the non-coding target comprises a sequence selected from Table 7, a sequence that is complementary to a sequence selected from Table 7, or a sequence that is reverse complementary to a sequence selected from Table 7.

The system of the present invention further provides for primers and primer pairs capable of amplifying target sequences defined by the probe set, or fragments or subsequences or complements thereof. The nucleotide sequences of the probe set may be provided in computer-readable media for in silico applications and as a basis for the design of appropriate primers for amplification of one or more target sequences of the probe set.

Primers based on the nucleotide sequences of target sequences can be designed for use in amplification of the target sequences. For use in amplification reactions such as PCR, a pair of primers can be used. The exact composition of the primer sequences is not critical to the invention, but for most applications the primers may hybridize to specific sequences of the probe set under stringent conditions, particularly under conditions of high stringency, as known in the art. The pairs of primers are usually chosen so as to generate an amplification product of at least about 50, 60, 70, 80, 90, or 100 nucleotides in length. Alternatively, the pairs of primers can generate an amplification product of at least 150, 200, 250, 300, 400, 500, 600, 700, 800, 900, or 1000 nucleotides in length. Algorithms for the selection of primer sequences are generally known, and are available in commercial software packages. These primers may be used in standard quantitative or qualitative PCR-based assays to assess transcript expression levels of RNAs defined by the probe set. Alternatively, these primers may be used in combination with probes, such as molecular beacons in amplifications using real-time PCR.

In one embodiment, the primers or primer pairs, when used in an amplification reaction, specifically amplify at least a portion of a target selected from Table 6. In some embodiments, the primers or primer pairs, when used in an amplification reaction, specifically amplify at least a portion of a target comprising a sequence selected from SEQ ID NOs: 1-153, an RNA form thereof, a complement to either thereof, or a reverse complement to either thereof.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific examples of polynucleotide probes or primers useful in this invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary polynucleotide probes or primers having modified oligonucleotide backbones include, for example, those with one or more modified internucleoside linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3' amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene containing backbones; sulphonate backbones; methyleneimino and methylenehydrazino backbones; sulphonate and sulfonamide backbones; amide backbones; and others having mixed N, O, S and $CH_2$ component parts.

The present invention also contemplates oligonucleotide mimetics in which both the sugar and the internucleoside linkage of the nucleotide units are replaced with novel groups. The base units are maintained for hybridization with an appropriate nucleic acid target compound. An example of such an oligonucleotide mimetic is a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza-nitrogen atoms of the amide portion of the backbone.

The present invention also contemplates polynucleotide probes or primers comprising "locked nucleic acids" (LNAs), which may be novel conformationally restricted oligonucleotide analogues containing a methylene bridge that connects the 2'-O of ribose with the 4'-C. LNA and LNA analogues may display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described. Studies of mismatched sequences show that LNA obey the Watson-Crick base pairing rules with generally improved selectivity compared to the corresponding unmodified reference strands.

LNAs may form duplexes with complementary DNA or RNA or with complementary LNA, with high thermal affinities. The universality of LNA-mediated hybridization has been emphasized by the formation of exceedingly stable LNA:LNA duplexes. LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements. In some instances, the primers and/or probes disclosed herein comprise 2'-amino-LNA, 2'-methylamino-LNA, phosphorothioate-LNA, 2'-thio-LNA, or any combination thereof.

Modified polynucleotide probes or primers may also contain one or more substituted sugar moieties. For example, oligonucleotides may comprise sugars with one of the following substituents at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or C2 to $C_{10}$ alkenyl and alkynyl. Examples of such groups are: $O[(CH_2)_n O]_m CH_3$, $O(CH_2)_n OCH_3$, $O(CH_2)_n NH_2$, $O(CH_2)_n CH_3 ONH_2$, and $O(CH_2)_n ON[((CH_2)_n CH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2 CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include T-methoxyethoxy (2'-O—$CH_2 CH_2 OCH_3$, also known as 2'-O-(2-methoxyethyl) or 2'-MOE) [Martin et al., Hely. Chim. Acta, 78:486-504 (1995)], 2'-dimethylaminooxyethoxy ($O(CH2)2 ON(CH_3)_2$ group, also known as 2'-DMA0E), 2'-methoxy (2'-O—$CH_3$), 2'-aminopropoxy (2'-$OCH_2 CH_2 CH_2 NH_2$) and 2'-fluoro (2'-F).

Similar modifications may also be made at other positions on the polynucleotide probes or primers, particularly the 3' position of the sugar on the 3' terminal nucleotide or in 2'-5' linked oligonucleotides and the 5' position of 5' terminal nucleotide. Polynucleotide probes or primers may also have sugar mimetics such as cyclobutyl moieties in place of the pentofuranosyl sugar.

Polynucleotide probes or primers may also include modifications or substitutions to the nucleobase. As used herein, "unmodified" or "natural" nucleobases include the purine bases adenine (A) and guanine (O), and the pyrimidine bases thymine (T), cytosine (C) and uracil (U).

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., *Angewandte*

*Chemie, Int. Ed.*, 30:613 (1991); and Sanghvi, Y. S., (1993) *Antisense Research and Applications*, pp 289-302, Crooke, S. T. and Lebleu, B., ed., CRC Press. Certain of these nucleobases are particularly useful for increasing the binding affinity of the polynucleotide probes of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C.

One skilled in the art recognizes that it is not necessary for all positions in a given polynucleotide probe or primer to be uniformly modified. The present invention, therefore, contemplates the incorporation of more than one of the aforementioned modifications into a single polynucleotide probe or even at a single nucleoside within the probe or primer.

One skilled in the art also appreciates that the nucleotide sequence of the entire length of the polynucleotide probe or primer does not need to be derived from the target sequence. Thus, for example, the polynucleotide probe may comprise nucleotide sequences at the 5' and/or 3' termini that are not derived from the target sequences. Nucleotide sequences which are not derived from the nucleotide sequence of the target sequence may provide additional functionality to the polynucleotide probe. For example, they may provide a restriction enzyme recognition sequence or a "tag" that facilitates detection, isolation, purification or immobilization onto a solid support. Alternatively, the additional nucleotides may provide a self-complementary sequence that allows the primer/probe to adopt a hairpin configuration. Such configurations are necessary for certain probes, for example, molecular beacon and Scorpion probes, which can be used in solution hybridization techniques.

The polynucleotide probes or primers can incorporate moieties useful in detection, isolation, purification, or immobilization, if desired. Such moieties are well-known in the art (see, for example, Ausubel et al., (1997 & updates) *Current Protocols in Molecular Biology*, Wiley & Sons, New York) and are chosen such that the ability of the probe to hybridize with its target sequence is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the invention. A variety of different coding schemes are known in the art, including fluorophores, including SCNCs, deposited metals, and RF tags.

Polynucleotides from the described target sequences may be employed as probes for detecting target sequences expression, for ligation amplification schemes, or may be used as primers for amplification schemes of all or a portion of a target sequences. When amplified, either strand produced by amplification may be provided in purified and/or isolated form.

In one embodiment, polynucleotides of the invention comprise (a) a nucleic acid depicted in Table 7; (b) an RNA form of any one of the nucleic acids depicted in Table 7; (c) a peptide nucleic acid form of any of the nucleic acids depicted in Table 7; (d) a nucleic acid comprising at least 20 consecutive bases of any of (a-c); (e) a nucleic acid comprising at least 25 bases having at least 80% sequenced identity to any of (a-c); (f) a complement to any of (a-e), or (g) a reverse complement of any of (a-e).

Complements may take any polymeric form capable of base pairing to the species recited in (a)-(e), including nucleic acid such as RNA or DNA, or may be a neutral polymer such as a peptide nucleic acid. Polynucleotides of the invention can be selected from the subsets of the recited nucleic acids described herein, as well as their complements.

In some embodiments, polynucleotides of the invention comprise at least 20 consecutive bases of the nucleic acids as depicted in Table 7 or a complement thereto. The polynucleotides may comprise at least 21, 22, 23, 24, 25, 27, 30, 32, 35 or more consecutive bases of the nucleic acids as depicted in Table 7, as applicable.

The polynucleotides may be provided in a variety of formats, including as solids, in solution, or in an array. The polynucleotides may optionally comprise one or more labels, which may be chemically and/or enzymatically incorporated into the polynucleotide.

In one embodiment, solutions comprising polynucleotide and a solvent are also provided. In some embodiments, the solvent may be water or may be predominantly aqueous. In some embodiments, the solution may comprise at least two, three, four, five, six, seven, eight, nine, ten, twelve, fifteen, seventeen, twenty or more different polynucleotides, including primers and primer pairs, of the invention. Additional substances may be included in the solution, alone or in combination, including one or more labels, additional solvents, buffers, biomolecules, polynucleotides, and one or more enzymes useful for performing methods described herein, including polymerases and ligases. The solution may further comprise a primer or primer pair capable of amplifying a polynucleotide of the invention present in the solution.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), polyethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and include semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Preparation of Probes and Primers

The polynucleotide probes or primers of the present invention can be prepared by conventional techniques well-known to those skilled in the art. For example, the polynucleotide probes can be prepared using solid-phase synthesis using commercially available equipment. As is well-known in the art, modified oligonucleotides can also be readily prepared by similar methods. The polynucleotide probes can also be synthesized directly on a solid support according to methods standard in the art. This method of synthesizing polynucleotides is particularly useful when the polynucleotide probes are part of a nucleic acid array.

Polynucleotide probes or primers can be fabricated on or attached to the substrate by any suitable method, for example the methods described in U.S. Pat. No. 5,143,854, PCT Publ. No WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261. Still further techniques include bead based techniques such as those described in PCT Appl. No. PCT/US93/04145 and pin based methods such as those described in U.S. Pat. No. 5,288,514. Additional flow channel or spotting methods applicable to attachment of sensor polynucleotides to a substrate are described in U.S. patent application Ser. No. 07/980,523, filed Nov. 20, 1992, and U.S. Pat. No. 5,384,261.

Alternatively, the polynucleotide probes of the present invention can be prepared by enzymatic digestion of the naturally occurring target gene, or mRNA or cDNA derived therefrom, by methods known in the art.

Samples

Samples for use with the systems and in the methods of the present invention comprise nucleic acids (e.g., DNA, RNA) or peptides suitable for providing expression information. In some instances, the sample is any material suspected of comprising cancer tissue or cells. The sample can be a biological sample used directly in a method of the invention. Alternatively, the sample can be a sample prepared from a biological sample.

In one embodiment, the sample or portion of the sample comprising or suspected of comprising cancer tissue or cells can be any source of biological material, including cells, tissue or fluid, including bodily fluids (e.g., blood, sweat, tears, saliva, urine, vaginal secretion, sperm, cerebral spinal fluid, spinal fluid). Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods.

One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gef™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

The samples can be obtained at any time. In some instances, multiple samples are obtained from the subject. In some instances, the samples are obtained prior to diagnosis, after diagnosis, prior to prognosis, after prognosis, prior to administration of a therapeutic regimen, during administration of a therapeutic regimen, after administration of a therapeutic regimen, prior to modification of a therapeutic regimen, during modification of a therapeutic regimen, after modification of a therapeutic regimen, or a combination thereof. In some instances, the samples are obtained 1, 2, 3, 4, 5, 6, 7, 8, 9, 10, 11, 12, 13, or 14 days; 1, 2, 3, 4, 5, 6, 7, 8, 9, 10, 11, 12, 13, or 14 weeks; 1, 2, 3, 4, 5, 6, 7, 8, 9, 10, 11, 12, 13, or 14 months; or 1, 2, 3, 4, 5, 6, 7, 8, 9, 10, 11, 12, 13, or 14 years prior to diagnosis, after diagnosis, prior to prognosis, after prognosis, prior to administration of a therapeutic regimen, during administration of a therapeutic regimen, after administration of a therapeutic regimen, prior to modification of a therapeutic regimen, during modification of a therapeutic regimen, after modification of a therapeutic regimen, or a combination thereof. In some instances, the samples are obtained about every 1, 2, 3, 4, 5, 6, 7, 8, 9, 10, 11, 12, 13, or 14 days; 1, 2, 3, 4, 5, 6, 7, 8, 9, 10, 11, 12, 13, or 14 weeks; 1, 2, 3, 4, 5, 6, 7, 8, 9, 10, 11, 12, 13, or 14 months; or 1, 2, 3, 4, 5, 6, 7, 8, 9, 10, 11, 12, 13, or 14 years prior to diagnosis, after diagnosis, prior to prognosis, after prognosis, prior to administration of a therapeutic regimen, during administration of a therapeutic regimen, after administration of a therapeutic regimen, prior to modification of a therapeutic regimen, during modification of a therapeutic regimen, after modification of a therapeutic regimen, or a combination thereof. In some instances, two or more samples are obtained from the subject. In some instances, three or more samples are obtained from the subject. In some instances, four or more samples are obtained from the subject. In some instances, five or more samples are obtained from the subject. In some instances, at least 6, 7, 8, 9, 10, 11, 12, 13, 14, 15, 20, 25, 30, 35, 40, 45, 50, 55, 60, 70, 80, 90, or 100 samples are obtained from the subject.

DNA and RNA Extraction

DNA can be extracted and purified from biological samples using any suitable technique. A number of techniques for DNA extraction and/or purification are known in the art, and several are commercially available (e.g., ChargeSwitch®, MELT™ total nucleic acid isolation system, MagMAX™ FFPE total nucleic acid isolation kit, MagMAX™ total nucleic acid isolation kit, QIAamp DNA kit, Omni-Pure™ genomic DNA purification system, WaterMaster™ DNA purification kit). Reagents such as DNAzol® and TR1 Reagent® can also be used to extract and/or purify DNA. DNA can be further purified using Proteinase K and/or RNAse.

RNA can be extracted and purified from biological samples using any suitable technique. A number of techniques are known in the art, and several are commercially available (e.g., FormaPure nucleic acid extraction kit, Agencourt Biosciences, Beverly Mass., High Pure FFPE RNA Micro Kit, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

DNA and/or RNA concentrations can be made using a Nanodrop ND-1000 spectrophotometer (Nanodrop Technologies, Rockland, Del.). DNA and/or RNA can be extracted from frozen tissues, whole blood, hair, sperm, bones, nails, tissues, blood stains, saliva, buccal (cheek) swabs, epithelial cells, and urine.

Kits

Kits for performing the desired method(s) are also provided. In some instances, the kit comprises a container or housing for holding the components of the kit, one or more vessels containing one or more nucleic acid(s), and optionally one or more vessels containing one or more reagents. The reagents include those described herein, and those reagents useful for performing the methods described herein, including amplification reagents, purification reagents, binding reagents, and may include one or more probe sets, probes, primers or primer pairs, enzymes (including polymerases and ligases), intercalating dyes, labeled probes, labels that can be incorporated into amplification products, and labels that can be attached or hybridized to a target or probe disclosed herein.

In some embodiments, the kit comprises primers or primer pairs specific for those subsets and combinations of target sequences described herein. In some instances, the kit comprises at least two, three, four or five primers or pairs of primers suitable for isolating, amplifying, hybridizing, sequencing, and/or quantifying one or more targets disclosed herein. In some embodiments, the kit comprises from five to fifty primers or pairs of primers suitable for isolating, amplifying, hybridizing, sequencing, and/or quantifying one or more targets disclosed herein. In some embodiments, the kit comprises at least 10, 15, 20, 25, 30, 35, 40, 45, 50, 55, 60, 65, 70, 75, 80, 85, 90, 95, 100, 110, 120, 130, 140, or 150 primers or pairs of primers suitable for isolating, amplifying, hybridizing, sequencing, and/or quantifying one or more targets disclosed herein.

The reagents may independently be in liquid or solid form. The reagents may be provided in mixtures. Control samples and/or nucleic acids may optionally be provided in the kit. Control samples may include tissue and/or nucleic acids obtained from or representative of tumor samples from patients showing no evidence of disease, as well as tissue and/or nucleic acids obtained from or representative of tumor samples from patients that develop systemic cancer.

The probe sets, probes, primers or primer pairs may be provided in an array format, and thus an array or microarray may be included in the kit. The kit optionally may be certified by a government agency for use in prognosing the disease outcome of cancer patients and/or for designating a treatment modality.

In some instances, the probe sets, probes, primers or primer pairs are attached to a solid support. A solid support comprises any solid platform to which a probe set, probe, primer, or primer pair can be attached. Examples of solid supports include, but are not limited to, beads, plates, multiwall plates, CPG particles, or MPPS materials. In some instances, the bead is a streptavidin bead, agarose bead, magnetic bead, Dynabeads®, MACS® microbead, antibody conjugated bead (e.g., anti-immunoglobulin microbead), protein A conjugated bead, protein G conjugated bead, protein A/G conjugated bead, protein L conjugated bead, oligo-dT conjugated bead, silica bead, silica-like bead, anti-biotin microbead, anti-fluorochrome microbead, or BcMag™ Carboxy-Terminated Magnetic Bead. In some instances, the plate is a MSD multi-array plate, MSD Multi-Spot® plate, microplate, ProteOn microplate, AlphaPlate, DELFIA plate, IsoPlate, or LumaPlate. In some instances, the CPG material has a pore size of 500, 1000, 1500, 2000, or 3000 Å. In some instances, the solid support is porous. In some instances, the solid support is macroporous.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Devices

Devices useful for performing methods of the invention are also provided. The devices can comprise means for characterizing the expression level of a target sequence of the invention, for example components for performing one or more methods of nucleic acid extraction, amplification, and/or detection. Such components may include one or more of an amplification chamber (for example a thermal cycler), a plate reader, a spectrophotometer, luminometer, fluorometer, electrophoresis apparatus, capillary electrophoresis apparatus, chip reader, plate reader, microarray reader, computer, and or robotic sample handling components. These components ultimately can obtain data that reflects the expression level of the target sequences used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection component.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the expression levels of the target sequences being studied with a prognosis of disease outcome. Such means may comprise one or more of a variety of correlative techniques, including lookup tables, algorithms, multivariate models, and linear or nonlinear combinations of expression models or algorithms. The expression levels may be converted to one or more likelihood scores, reflecting a likelihood that the patient providing the sample may exhibit a particular disease outcome. The models and/or algorithms can be provided in machine readable format and can optionally further designate a treatment modality for a patient or class of patients.

The device also comprises output means for outputting the disease status, prognosis and/or a treatment modality. Such output means can take any form which transmits the results to a patient and/or a healthcare provider, and may include a monitor, a printed format, or both. The device may use a computer system for performing one or more of the steps provided.

The methods disclosed herein may also comprise the transmission of data/information. For example, data/information derived from the detection and/or quantification of the target may be transmitted to another device and/or instrument. In some instances, the information obtained from an algorithm may also be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc).

Transmission of the data/information may comprise digital transmission or analog transmission. Digital transmission may comprise the physical transfer of data (a digital bit stream) over a point-to-point or point-to-multipoint communication channel. Examples of such channels are copper wires, optical fibres, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

Amplification and Hybridization

Following sample collection and nucleic acid extraction, the nucleic acid portion of the sample that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid (e.g., RNA, DNA). In some instances, the nucleic acid is an expressed RNA. An amplification product can be RNA or DNA, and may include a complementary strand to the target sequence. In some instances, DNA amplification products are produced initially through reverse transcription and then optionally from further amplification reactions. The amplification product may include all or a portion of a target sequence, and may optionally be labeled. A variety of amplification methods are suitable for use, including polymerase-based methods and ligation-based methods. Exemplary amplification techniques include the polymerase chain reaction method (PCR), the lipase chain reaction (LCR), rolling circle amplification, ribozyme-based methods, self sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the target sequence that is used for detection as the target polynucleotide. In some cases, the presence and/or amount of the amplification product itself may be used to determine the expression level of a given target sequence. In other instances, the amplification product may be used to hybridize to an array or other substrate comprising sensor polynucleotides which are used to detect and/or quantitate target sequence expression.

The first cycle of amplification in polymerase-based methods typically forms a primer extension product complementary to the template strand. If the template is single-stranded. RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that can produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2M T7, Tub, Taq, Tth, Pfic, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases.

Exemplary thermostable polymerases include Tub, Taq, Tth, Pfic, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WT-Ovation™ System, WT-Ovation™ System v2, WT-Ovation™ Pico System, WT-Ovation'm FFPE Exon Module, WT-Ovation™ FFPE Exon Module RiboAmp and RiboAmp$^{Plus}$ RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination. Amplified nucleic acids may be subjected to one or more purification reactions after amplification and labeling, for example using magnetic beads (e.g., RNAClean magnetic beads, Agencourt Biosciences).

Multiple biomarkers (e.g., targets) can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXper® Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.).

Detection and/or Quantification of Target Sequences

Any method of detecting and/or quantitating the expression of the encoded target sequences can in principle be used in the invention. The target sequences can be directly detected and/or quantitated, or may be copied and/or amplified to allow detection of amplified copies of the expressed target sequences or its complement.

Methods for detecting and/or quantifying a target can include Northern blotting, sequencing, array or microarray hybridization, by enzymatic cleavage of specific structures (e.g., an Invader® assay, Third Wave Technologies, e.g. as described in U.S. Pat. Nos. 5,846,717, 6,090,543; 6,001,567; 5,985,557; and 5,994,069) and amplification methods, e.g. RT-PCR, including in a TaqMan® assay (PE Biosystems, Foster City, Calif., e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis.

In some instances, target sequences may be detected by sequencing. Sequencing methods may comprise whole genome sequencing or exome sequencing. Sequencing methods such as Maxim-Gilbert, chain-termination, or high-throughput systems may also be used. Additional, suitable sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, and SOLiD sequencing.

Additional methods for detecting and/or quantifying a target sequence include single-molecule sequencing (e.g., Illumina, Helicos, PacBio, ABI SOLID), in situ hybridization, bead-array technologies (e.g., Luminex xMAP, Illumina BeadChips), branched DNA technology (e.g., Panomics, Genisphere).

Reverse Transcription for QRT-PCR Analysis

Reverse transcription can be performed by any method known in the art. For example, reverse transcription may be performed using the Omniscript kit (Qiagen, Valencia, Calif.), Superscript III kit (Invitrogen, Carlsbad, Calif.), for RT-PCR. Target-specific priming can be performed in order to increase the sensitivity of detection of target sequences and generate target-specific cDNA.

TaqMan® Gene Expression Analysis

TaqMan®RT-PCR can be performed using Applied Biosystems Prism (ABI) 7900 HT instruments in a 5 1.11 volume with target sequence-specific cDNA equivalent to 1 ng total RNA.

Primers and probes concentrations for TaqMan analysis are added to amplify fluorescent amplicons using PCR cycling conditions such as 95° C. for 10 minutes for one cycle, 95° C. for 20 seconds, and 60° C. for 45 seconds for 40 cycles. A reference sample can be assayed to ensure reagent and process stability. Negative controls (e.g., no template) should be assayed to monitor any exogenous nucleic acid contamination.

Classification Arrays

In some instances, a probe set or probes derived herein is provided in an array format. In some instances, an "array" is a spatially or logically organized collection of polynucleotide probes. An array comprising probes specific for a coding target, non-coding target, or a combination thereof may be used. Alternatively, an array comprising probes specific for two or more of transcripts listed in Table 7, an RNA form thereof, a product derived therefrom, a complement thereof, or a reverse complement thereof. In some instances, an array is specific for 5, 10, 15, 20, 25, 30, 50, 75, 100, 150 or more of transcripts listed in Table 7, an RNA form thereof, a product derived therefrom, a complement thereof, or a reverse complement thereof. Alternatively, an array comprising probes specific for two or more of the targets listed in Table 6. In some instances, an array is specific for 5, 10, 15, 20, 25, 30, 50, 75, 100, 150 or more of the targets listed in Table 6. In some instances, expression of these target sequences or targets are detected alone or in combination with other transcripts or targets. Examples of other transcripts or targets include, but are not limited to, any of the transcripts and/or targets disclosed in U.S. patent application Ser. Nos. 13/254,571 and 13/258,429. In some embodiments, an array is used which comprises a wide range of sensor probes for prostate-specific expression products, along with appropriate control sequences. In some instances, the array may comprise the Human Exon 1.0 ST Array (HuEx 1.0 ST, Affymetrix, Inc., Santa Clara, Calif.).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that may be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment, the array is a chip.

Data Analysis

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (e.g., an 'expression signature') and converted into a likelihood score. This likelihood score indicates the probability that a biological sample is from a patient who may exhibit no evidence of disease, who may exhibit systemic cancer, or who may exhibit biochemical recurrence. The likelihood score can be used to distinguish these disease states. The models and/or algorithms can be provided in machine readable format, and may be used to correlate expression levels or an expression profile with a disease state, and/or to designate a treatment modality for a patient or class of patients.

In some instances, assaying the expression level for a plurality of targets comprises the use of an algorithm or classifier. Array data can be managed, classified, and analyzed using techniques known in the art. Assaying the expression level for a plurality of targets can comprise probe set modeling and/or data pre-processing. Probe set modeling and/or data pre-processing can be derived using the Robust Multi-Array (RMA) algorithm or variants GC-RMA, fRMA, Probe Logarithmic Intensity Error (PLIER) algorithm or variant IterPLIER. Variance or intensity filters can be applied to pre-process data using the RMA algorithm, for example by removing target sequences with a standard deviation of <10 or a mean intensity of <100 intensity units of a normalized data range, respectively.

Alternatively, assaying the expression level for a plurality of targets may comprise the use of a machine learning algorithm. The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include Artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriofi algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, Temporal difference learning, Q-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

Additional Techniques and Tests

Factors known in the art for diagnosing and/or suggesting, selecting, designating, recommending or otherwise determining a course of treatment for a patient or class of patients suspected of having cancer can be employed in combination with measurements of the target sequence expression. The methods disclosed herein may include additional techniques such as cytology, histology, ultrasound analysis, MRI results, CT scan results, and measurements of PSA levels.

Certified tests for classifying disease status and/or designating treatment modalities may also be used in diagnosing, predicting, and/or monitoring the status or outcome of a cancer in a subject. A certified test may comprise a means for characterizing the expression levels of one or more of the target sequences of interest, and a certification from a government regulatory agency endorsing use of the test for classifying the disease status of a biological sample.

In some embodiments, the certified test may comprise reagents for amplification reactions used to detect and/or quantitate expression of the target sequences to be characterized in the test. An array of probe nucleic acids can be used, with or without prior target amplification, for use in measuring target sequence expression.

The test is submitted to an agency having authority to certify the test for use in distinguishing disease status and/or outcome. Results of detection of expression levels of the target sequences used in the test and correlation with disease status and/or outcome are submitted to the agency. A certification authorizing the diagnostic and/or prognostic use of the test is obtained.

Also provided are portfolios of expression levels comprising a plurality of normalized expression levels of the target sequences described Table 6. Such portfolios may be provided by performing the methods described herein to obtain expression levels from an individual patient or from a group of patients. The expression levels can be normalized by any method known in the art; exemplary normalization methods that can be used in various embodiments include Robust Multichip Average (RMA), probe logarithmic intensity error estimation (PLIER), non-linear fit (NLFIT) quantile-based and nonlinear normalization, and combinations thereof. Background correction can also be performed on the expression data; exemplary techniques useful for background correction include mode of intensities, normalized using median polish probe modeling and sketch-normalization.

In some embodiments, portfolios are established such that the combination of genes in the portfolio exhibit improved sensitivity and specificity relative to known methods. In considering a group of genes for inclusion in a portfolio, a small standard deviation in expression measurements correlates with greater specificity. Other measurements of variation such as correlation coefficients can also be used in this capacity. The invention also encompasses the above methods where the expression level determines the status or outcome of a cancer in the subject with at least about 45% specificity. In some embodiments, the expression level determines the status or outcome of a cancer in the subject with at least about 50% specificity. In some embodiments, the expression level determines the status or outcome of a cancer in the subject with at least about 55% specificity. In some embodiments, the expression level determines the status or outcome of a cancer in the subject with at least about 60% specificity. In some embodiments, the expression level determines the status or outcome of a cancer in the subject with at least about 65% specificity. In some embodiments, the expression level determines the status or outcome of a cancer in the subject with at least about 70% specificity. In some embodiments, the expression level determines the status or outcome of a cancer in the subject with at least about 75% specificity. In some embodiments, the expression level determines the status or outcome of a cancer in the subject with at least about 80% specificity. In some embodiments, t the expression level determines the status or outcome of a cancer in the subject with at least about 85% specificity. In some embodiments, the expression level determines the status or outcome of a cancer in the subject with at least about 90% specificity. In some embodiments, the expression level determines the status or outcome of a cancer in the subject with at least about 95% specificity.

The invention also encompasses the any of the methods disclosed herein where the accuracy of diagnosing, monitoring, and/or predicting a status or outcome of a cancer is at least about 45%. In some embodiments, the accuracy of diagnosing, monitoring, and/or predicting a status or outcome of a cancer is at least about 50%. In some embodiments, the accuracy of diagnosing, monitoring, and/or predicting a status or outcome of a cancer is at least about 55%. In some embodiments, the accuracy of diagnosing, monitoring, and/or predicting a status or outcome of a cancer is at least about 60%. In some embodiments, the accuracy of diagnosing, monitoring, and/or predicting a status or outcome of a cancer is at least about 65%. In some embodiments, the accuracy of diagnosing, monitoring, and/or predicting a status or outcome of a cancer is at least about 70%. In some embodiments, the accuracy of diagnosing, monitoring, and/or predicting a status or outcome of a cancer is at least about 75%. In some embodiments, the accuracy of diagnosing, monitoring, and/or predicting a status or outcome of a cancer is at least about 80%. In some embodiments, the accuracy of diagnosing, monitoring, and/or predicting a status or outcome of a cancer is at least about 85%. In some embodiments, the accuracy of diagnosing, monitoring, and/or predicting a status or outcome of a cancer is at least about 90%. In some embodiments, the accuracy of diagnosing, monitoring, and/or predicting a status or outcome of a cancer is at least about 95%.

The invention also encompasses the any of the methods disclosed herein where the sensitivity is at least about 45%. In some embodiments, the sensitivity is at least about 50%. In some embodiments, the sensitivity is at least about 55%. In some embodiments, the sensitivity is at least about 60%. In some embodiments, the sensitivity is at least about 65%. In some embodiments, the sensitivity is at least about 70%. In some embodiments, the sensitivity is at least about 75%. In some embodiments, the sensitivity is at least about 80%. In some embodiments, the sensitivity is at least about 85%. In some embodiments, the sensitivity is at least about 90%. In some embodiments, the sensitivity is at least about 95%.

In some instances, the methods disclosed herein may comprise the use of a genomic-clinical classifier (GCC) model. A general method for developing a GCC model may comprise (a) providing a sample from a subject suffering from a cancer; (b) assaying the expression level for a plurality of targets; (c) generating a model by using a machine learning algorithm. In some instances, the machine learning algorithm comprises Random Forests.

Cancer

The systems, compositions and methods disclosed herein may be used to diagnosis, monitor and/or predict the status or outcome of a cancer. Generally, a cancer is characterized by the uncontrolled growth of abnormal cells anywhere in a body. The abnormal cells may be termed cancer cells, malignant cells, or tumor cells. Many cancers and the abnormal cells that compose the cancer tissue are further identified by the name of the tissue that the abnormal cells originated from (for example, breast cancer, lung cancer, colon cancer, prostate cancer, pancreatic cancer, thyroid cancer). Cancer is not confined to humans; animals and other living organisms can get cancer.

In some instances, the cancer may be malignant. Alternatively, the cancer may be benign. The cancer may be a recurrent and/or refractory cancer. Most cancers can be classified as a carcinoma, sarcoma, leukemia, lymphoma, myeloma, or a central nervous system cancer.

The cancer may be a sarcoma. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hem angiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Alternatively, the cancer may be a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. Preferably, the cancer is a prostate cancer. Alternatively, the cancer may be a thyroid cancer, bladder cancer, or pancreatic cancer.

In some instances, the cancer is a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The cancer may be a leukemia. The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic-leukemia.

In some instances, the cancer is a lymphoma. Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Cancer Staging

Diagnosing, predicting, or monitoring a status or outcome of a cancer may comprise determining the stage of the cancer. Generally, the stage of a cancer is a description (usually numbers I to IV with IV having more progression) of the extent the cancer has spread. The stage often takes into account the size of a tumor, how deeply it has penetrated, whether it has invaded adjacent organs, how many lymph nodes it has metastasized to (if any), and whether it has spread to distant organs. Staging of cancer can be used as a predictor of survival, and cancer treatment may be determined by staging. Determining the stage of the cancer may occur before, during, or after treatment. The stage of the cancer may also be determined at the time of diagnosis.

Cancer staging can be divided into a clinical stage and a pathologic stage. Cancer staging may comprise the TNM classification. Generally, the TNM Classification of Malignant Tumours (TNM) is a cancer staging system that describes the extent of cancer in a patient's body. T may describe the size of the tumor and whether it has invaded nearby tissue, N may describe regional lymph nodes that are involved, and M may describe distant metastasis (spread of cancer from one body part to another). In the TNM (Tumor, Node, Metastasis) system, clinical stage and pathologic stage are denoted by a small "c" or "p" before the stage (e.g., cT3N1M0 or pT2N0).

Often, clinical stage and pathologic stage may differ. Clinical stage may be based on all of the available information obtained before a surgery to remove the tumor. Thus, it may include information about the tumor obtained by physical examination, radiologic examination, and endoscopy. Pathologic stage can add additional information gained by examination of the tumor microscopically by a pathologist. Pathologic staging can allow direct examination of the tumor and its spread, contrasted with clinical staging which may be limited by the fact that the information is obtained by making indirect observations at a tumor which is still in the body. The TNM staging system can be used for most forms of cancer.

Alternatively, staging may comprise Ann Arbor staging. Generally, Ann Arbor staging is the staging system for lymphomas, both in Hodgkin's lymphoma (previously called Hodgkin's disease) and Non-Hodgkin lymphoma (abbreviated NHL). The stage may depend on both the place where the malignant tissue is located (as located with biopsy, CT scanning and increasingly positron emission tomography) and on systemic symptoms due to the lymphoma ("B symptoms": night sweats, weight loss of >10% or fevers). The principal stage may be determined by location of the tumor. Stage I may indicate that the cancer is located in a single region, usually one lymph node and the surrounding area. Stage I often may not have outward symptoms. Stage II can indicate that the cancer is located in two separate regions, an affected lymph node or organ and a second affected area, and that both affected areas are confined to one side of the diaphragm—that is, both are above the diaphragm, or both are below the diaphragm. Stage III often indicates that the cancer has spread to both sides of the diaphragm, including one organ or area near the lymph nodes or the spleen. Stage IV may indicate diffuse or disseminated involvement of one or more extralymphatic organs, including any involvement of the liver, bone marrow, or nodular involvement of the lungs.

Modifiers may also be appended to some stages. For example, the letters A, B, E, X, or S can be appended to some stages. Generally, A or B may indicate the absence of constitutional (B-type) symptoms is denoted by adding an "A" to the stage; the presence is denoted by adding a "B" to the stage. E can be used if the disease is "extranodal" (not in the lymph nodes) or has spread from lymph nodes to adjacent tissue. X is often used if the largest deposit is >10 cm large ("bulky disease"), or whether the mediastinum is wider than ⅓ of the chest on a chest X-ray. S may be used if the disease has spread to the spleen.

The nature of the staging may be expressed with CS or PS. CS may denote that the clinical stage as obtained by doctor's examinations and tests. PS may denote that the pathological stage as obtained by exploratory laparotomy (surgery performed through an abdominal incision) with splenectomy (surgical removal of the spleen).

Therapeutic Regimens

Diagnosing, predicting, or monitoring a status or outcome of a cancer may comprise treating a cancer or preventing a cancer progression. In addition, diagnosing, predicting, or monitoring a status or outcome of a cancer may comprise identifying or predicting responders to an anticancer therapy. In some instances, diagnosing, predicting, or monitoring may comprise determining a therapeutic regimen. Determining a therapeutic regimen may comprise administering an anti-cancer therapy. Alternatively, determining a therapeutic regimen may comprise modifying, recommending, continuing or discontinuing an anti-cancer regimen. In some instances, if the sample expression patterns are consistent with the expression pattern for a known disease or disease outcome, the expression patterns can be used to designate one or more treatment modalities (e.g., therapeutic regimens, anti-cancer regimen). An anti-cancer regimen may comprise one or more anti-cancer therapies. Examples of anti-cancer therapies include surgery, chemotherapy, radiation therapy, immunotherapy/biological therapy, photodynamic therapy.

Surgical oncology uses surgical methods to diagnose, stage, and treat cancer, and to relieve certain cancer-related symptoms. Surgery may be used to remove the tumor (e.g., excisions, resections, debulking surgery), reconstruct a part of the body (e.g., restorative surgery), and/or to relieve symptoms such as pain (e.g., palliative surgery). Surgery may also include cryosurgery. Cryosurgery (also called cryotherapy) may use extreme cold produced by liquid nitrogen (or argon gas) to destroy abnormal tissue. Cryosurgery can be used to treat external tumors, such as those on the skin. For external tumors, liquid nitrogen can be applied directly to the cancer cells with a cotton swab or spraying device. Cryosurgery may also be used to treat tumors inside the body (internal tumors and tumors in the bone). For internal tumors, liquid nitrogen or argon gas may be circulated through a hollow instrument called a cryoprobe, which is placed in contact with the tumor. An ultrasound or MRI may be used to guide the cryoprobe and monitor the freezing of the cells, thus limiting damage to nearby healthy tissue. A ball of ice crystals may form around the probe, freezing nearby cells. Sometimes more than one probe is used to deliver the liquid nitrogen to various parts of the tumor. The probes may be put into the tumor during surgery or through the skin (percutaneously). After cryosurgery, the frozen tissue thaws and may be naturally absorbed by the body (for internal tumors), or may dissolve and form a scab (for external tumors).

Chemotherapeutic agents may also be used for the treatment of cancer. Examples of chemotherapeutic agents include alkylating agents, anti-metabolites, plant alkaloids and terpenoids, vinca alkaloids, podophyllotoxin, taxanes, topoisomerase inhibitors, and cytotoxic antibiotics. Cisplatin, carboplatin, and oxaliplatin are examples of alkylating agents. Other alkylating agents include mechlorethamine, cyclophosphamide, chlorambucil, ifosfamide. Alkylating agents may impair cell function by forming covalent bonds with the amino, carboxyl, sulfhydryl, and phosphate groups in biologically important molecules. Alternatively, alkylating agents may chemically modify a cell's DNA.

Anti-metabolites are another example of chemotherapeutic agents. Anti-metabolites may masquerade as purines or pyrimidines and may prevent purines and pyrimidines from becoming incorporated in to DNA during the "S" phase (of the cell cycle), thereby stopping normal development and division. Antimetabolites may also affect RNA synthesis. Examples of metabolites include azathioprine and mercaptopurine.

Alkaloids may be derived from plants and block cell division may also be used for the treatment of cancer. Alkyloids may prevent microtubule function. Examples of alkaloids are vinca alkaloids and taxanes. Vinca alkaloids may bind to specific sites on tubulin and inhibit the assembly of tubulin into microtubules (M phase of the cell cycle). The vinca alkaloids may be derived from the Madagascar periwinkle, *Catharanthus roseus* (formerly known as *Vinca rosea*). Examples of vinca alkaloids include, but are not limited to, vincristine, vinblastine, vinorelbine, or vindesine. Taxanes are diterpenes produced by the plants of the genus *Taxus* (yews). Taxanes may be derived from natural sources or synthesized artificially. Taxanes include paclitaxel (Taxol) and docetaxel (Taxotere). Taxanes may disrupt microtubule function. Microtubules are essential to cell division, and taxanes may stabilize GDP-bound tubulin in the microtubule, thereby inhibiting the process of cell division. Thus, in essence, taxanes may be mitotic inhibitors. Taxanes may also be radiosensitizing and often contain numerous chiral centers.

Alternative chemotherapeutic agents include podophyllotoxin. Podophyllotoxin is a plant-derived compound that may help with digestion and may be used to produce cytostatic drugs such as etoposide and teniposide. They may prevent the cell from entering the G1 phase (the start of DNA replication) and the replication of DNA (the S phase).

Topoisomerases are essential enzymes that maintain the topology of DNA. Inhibition of type I or type II topoisomerases may interfere with both transcription and replication of DNA by upsetting proper DNA supercoiling. Some chemotherapeutic agents may inhibit topoisomerases. For example, some type I topoisomerase inhibitors include camptothecins: irinotecan and topotecan. Examples of type II inhibitors include amsacrine, etoposide, etoposide phosphate, and teniposide.

Another example of chemotherapeutic agents is cytotoxic antibiotics. Cytotoxic antibiotics are a group of antibiotics that are used for the treatment of cancer because they may interfere with DNA replication and/or protein synthesis. Cytotoxic antibiotics include, but are not limited to, actinomycin, anthracyclines, doxorubicin, daunorubicin, valrubicin, idarubicin, epirubicin, bleomycin, plicamycin, and mitomycin.

In some instances, the anti-cancer treatment may comprise radiation therapy. Radiation can come from a machine outside the body (external-beam radiation therapy) or from radioactive material placed in the body near cancer cells (internal radiation therapy, more commonly called brachytherapy). Systemic radiation therapy uses a radioactive substance, given by mouth or into a vein that travels in the blood to tissues throughout the body.

External-beam radiation therapy may be delivered in the form of photon beams (either x-rays or gamma rays). A photon is the basic unit of light and other forms of electromagnetic radiation. An example of external-beam radiation therapy is called 3-dimensional conformal radiation therapy (3D-CRT). 3D-CRT may use computer software and advanced treatment machines to deliver radiation to very precisely shaped target areas. Many other methods of external-beam radiation therapy are currently being tested and used in cancer treatment. These methods include, but are not limited to, intensity-modulated radiation therapy (IMRT), image-guided radiation therapy (IGRT), Stereotactic radiosurgery (SRS), Stereotactic body radiation therapy (SBRT), and proton therapy.

Intensity-modulated radiation therapy (IMRT) is an example of external-beam radiation and may use hundreds of tiny radiation beam-shaping devices, called collimators, to deliver a single dose of radiation. The collimators can be stationary or can move during treatment, allowing the intensity of the radiation beams to change during treatment sessions. This kind of dose modulation allows different areas of a tumor or nearby tissues to receive different doses of radiation. IMRT is planned in reverse (called inverse treatment planning). In inverse treatment planning, the radiation doses to different areas of the tumor and surrounding tissue are planned in advance, and then a high-powered computer program calculates the required number of beams and angles of the radiation treatment. In contrast, during traditional (forward) treatment planning, the number and angles of the radiation beams are chosen in advance and computers calculate how much dose may be delivered from each of the planned beams. The goal of IMRT is to increase the radiation dose to the areas that need it and reduce radiation exposure to specific sensitive areas of surrounding normal tissue.

Another example of external-beam radiation is image-guided radiation therapy (IGRT). In IGRT, repeated imaging scans (CT, MRI, or PET) may be performed during treatment. These imaging scans may be processed by computers to identify changes in a tumor's size and location due to treatment and to allow the position of the patient or the planned radiation dose to be adjusted during treatment as needed. Repeated imaging can increase the accuracy of radiation treatment and may allow reductions in the planned volume of tissue to be treated, thereby decreasing the total radiation dose to normal tissue.

Tomotherapy is a type of image-guided IMRT. A tomotherapy machine is a hybrid between a CT imaging scanner and an external-beam radiation therapy machine. The part of the tomotherapy machine that delivers radiation for both imaging and treatment can rotate completely around the patient in the same manner as a normal CT scanner. Tomotherapy machines can capture CT images of the patient's tumor immediately before treatment sessions, to allow for very precise tumor targeting and sparing of normal tissue.

Stereotactic radiosurgery (SRS) can deliver one or more high doses of radiation to a small tumor. SRS uses extremely accurate image-guided tumor targeting and patient positioning. Therefore, a high dose of radiation can be given without excess damage to normal tissue. SRS can be used to treat small tumors with well-defined edges. It is most commonly used in the treatment of brain or spinal tumors and brain metastases from other cancer types. For the treatment of some brain metastases, patients may receive radiation therapy to the entire brain (called whole-brain radiation therapy) in addition to SRS. SRS requires the use of a head frame or other device to immobilize the patient during treatment to ensure that the high dose of radiation is delivered accurately.

Stereotactic body radiation therapy (SBRT) delivers radiation therapy in fewer sessions, using smaller radiation fields and higher doses than 3D-CRT in most cases. SBRT may treat tumors that lie outside the brain and spinal cord. Because these tumors are more likely to move with the normal motion of the body, and therefore cannot be targeted as accurately as tumors within the brain or spine, SBRT is usually given in more than one dose. SBRT can be used to treat small, isolated tumors, including cancers in the lung and liver. SBRT systems may be known by their brand names, such as the CyberKnife®.

In proton therapy, external-beam radiation therapy may be delivered by proton. Protons are a type of charged particle. Proton beams differ from photon beams mainly in the way they deposit energy in living tissue. Whereas photons deposit energy in small packets all along their path through tissue, protons deposit much of their energy at the end of their path (called the Bragg peak) and deposit less energy along the way. Use of protons may reduce the exposure of normal tissue to radiation, possibly allowing the delivery of higher doses of radiation to a tumor.

Other charged particle beams such as electron beams may be used to irradiate superficial tumors, such as skin cancer or tumors near the surface of the body, but they cannot travel very far through tissue.

Internal radiation therapy (brachytherapy) is radiation delivered from radiation sources (radioactive materials) placed inside or on the body. Several brachytherapy techniques are used in cancer treatment. Interstitial brachytherapy may use a radiation source placed within tumor tissue, such as within a prostate tumor. Intracavitary brachytherapy may use a source placed within a surgical cavity or a body cavity, such as the chest cavity, near a tumor. Episcleral brachytherapy, which may be used to treat melanoma inside the eye, may use a source that is attached to the eye. In brachytherapy, radioactive isotopes can be sealed in tiny pellets or "seeds." These seeds may be placed in patients using delivery devices, such as needles, catheters, or some other type of carrier. As the isotopes decay naturally, they give off radiation that may damage nearby cancer cells. Brachytherapy may be able to deliver higher doses of radiation to some cancers than external-beam radiation therapy while causing less damage to normal tissue.

Brachytherapy can be given as a low-dose-rate or a high-dose-rate treatment. In low-dose-rate treatment, cancer cells receive continuous low-dose radiation from the source over a period of several days. In high-dose-rate treatment, a robotic machine attached to delivery tubes placed inside the body may guide one or more radioactive sources into or near a tumor, and then removes the sources at the end of each treatment session. High-dose-rate treatment can be given in one or more treatment sessions. An example of a high-dose-rate treatment is the MammoSite® system. Bracytherapy may be used to treat patients with breast cancer who have undergone breast-conserving surgery.

The placement of brachytherapy sources can be temporary or permanent. For permanent brachytherapy, the sources may be surgically sealed within the body and left there, even after all of the radiation has been given off. In some instances, the remaining material (in which the radioactive isotopes were sealed) does not cause any discomfort or harm to the patient. Permanent brachytherapy is a type of low-dose-rate brachytherapy. For temporary brachytherapy, tubes (catheters) or other carriers are used to deliver the radiation sources, and both the carriers and the radiation sources are removed after treatment. Temporary brachytherapy can be either low-dose-rate or high-dose-rate treatment. Brachytherapy may be used alone or in addition to external-beam radiation therapy to provide a "boost" of radiation to a tumor while sparing surrounding normal tissue.

In systemic radiation therapy, a patient may swallow or receive an injection of a radioactive substance, such as radioactive iodine or a radioactive substance bound to a monoclonal antibody. Radioactive iodine (131I) is a type of systemic radiation therapy commonly used to help treat cancer, such as thyroid cancer. Thyroid cells naturally take up radioactive iodine. For systemic radiation therapy for some other types of cancer, a monoclonal antibody may help target the radioactive substance to the right place. The antibody joined to the radioactive substance travels through the blood, locating and killing tumor cells. For example, the drug ibritumomab tiuxetan (Zevalin®) may be used for the treatment of certain types of B-cell non-Hodgkin lymphoma (NHL). The antibody part of this drug recognizes and binds to a protein found on the surface of B lymphocytes. The combination drug regimen of tositumomab and iodine I 131 tositumomab (Bexxar®) may be used for the treatment of certain types of cancer, such as NHL. In this regimen, nonradioactive tositumomab antibodies may be given to patients first, followed by treatment with tositumomab antibodies that have 131I attached. Tositumomab may recognize and bind to the same protein on B lymphocytes as ibritumomab. The nonradioactive form of the antibody may help protect normal B lymphocytes from being damaged by radiation from 131I.

Some systemic radiation therapy drugs relieve pain from cancer that has spread to the bone (bone metastases). This is a type of palliative radiation therapy. The radioactive drugs samarium-153-lexidronam (Quadramet®) and strontium-89 chloride (Metastron®) are examples of radiopharmaceuticals may be used to treat pain from bone metastases.

Biological therapy (sometimes called immunotherapy, biotherapy, or biological response modifier (BRM) therapy) uses the body's immune system, either directly or indirectly, to fight cancer or to lessen the side effects that may be caused by some cancer treatments. Biological therapies include interferons, interleukins, colony-stimulating factors, monoclonal antibodies, vaccines, gene therapy, and nonspecific immunomodulating agents.

Interferons (IFNs) are types of cytokines that occur naturally in the body. Interferon alpha, interferon beta, and interferon gamma are examples of interferons that may be used in cancer treatment.

Like interferons, interleukins (ILs) are cytokines that occur naturally in the body and can be made in the laboratory. Many interleukins have been identified for the treatment of cancer. For example, interleukin-2 (IL-2 or aldesleukin), interleukin 7, and interleukin 12 have may be used as an anti-cancer treatment. IL-2 may stimulate the growth and activity of many immune cells, such as lymphocytes, that can destroy cancer cells. Interleukins may be used to treat a number of cancers, including leukemia, lymphoma, and brain, colorectal, ovarian, breast, kidney and prostate cancers.

Colony-stimulating factors (CSFs) (sometimes called hematopoietic growth factors) may also be used for the treatment of cancer. Some examples of CSFs include, but are not limited to, G-CSF (filgrastim) and GM-CSF (sargramostim). CSFs may promote the division of bone marrow stem cells and their development into white blood cells, platelets, and red blood cells. Bone marrow is critical to the body's immune system because it is the source of all blood cells. Because anticancer drugs can damage the body's ability to make white blood cells, red blood cells, and platelets, stimulation of the immune system by CSFs may benefit patients undergoing other anti-cancer treatment, thus CSFs may be combined with other anti-cancer therapies, such as chemotherapy. CSFs may be used to treat a large variety of cancers, including lymphoma, leukemia, multiple myeloma, melanoma, and cancers of the brain, lung, esophagus, breast, uterus, ovary, prostate, kidney, colon, and rectum.

Another type of biological therapy includes monoclonal antibodies (MOABs or MoABs). These antibodies may be produced by a single type of cell and may be specific for a particular antigen. To create MOABs, a human cancer cells may be injected into mice. In response, the mouse immune system can make antibodies against these cancer cells. The mouse plasma cells that produce antibodies may be isolated and fused with laboratory-grown cells to create "hybrid" cells called hybridomas. Hybridomas can indefinitely produce large quantifies of these pure antibodies, or MOABs. MOABs may be used in cancer treatment in a number of ways. For instance, MOABs that react with specific types of cancer may enhance a patient's immune response to the cancer. MOABs can be programmed to act against cell growth factors, thus interfering with the growth of cancer cells.

MOABs may be linked to other anti-cancer therapies such as chemotherapeutics, radioisotopes (radioactive substances), other biological therapies, or other toxins. When the antibodies latch onto cancer cells, they deliver these anti-cancer therapies directly to the tumor, helping to destroy it. MOABs carrying radioisotopes may also prove useful in diagnosing certain cancers, such as colorectal, ovarian, and prostate.

Rituxan® (rituximab) and Herceptin® (trastuzumab) are examples of MOABs that may be used as a biological therapy. Rituxan may be used for the treatment of non-Hodgkin lymphoma. Herceptin can be used to treat metastatic breast cancer in patients with tumors that produce excess amounts of a protein called HER2. Alternatively, MOABs may be used to treat lymphoma, leukemia, melanoma, and cancers of the brain, breast, lung, kidney, colon, rectum, ovary, prostate, and other areas.

Cancer vaccines are another form of biological therapy. Cancer vaccines may be designed to encourage the patient's immune system to recognize cancer cells. Cancer vaccines may be designed to treat existing cancers (therapeutic vaccines) or to prevent the development of cancer (prophylactic vaccines). Therapeutic vaccines may be injected in a person after cancer is diagnosed. These vaccines may stop the growth of existing tumors, prevent cancer from recurring, or eliminate cancer cells not killed by prior treatments. Cancer vaccines given when the tumor is small may be able to eradicate the cancer. On the other hand, prophylactic vaccines are given to healthy individuals before cancer develops. These vaccines are designed to stimulate the immune system to attack viruses that can cause cancer. By targeting these cancer-causing viruses, development of certain cancers may be prevented. For example, cervarix and gardasil are vaccines to treat human papilloma virus and may prevent cervical cancer. Therapeutic vaccines may be used to treat melanoma, lymphoma, leukemia, and cancers of the brain, breast, lung, kidney, ovary, prostate, pancreas, colon, and rectum. Cancer vaccines can be used in combination with other anti-cancer therapies.

Gene therapy is another example of a biological therapy. Gene therapy may involve introducing genetic material into a person's cells to fight disease. Gene therapy methods may improve a patient's immune response to cancer. For example, a gene may be inserted, into an immune cell to enhance its ability to recognize and attack cancer cells. In another approach, cancer cells may be injected with genes that cause the cancer cells to produce cytokines and stimulate the immune system.

In some instances, biological therapy includes nonspecific immunomodulating agents. Nonspecific immunomodulating agents are substances that stimulate or indirectly augment the immune system. Often, these agents target key immune system cells and may cause secondary responses such as increased production of cytokines and immunoglobulins. Two nonspecific immunomodulating agents used in cancer treatment are *bacillus* Calmette-Guerin (BCG) and levamisole. BCG may be used in the treatment of superficial bladder cancer following surgery. BCG may work by stimulating an inflammatory, and possibly an immune, response. A solution of BCG may be instilled in the bladder. Levamisole is sometimes used along with fluorouracil (5-FU) chemotherapy in the treatment of stage III (Dukes' C) colon cancer following surgery. Levamisole may act to restore depressed immune function.

Photodynamic therapy (PDT) is an anti-cancer treatment that may use a drug, called a photosensitizer or photosensitizing agent, and a particular type of light. When photosensitizers are exposed to a specific wavelength of light, they may produce a form of oxygen that kills nearby cells. A photosensitizer may be activated by light of a specific wavelength. This wavelength determines how far the light can travel into the body. Thus, photosensitizers and wavelengths of light may be used to treat different areas of the body with PDT.

In the first step of PDT for cancer treatment, a photosensitizing agent may be injected into the bloodstream. The agent may be absorbed by cells all over the body but may stay in cancer cells longer than it does in normal cells. Approximately 24 to 72 hours after injection, when most of the agent has left normal cells but remains in cancer cells, the tumor can be exposed to light. The photosensitizer in the tumor can absorb the light and produces an active form of oxygen that destroys nearby cancer cells. In addition to directly killing cancer cells, PDT may shrink or destroy tumors in two other ways. The photosensitizer can damage blood vessels in the tumor, thereby preventing the cancer from receiving necessary nutrients. PDT may also activate the immune system to attack the tumor cells.

The light used for PDT can come from a laser or other sources. Laser light can be directed through fiber optic cables (thin fibers that transmit light) to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer. PDT is usually performed as an outpatient procedure. PDT may also be repeated and may be used with other therapies, such as surgery, radiation, or chemotherapy.

Extracorporeal photopheresis (ECP) is a type of PDT in which a machine may be used to collect the patient's blood cells. The patient's blood cells may be treated outside the body with a photosensitizing agent, exposed to light, and then returned to the patient. ECP may be used to help lessen the severity of skin symptoms of cutaneous T-cell lymphoma that has not responded to other therapies. ECP may be used to treat other blood cancers, and may also help reduce rejection after transplants.

Additionally, photosensitizing agent, such as porfimer sodium or Photofrin®, may be used in PDT to treat or relieve the symptoms of esophageal cancer and non-small cell lung cancer. Porfimer sodium may relieve symptoms of esophageal cancer when the Cancer obstructs the esophagus or when the cancer cannot be satisfactorily treated with laser therapy alone. Porfimer sodium may be used to treat non-small cell lung cancer in patients for whom the usual treatments are not appropriate, and to relieve symptoms in patients with non-small cell lung cancer that obstructs the airways. Porfimer sodium may also be used for the treatment of precancerous lesions in patients with Barrett esophagus, a condition that can lead to esophageal cancer.

Laser therapy may use high-intensity light to treat cancer and other illnesses. Lasers can be used to shrink or destroy tumors or precancerous growths. Lasers are most commonly used to treat superficial cancers (cancers on the surface of the body or the lining of internal organs) such as basal cell skin cancer and the very early stages of some cancers, such as cervical, penile, vaginal, vulvar, and non-small cell lung cancer.

Lasers may also be used to relieve certain symptoms of cancer, such as bleeding or obstruction. For example, lasers can be used to shrink or destroy a tumor that is blocking a patient's trachea (windpipe) or esophagus. Lasers also can be used to remove colon polyps or tumors that are blocking the colon or stomach.

Laser therapy is often given through a flexible endoscope (a thin, lighted tube used to look at tissues inside the body). The endoscope is fitted with optical fibers (thin fibers that transmit light). It is inserted through an opening in the body, such as the mouth, nose, anus, or vagina. Laser light is then precisely aimed to cut or destroy a tumor.

Laser-induced interstitial thermotherapy (LITT), or interstitial laser photocoagulation, also uses lasers to treat some cancers. LITT is similar to a cancer treatment called hyperthermia, which uses heat to shrink tumors by damaging or killing cancer cells. During LITT, an optical fiber is inserted into a tumor. Laser light at the tip of the fiber raises the temperature of the tumor cells and damages or destroys them. LITT is sometimes used to shrink tumors in the liver.

Laser therapy can be used alone, but most often it is combined with other treatments, such as surgery, chemotherapy, or radiation therapy. In addition, lasers can seal nerve endings to reduce pain after surgery and seal lymph vessels to reduce swelling and limit the spread of tumor cells.

Lasers used to treat cancer may include carbon dioxide (CO2) lasers, argon lasers, and neodymium:yttrium-aluminum-garnet (Nd:YAG) lasers. Each of these can shrink or destroy tumors and can be used with endoscopes. CO2 and argon lasers can cut the skin's surface without going into deeper layers. Thus, they can be used to remove superficial cancers, such as skin cancer. In contrast, the Nd:YAG laser is more commonly applied through an endoscope to treat internal organs, such as the uterus, esophagus, and colon. Nd:YAG laser light can also travel through optical fibers into specific areas of the body during LITT. Argon lasers are often used to activate the drugs used in PDT.

For patients with high test scores consistent with systemic disease outcome after prostatectomy, additional treatment modalities such as adjuvant chemotherapy (e.g., docetaxel, mitoxantrone and prednisone), systemic radiation therapy (e.g., samarium or strontium) and/or anti-androgen therapy (e.g., surgical castration, finasteride, dutasteride) can be designated. Such patients would likely be treated immediately with anti-androgen therapy alone or in combination with radiation therapy in order to eliminate presumed micrometastatic disease, which cannot be detected clinically but can be revealed by the target sequence expression signature.

Such patients can also be more closely monitored for signs of disease progression. For patients with intermediate test scores consistent with biochemical recurrence only (BCR-only or elevated PSA that does not rapidly become manifested as systemic disease only localized adjuvant therapy (e.g., radiation therapy of the prostate bed) or short course of anti-androgen therapy would likely be administered. For patients with low scores or scores consistent with no evidence of disease (NED) adjuvant therapy would not likely be recommended by their physicians in order to avoid treatment-related side effects such as metabolic syndrome (e.g., hypertension, diabetes and/or weight gain), osteoporosis, proctitis, incontinence or impotence. Patients with samples consistent with NED could be designated for watchful waiting, or for no treatment. Patients with test scores that do not correlate with systemic disease but who have successive PSA increases could be designated for watchful waiting, increased monitoring, or lower dose or shorter duration anti-androgen therapy.

Target sequences can be grouped so that information obtained about the set of target sequences in the group can be used to make or assist in making a clinically relevant judgment such as a diagnosis, prognosis, or treatment choice.

In some instances, a patient report is provided. In some instances, the patient report comprises a representation of measured expression levels of a plurality of targets in a biological sample from the patient, wherein the representation comprises expression levels of (a) one or more targets corresponding to one or more of the targets listed in Table 6; (b) one or more targets comprising a sequence of one or more of the sequences depicted in Table 7; (c) one or more targets comprising a sequence that is the complement of one or more of the sequences depicted in Table 7; (d) one or more targets comprising a sequence that is the reverse complement of one or more of the sequences depicted in Table 7; or (e) a combination thereof. In some instances, the one or more targets correspond to at least 2, 3, 4, 5, 10, 15, 20, 25, 30, 35, 40, 45, 50, 55, 60, 65, 70, 75, 80, 90, 100, 110, 120, 130, 140, or 150 of the targets listed in Table 6. In some instances, the one or more targets comprises a sequence of at least 2, 3, 4, 5, 10, 15, 20, 25, 30, 35, 40, 45, 50, 55, 60, 65, 70, 75, 80, 90, 100, 110, 120, 130, 140, or 150 of the sequences depicted in Table 7. In some instances, the one or more targets comprises a sequence that is the complement of at least 2, 3, 4, 5, 10, 15, 20, 25, 30, 35, 40, 45, 50, 55, 60, 65, 70, 75, 80, 90, 100, 110, 120, 130, 140, or 150 of the sequences depicted in Table 7. In some instances, the one or more targets comprises a sequence that is the reverse complement of at least 2, 3, 4, 5, 10, 15, 20, 25, 30, 35, 40, 45, 50, 55, 60, 65, 70, 75, 80, 90, 100, 110, 120, 130, 140, or 150 of the sequences depicted in Table 7. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of targets from one or more sets of patients with known disease status and/or outcome. The report can be used to inform the patient and/or treating physician of the expression levels of the expressed targets, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

In some instances, a therapeutic regimen comprises two or more therapies. In some instances, a therapeutic regimen comprises three or more therapies. In some instances, a therapeutic regimen comprises four or more therapies. In some instances, a therapeutic regimen comprises five or more therapies. In some instances, a therapeutic regimen comprises at least 6, 7, 8, 9, 10, 11, 12, 13, 14, or 15 therapies. In some instances, the therapies are administered simultaneously. In some instances, the therapies are administered sequentially. In some instances, the therapies are administered 1, 2, 3, 4, 5, 6, 7, 8, 9, 10, 11, 12, 13, 14, 15, 16, 17, 18, 19, 20, 21, 22, 23, or 24 hours apart; 1, 2, 3, 4, 5, 6, 7, 8, 9, 10, 11, 12, 13, 14, 15, 16, 17, 18, 19, 20, 21, 22, 23, or 24 days apart; 1, 2, 3, 4, 5, 6, 7, 8, 9, 10, 11, 12, 13, 14, 15, 16, 17, 18, 19, 20, 21, 22, 23, or 24 weeks apart; 1, 2, 3, 4, 5, 6, 7, 8, 9, 10, 11, 12, 13, 14, 15, 16, 17, 18, 19, 20, 21, 22, 23, or 24 months apart.

Exemplary Embodiments

Disclosed herein, in some embodiments, is a method comprising (a) assaying an expression level in a sample from the subject for a plurality of targets, wherein the plurality of targets comprises one or more targets selected from (i) a target listed in Table 6; (ii) a target comprising a sequence selected from SEQ ID NOs: 1-153; (iii) a target comprising a sequence that is a complement of a sequence selected from SEQ ID NOs: 1-153; (iv) a target comprising a sequence that is a reverse complement of a sequence selected from SEQ ID NOs: 1-153; or (v) a combination of (i-iv); and diagnosing, prognosing, determining progression the cancer, or predicting benefit from therapy in a subject based on the expression levels of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a thyroid cancer. In some embodiments, the plurality of targets comprises a nucleic acid sequence. In some embodiments, the nucleic acid sequence is a DNA sequence. In some embodiments, the nucleic acid sequence is an RNA sequence. In some instances, the plurality of targets comprises a non-coding RNA transcript. In some instances, the non-coding RNA transcript is non-polyadenylated. In some instances, the plurality of targets comprises a polyadenylated target. In some embodiments, the plurality of targets comprises an intronic sequence, a sequence within the UTR, non-coding RNA transcript, or a portion thereof. In some embodiments, the plurality of targets comprises an intronic sequence or a portion of an intronic sequence. In some embodiments, the plurality of targets comprises a UTR sequence or a portion of a UTR sequence. In some embodiments, the plurality of targets comprises non-coding RNA transcript. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the plurality of targets comprises an exon-coding transcript or a portion of an exon-coding transcript. In some embodiments, the exon-coding transcript is an exonic sequence. In some embodiments, the plurality of targets comprises two or more targets. In some embodiments, the plurality of targets comprises three or more targets. In some embodiments, the plurality of targets comprises five or more targets. In some embodiments, the plurality of targets comprises ten or more targets. In some embodiments, the plurality of targets comprises twenty or more targets. In some embodiments, the plurality of targets comprises thirty or more targets. In some embodiments, the plurality of targets comprises forty or more targets. In some embodiments, the plurality of targets comprises fifty or more targets. In some embodiments, the plurality of targets comprises sixty or more targets. In some embodiments, the plurality of targets comprises two or more targets selected from a target listed in Table 6. In some embodiments, the plurality of targets comprises three or more targets selected from a target listed in Table 6. In some embodiments, the plurality of targets comprises five or more targets selected from a target listed in Table 6. In some embodiments, the plurality of targets comprises ten or more targets selected from a target listed in Table 6. In some embodiments, the plurality of targets comprises twenty or more targets selected from a target listed in Table 6. In some embodiments, the plurality of targets comprises thirty or more targets selected from a target listed in Table 6. In some embodiments, the plurality of targets comprises two or more targets comprising a sequence selected from SEQ ID NOs: 1-153. In some embodiments, the plurality of targets comprises three or more targets comprising a sequence selected from SEQ ID NOs: 1-153. In some embodiments, the plurality of targets comprises five or more targets comprising a sequence selected from SEQ ID NOs: 1-153. In some embodiments, the plurality of targets comprises ten or more targets comprising a sequence selected from SEQ ID NOs: 1-153. In some embodiments, the plurality of targets comprises twenty or more targets comprising a sequence selected from SEQ ID NOs: 1-153. In some embodiments, the plurality of targets comprises thirty or more targets comprising a sequence selected from SEQ ID NOs: 1-153. In some embodiments, the plurality of targets comprises two or more targets comprising a sequence that is a complement of a sequence selected from SEQ ID NOs: 1-153. In some embodiments, the plurality of targets comprises three or more targets comprising a sequence that is a complement of a sequence selected from SEQ ID NOs: 1-153. In some embodiments, the plurality of targets comprises five or more targets comprising a sequence that is a complement of a sequence selected from SEQ ID NOs: 1-153. In some embodiments, the plurality of targets comprises ten or more targets comprising a sequence that is a complement of a sequence selected from SEQ ID NOs: 1-153. In some embodiments, the plurality of targets comprises twenty or more targets comprising a sequence that is a complement of a sequence selected from SEQ ID NOs: 1-153. In some embodiments, the plurality of targets comprises thirty or more targets comprising a sequence that is a complement of a sequence selected from SEQ ID NOs: 1-153. In some embodiments, the plurality of targets comprises two or more targets comprising a sequence that is a reverse complement of a sequence selected from SEQ ID NOs: 1-153. In some embodiments, the plurality of targets comprises three or more targets comprising a sequence that is a reverse complement of a sequence selected from SEQ ID NOs: 1-153. In some embodiments, the plurality of targets comprises five or more targets comprising a sequence that is a reverse complement of a sequence selected from SEQ ID NOs: 1-153. In some embodiments, the plurality of targets comprises ten or more targets comprising a sequence that is a complement of a sequence selected from SEQ ID NOs: 1-153. In some embodiments, the plurality of targets comprises twenty or more targets comprising a sequence that is a reverse complement of a sequence selected from SEQ ID NOs: 1-153. In some embodiments, the plurality of targets comprises thirty or more targets comprising a sequence that is a reverse complement of a sequence selected from SEQ ID NOs: 1-153. In some instances, the plurality of targets comprises at least ten consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least twenty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least thirty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least forty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least fifty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least sixty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least seventy consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least 80, 90, 100, 120, 140, 160, 180, 200, 250, 300, 350, 400, 450, or 500 consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least 600, 700, 800, 900, 1000, 1100, 1200, 1300, or 1400 consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some embodiments, the method further comprises assaying an expression level of a miRNA. In some embodiments, the method further comprises assaying an expression level of a siRNA. In some embodiments, the method further comprises assaying an expression level of a snoRNA. In some embodiments, the method further comprises assaying an expression level of a lincRNA. In some embodiments, the method further comprises amplifying the plurality of targets. In some embodiments, the method further comprises conducting a multiplexed reaction. In some embodiments, the method further comprises sequencing the plurality of targets. In some embodiments, the method further comprises quantifying the plurality of targets. In some embodiments, the method further comprises hybridizing a label to a plurality of targets. In some embodiments, the method does not comprise amplifying the plurality of targets. In some embodiments, the method comprises reverse transcribing the plurality of targets. In some embodiments, the method comprises hybridizing a probe to the plurality of targets. In some embodiments, the probe is labeled. In some embodiments, the plurality of targets is labeled. In some embodiments, the method further comprises attaching the plurality of targets to a solid support. In some embodiments, the method further comprises attaching a probe or probe set to a solid support. In some embodiments, the solid support is an array. In some embodiments, the solid support is a bead. In some embodiments, the solid support is a plate. In some embodiments, the solid support is a microwell plate. In some embodiments, the diagnosing, predicting, and/or monitoring the status or outcome of a cancer comprises determining the malignancy of the cancer. In some embodiments, the diagnosing, predicting, and/or monitoring the status or outcome of a cancer includes determining the stage of the cancer. In some embodiments, the diagnosing, predicting, and/or monitoring the status or outcome of a cancer includes assessing the risk of cancer recurrence. In some embodiments, diagnosing, predicting, and/or monitoring the status or outcome of a cancer may comprise determining the efficacy of treatment. In some embodiments, diagnosing, predicting, and/or monitoring the status or outcome of a cancer comprises determining a therapeutic regimen. Determining a therapeutic regimen can comprise administering an anti-cancer therapeutic. Alternatively, determining the treatment for the cancer comprises modifying a therapeutic regimen. Modifying a therapeutic regimen may comprise increasing, decreasing, or terminating a therapeutic regimen. In some embodiments, diagnosing, prognosing, determining progression the cancer, or predicting benefit from therapy comprises determining the cancer status of the subject. In some instances, the expression level determines the cancer status of the subject with at least 50% specificity. In some instances, the expression level determines the cancer status of the subject with at least 60% specificity. In some instances, the expression level determines the cancer status of the subject with at least 65% specificity. In some instances, the expression level determines the cancer status of the subject with at least 70% specificity. In some instances, the expression level determines the cancer status of the subject with at least 75% specificity. In some instances, the expression level determines the cancer status of the subject with at least 80% specificity. In some instances, the expression level determines the cancer status of the subject with at least 85% specificity. In some instances, assaying the expression level of a plurality of targets comprises the use of a probe set. Alternatively, assaying the expression level comprises the use of a classifier. In some instances, the classifier comprises a probe selection region (PSR). Alternatively, the classifier comprises the use of an algorithm. In some instances, the algorithm comprises a machine learning algorithm. In some instances, assaying the expression level comprises sequencing the plurality of targets. In some instances, assaying the expression level comprises quantifying the plurality of targets. In some instances, two or more samples are obtained from the subject. In some instances, the samples are obtained prior to diagnosis and after diagnosis. In some instances, the samples are obtained prior to treatment, during treatment and/or after treatment. In some instances, the samples are obtained monthly. In some instances, the method further comprises analyzing the expression level of the plurality targets from a control sample. In some instances, the expression level of the plurality of targets from the sample is compared to the expression level of the plurality of targets from the control sample. In some instances, the control sample is from an untreated subject. In some instances, the control sample is from a treated subject. In some instances, the control sample is from a non-responder to a therapeutic regimen. In some instances, the control sample is from a responder to a therapeutic regimen. In some instances, the control sample is from a healthy subject. In some instances, the control sample is from a subject suffering from a cancer.

Further disclosed herein, in some embodiments, is a method comprising: (a) assaying an expression level in a sample from the subject for a plurality of targets, wherein the plurality of targets comprises one or more targets selected from (i) a target listed in Table 6; (ii) a target comprising a sequence selected from SEQ ID NOs: 1-153; (iii) a target comprising a sequence that is a complement of a sequence selected from SEQ ID NOs: 1-153; (iv) a target comprising a sequence that is a reverse complement of a sequence selected from SEQ ID NOs: 1-153; or (v) a combination of (i-iv); and (b) determining the treatment for the cancer based on the expression level of the plurality of targets. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a thyroid cancer. In some embodiments, the plurality of targets comprises a nucleic acid sequence. In some embodiments, the nucleic acid sequence is a DNA sequence. In some embodiments, the nucleic acid sequence is an RNA sequence. In some instances, the plurality of targets comprises a non-coding RNA transcript. In some instances, the non-coding RNA transcript is non-polyadenylated. In some instances, the plurality of targets comprises a polyadenylated target. In some embodiments, the plurality of targets comprises an intronic sequence, a sequence within the UTR, non-coding RNA transcript, or a portion thereof. In some embodiments, the plurality of targets comprises an intronic sequence or a portion of an intronic sequence. In some embodiments, the plurality of targets comprises a UTR sequence or a portion of a UTR sequence. In some embodiments, the plurality of targets comprises non-coding RNA transcript. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the plurality of targets comprises an exon-coding transcript or a portion of an exon-coding transcript. In some embodiments, the exon-coding transcript is an exonic sequence. In some embodiments, the plurality of targets comprises two or more targets. In some embodiments, the plurality of targets comprises three or more targets. In some embodiments, the plurality of targets comprises five or more targets. In some embodiments, the plurality of targets comprises ten or more targets. In some embodiments, the plurality of targets comprises twenty or more targets. In some embodiments, the plurality of targets comprises thirty or more targets. In some embodiments, the plurality of targets comprises forty or more targets. In some embodiments, the plurality of targets comprises fifty or more targets. In some embodiments, the plurality of targets comprises sixty or more targets. In some embodiments, the plurality of targets comprises two or more targets selected from a target listed in Table 6. In some embodiments, the plurality of targets comprises three or more targets selected from a target listed in Table 6. In some embodiments, the plurality of targets comprises five or more targets selected from a target listed in Table 6. In some embodiments, the plurality of targets comprises ten or more targets selected from a target listed in Table 6. In some embodiments, the plurality of targets comprises twenty or more targets selected from a target listed in Table 6. In some embodiments, the plurality of targets comprises thirty or more targets selected from a target listed in Table 6. In some embodiments, the plurality of targets comprises two or more targets comprising a sequence selected from SEQ ID NOs: 1-153. In some embodiments, the plurality of targets comprises three or more targets comprising a sequence selected from SEQ ID NOs: 1-153. In some embodiments, the plurality of targets comprises five or more targets comprising a sequence selected from SEQ ID NOs: 1-153. In some embodiments, the plurality of targets comprises ten or more targets comprising a sequence selected from SEQ ID NOs: 1-153. In some embodiments, the plurality of targets comprises twenty or more targets comprising a sequence selected from SEQ ID NOs: 1-153. In some embodiments, the plurality of targets comprises thirty or more targets comprising a sequence selected from SEQ ID NOs: 1-153. In some embodiments, the plurality of targets comprises two or more targets comprising a sequence that is a complement of a sequence selected from SEQ ID NOs: 1-153. In some embodiments, the plurality of targets comprises three or more targets comprising a sequence that is a complement of a sequence selected from SEQ ID NOs: 1-153. In some embodiments, the plurality of targets comprises five or more targets comprising a sequence that is a complement of a sequence selected from SEQ ID NOs: 1-153. In some embodiments, the plurality of targets comprises ten or more targets comprising a sequence that is a complement of a sequence selected from SEQ ID NOs: 1-153. In some embodiments, the plurality of targets comprises twenty or more targets comprising a sequence that is a complement of a sequence selected from SEQ ID NOs: 1-153. In some embodiments, the plurality of targets comprises thirty or more targets comprising a sequence that is a complement of a sequence selected from SEQ ID NOs: 1-153. In some embodiments, the plurality of targets comprises two or more targets comprising a sequence that is a reverse complement of a sequence selected from SEQ ID NOs: 1-153. In some embodiments, the plurality of targets comprises three or more targets comprising a sequence that is a reverse complement of a sequence selected from SEQ ID NOs: 1-153. In some embodiments, the plurality of targets comprises five or more targets comprising a sequence that is a reverse complement of a sequence selected from SEQ ID NOs: 1-153. In some embodiments, the plurality of targets comprises ten or more targets comprising a sequence that is a complement of a sequence selected from SEQ ID NOs: 1-153. In some embodiments, the plurality of targets comprises twenty or more targets comprising a sequence that is a reverse complement of a sequence selected from SEQ ID NOs: 1-153. In some embodiments, the plurality of targets comprises thirty or more targets comprising a sequence that is a reverse complement of a sequence selected from SEQ ID NOs: 1-153. In some instances, the plurality of targets comprises at least ten consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least twenty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least thirty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least forty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least fifty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least sixty consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least seventy consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least 80, 90, 100, 120, 140, 160, 180, 200, 250, 300, 350, 400, 450, or 500 consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some instances, the plurality of targets comprises at least 600, 700, 800, 900, 1000, 1100, 1200, 1300, or 1400 consecutive nucleotides of a sequence selected from SEQ ID NOs: 1-153, an RNA form of a sequence selected from SEQ ID NOs: 1-153, a complement of sequence selected from SEQ ID NOs: 1-153, or a reverse complement of a sequence selected from SEQ ID NOs: 1-153. In some embodiments, the method further comprises assaying an expression level of a miRNA. In some embodiments, the method further comprises assaying an expression level of a siRNA. In some embodiments, the method further comprises assaying an expression level of a snoRNA. In some embodiments, the method further comprises assaying an expression level of a lincRNA. In some embodiments, the method further comprises amplifying the plurality of targets. In some embodiments, the method further comprises conducting a multiplexed reaction. In some embodiments, the method further comprises sequencing the plurality of targets. In some embodiments, the method further comprises quantifying the plurality of targets. In some embodiments, the method further comprises hybridizing a label to a plurality of targets. In some embodiments, the method does not comprise amplifying the plurality of targets. In some embodiments, the method comprises reverse transcribing the plurality of targets. In some embodiments, the method comprises hybridizing a probe to the plurality of targets. In some embodiments, the probe is labeled. In some embodiments, the plurality of targets is labeled. In some embodiments, the method further comprises attaching the plurality of targets to a solid support. In some embodiments, the method further comprises attaching a probe or probe set to a solid support. In some embodiments, the solid support is an array. In some embodiments, the solid support is a bead. In some embodiments, the solid support is a plate. In some embodiments, the solid support is a microwell plate. In some embodiments, determining the treatment for the cancer comprises determining the efficacy of treatment. In some embodiments, determining the treatment for the cancer comprises administering an anti-cancer therapeutic. Alternatively, determining the treatment for the cancer comprises modifying a therapeutic regimen. In some instances, modifying a therapeutic regimen comprises increasing, decreasing, or terminating a therapeutic regimen. In some instances, assaying the expression level of a plurality of targets comprises the use of a probe set. Alternatively, assaying the expression level comprises the use of a classifier. In some instances, the classifier comprises a probe selection region (PSR). Alternatively, the classifier comprises the use of an algorithm. In some instances, the algorithm comprises a machine learning algorithm. In some instances, assaying the expression level comprises sequencing the plurality of targets. In some instances, assaying the expression level comprises quantifying the plurality of targets. In some instances, two or more samples are obtained from the subject. In some instances, the samples are obtained prior to diagnosis and after diagnosis. In some instances, the samples are obtained prior to treatment, during treatment and/or after treatment. In some instances, the samples are obtained monthly. In some instances, the method further comprises analyzing the expression level of the plurality targets from a control sample. In some instances, the expression level of the plurality of targets from the sample is compared to the expression level of the plurality of targets from the control sample. In some instances, the control sample is from an untreated subject. In some instances, the control sample is from a treated subject. In some instances, the control sample is from a non-responder to a therapeutic regimen. In some instances, the control sample is from a responder to a therapeutic regimen. In some instances, the control sample is from a healthy subject. In some instances, the control sample is from a subject suffering from a cancer.

The methods use the probe sets, probes and primers described herein to provide expression signatures or profiles from a test sample derived from a subject having or suspected of having cancer. In some embodiments, such methods involve contacting a test sample with a probe or probe set (either in solution or immobilized) under conditions that permit hybridization of the probe(s) or probe set(s) to any target(s) present in the test sample and then detecting any probe:target duplexes formed as an indication of the presence of the target nucleic acid in the sample. Expression patterns thus determined are then compared to one or more reference profiles or signatures. Optionally, the expression pattern can be normalized. The methods use the probe sets, probes and primers described herein to provide expression signatures or profiles from a test sample derived from a subject to classify the cancer as recurrent or non-recurrent.

Disclose herein, in some embodiments, is a probe set for assessing a cancer status of a subject comprising a plurality of probes, wherein the probes in the set are capable of detecting an expression level of one or more targets, wherein the expression level determines the cancer status of the subject with at least 40% specificity; and wherein at least one or more targets are selected from: (a) a target listed in Table 6; (b) a target comprising a sequence selected from SEQ ID NOs: 1-153 listed in Table 7; (c) a target comprising a sequence that is a complement of a sequence selected from SEQ ID NOs: 1-153 listed in Table 7; (d) a target comprising a sequence that is a reverse complement of a sequence selected from SEQ ID NOs: 1-153 listed in Table 7; or (e) a combination of (a-d). In some instances, the cancer is selected from the group consisting of a carcinoma, sarcoma, leukemia, lymphoma, myeloma, and a CNS tumor. In some instances, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some instances, the cancer is a prostate cancer. In some instances, the cancer is a pancreatic cancer. In some instances, the cancer is a thyroid cancer. In some instances, assessing the cancer status includes assessing cancer recurrence risk. In some instances, the assessing the cancer status includes determining a treatment modality. In some instances, assessing the cancer status includes determining the efficacy of treatment. In some instances, the one or more targets comprise a nucleic acid sequence. In some instances, the nucleic acid sequence is a DNA sequence. In some instances, the nucleic acid sequence is an RNA sequence. In some instances, the one or more targets are a non-coding RNA transcript. In some instances, the non-coding RNA transcript is non-polyadenylated. In some instances, the one or more targets are polyadenylated targets. In some embodiments, the one or more targets comprise an intronic sequence, a sequence within the UTR, or a non-coding RNA transcript. In some embodiments, the one or more targets comprise an intronic sequence or a portion of an intronic sequence. In some embodiments, the one or more of targets comprises a UTR sequence a portion of a UTR sequence. In some embodiments, the one or more targets comprise non-coding RNA transcript. In some embodiments, the non-coding RNA transcript is selected from the group consisting of PASR, TASR, aTASR, TSSa-RNA, RE-RNA, uaRNA, x-ncRNA, hY RNA, usRNA, snaR, vtRNA, T-UCRs, pseudogenes, GRC-RNAs, aRNAs, PALRs, PROMPTs, and LSINCTs. In some embodiments, the one or more targets comprise an an exon-coding transcript. In some embodiments, the exon-coding transcript is an exonic sequence. In some embodiments, the probes in the set are capable of detecting an expression level of two or more targets. In some embodiments, the probes in the set are capable of detecting an expression level of three or more targets. In some embodiments the probes in the set are capable of detecting an expression level of five or more targets. In some embodiments, the probes in the set are capable of detecting an expression level of ten or more targets. In some embodiments, the probes in the set are capable of detecting an expression level of twenty or more targets. In some embodiments, the probes in the set are capable of detecting an expression level of thirty or more targets. In some embodiments, the probes in the set are capable of detecting an expression level of forty or more targets. In some embodiments, the probes in the set are capable of detecting an expression level of fifty or more targets. In some embodiments, the probes in the set are capable of detecting an expression level of sixty or more targets. In some embodiments, the probes in the set are capable of detecting an expression level of two or more targets selected from a target listed in Table 6. In some embodiments, the probes in the set are capable of detecting an expression level of three or more targets selected from a target listed in Table 6. In some embodiments, the probes in the set are capable of detecting an expression level of five or more targets selected from a target listed in Table 6. In some embodiments, the probes in the set are capable of detecting an expression level of ten or more targets selected from a target listed in Table 6. In some embodiments, the probes in the set are capable of detecting an expression level of twenty or more targets selected from a target listed in Table 6. In some embodiments, the probes in the set are capable of detecting an expression level of thirty or more targets selected from a target listed in Table 6. In some embodiments, the probes in the set are capable of detecting an expression level of two or more targets comprising a sequence selected from SEQ ID NOs: 1-153. In some embodiments, the probes in the set are capable of detecting an expression level of three or more targets comprising a sequence selected from SEQ ID NOs: 1-153. In some embodiments, the probes in the set are capable of detecting an expression level of five or more targets comprising a sequence selected from SEQ ID NOs: 1-153. In some embodiments, the probes in the set are capable of detecting an expression level of ten or more targets comprising a sequence selected from SEQ ID NOs: 1-153. In some embodiments, the probes in the set are capable of detecting an expression level of twenty or more targets comprising a sequence selected from SEQ ID NOs: 1-153. In some embodiments, the probes in the set are capable of detecting an expression level of thirty or more targets comprising a sequence selected from SEQ ID NOs: 1-153. In some embodiments, the probes in the set are capable of detecting an expression level of two or more targets comprising a sequence that is a complement of a sequence selected from SEQ ID NOs: 1-153. In some embodiments, the probes in the set are capable of detecting an expression level of three or more targets comprising a sequence that is a complement of a sequence selected from SEQ ID NOs: 1-153. In some embodiments, the probes in the set are capable of detecting an expression level of five or more targets comprising a sequence that is a complement of a sequence selected from SEQ ID NOs: 1-153. In some embodiments, the probes in the set are capable of detecting an expression level of ten or more targets comprising a sequence that is a complement of a sequence selected from SEQ ID NOs: 1-153. In some embodiments, the probes in the set are capable of detecting an expression level of twenty or more targets comprising a sequence that is a complement of a sequence selected from SEQ ID NOs: 1-153. In some embodiments, the probes in the set are capable of detecting an expression level of thirty or more targets comprising a sequence that is a complement of a sequence selected from SEQ ID NOs: 1-153. In some embodiments, the probes in the set are capable of detecting an expression level of two or more targets comprising a sequence that is a reverse complement of a sequence selected from SEQ ID NOs: 1-153. In some embodiments, the probes in the set are capable of detecting an expression level of three or more targets comprising a sequence that is a reverse complement of a sequence selected from SEQ ID NOs: 1-153. In some embodiments, the probes in the set are capable of detecting an expression level of five or more targets comprising a sequence that is a reverse complement of a sequence selected from SEQ ID NOs: 1-153. In some embodiments, the probes in the set are capable of detecting an expression level of ten or more targets comprising a sequence that is a complement of a sequence selected from SEQ ID NOs: 1-153. In some embodiments, the probes in the set are capable of detecting an expression level of twenty or more targets comprising a sequence that is a reverse complement of a sequence selected from SEQ ID NOs: 1-153. In some embodiments, the probes in the set are capable of detecting an expression level of thirty or more targets comprising a sequence that is a reverse complement of a sequence selected from SEQ ID NOs: 1-153. In some instances, the probes are between about 15 nucleotides and about 500 nucleotides in length. In some instances, the probes are between about 15 nucleotides and about 450 nucleotides in length. In some instances, the probes are between about 15 nucleotides and about 400 nucleotides in length. In some instances, the probes are between about 15 nucleotides and about 350 nucleotides in length. In some instances, the probes are between about 15 nucleotides and about 300 nucleotides in length. In some instances, the probes are between about 15 nucleotides and about 250 nucleotides in length. In some instances, the probes are between about 15 nucleotides and about 200 nucleotides in length. In some instances, the probes are at least 15 nucleotides in length. In some instances, the probes are at least 25 nucleotides in length. In some instances, the expression level determines the cancer status of the subject with at least 50% specificity. In some instances, the expression level determines the cancer status of the subject with at least 60% specificity. In some instances, the expression level determines the cancer status of the subject with at least 65% specificity. In some instances, the expression level determines the cancer status of the subject with at least 70% specificity. In some instances, the expression level determines the cancer status of the subject with at least 75% specificity. In some instances, the expression level determines the cancer status of the subject with at least 80% specificity. In some instances, the expression level determines the cancer status of the subject with at least 85% specificity.

In some embodiments, such methods involve the specific amplification of target(s) present in the test sample using methods known in the art to generate an expression profile or signature which is then compared to a reference profile or signature.

In some embodiments, the invention further provides for prognosing patient outcome, predicting likelihood of recurrence after prostatectomy and/or for designating treatment modalities.

In one embodiment, the methods generate expression profiles or signatures detailing the expression of the target sequences having altered relative expression with different cancer outcomes.

In some embodiments, the methods detect combinations of expression levels of sequences exhibiting positive and negative correlation with a disease status. In one embodiment, the methods detect a minimal expression signature.

The gene expression profiles of each of the target sequences comprising the portfolio can fixed in a medium such as a computer readable medium. This can take a number of forms. For example, a table can be established into which the range of signals (e.g., intensity measurements) indicative of disease or outcome is input. Actual patient data can then be compared to the values in the table to determine the patient samples diagnosis or prognosis. In a more sophisticated embodiment, patterns of the expression signals (e.g., fluorescent intensity) are recorded digitally or graphically.

The expression profiles of the samples can be compared to a control portfolio. The expression profiles can be used to diagnose, predict, or monitor a status or outcome of a cancer. For example, diagnosing, predicting, or monitoring a status or outcome of a cancer may comprise diagnosing or detecting a cancer, cancer metastasis, or stage of a cancer. In other instances, diagnosing, predicting, or monitoring a status or outcome of a cancer may comprise predicting the risk of cancer recurrence. Alternatively, diagnosing, predicting, or monitoring a status or outcome of a cancer may comprise predicting mortality or morbidity.

Further disclosed herein are methods for characterizing a patient population. Generally, the method comprises: (a) providing a sample from a subject; (b) assaying the expression level for a plurality of targets in the sample; and (c) characterizing the subject based on the expression level of the plurality of targets. In some instances, the method may further comprise diagnosing a cancer in the subject. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some instances, characterizing the subject comprises determining whether the subject would respond to an anti-cancer therapy. Alternatively, characterizing the subject comprises identifying the subject as a non-responder to an anti-cancer therapy. Optionally, characterizing the subject comprises identifying the subject as a responder to an anticancer therapy.

Further disclosed herein are methods for selecting a subject suffering from a cancer for enrollment into a clinical trial. Generally, the method comprises: (a) providing a sample from a subject; (b) assaying the expression level for a plurality of targets in the sample; and (c) characterizing the subject based on the expression level of the plurality of targets. In some instances, the method may further comprise diagnosing a cancer in the subject. In some embodiments, the cancer is selected from the group consisting of a carcinoma, sarcoma, leukemia, lymphoma, myeloma, and a CNS tumor. In some embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In some embodiments, the cancer is a prostate cancer. In some embodiments, the cancer is a pancreatic cancer. In some embodiments, the cancer is a bladder cancer. In some embodiments, the cancer is a thyroid cancer. In some embodiments, the cancer is a lung cancer. In some instances, characterizing the subject comprises determining whether the subject would respond to an anti-cancer therapy. Alternatively, characterizing the subject comprises identifying the subject as a non-responder to an anti-cancer therapy. Optionally, characterizing the subject comprises identifying the subject as a responder to an anti-cancer therapy.

EXAMPLES

Example 1. Whole-Transcriptome Profiling in Thyroid Cancer Diagnostics

The objective of this study was to determine whether whole-transcriptome (exon array) profiling could be utilized to identify novel biomarkers that allow for accurate thyroid cancer diagnosis.

Materials and Methods

Tissue Specimens

One hundred and twenty-five (125) specimens consisting of 60 formalin-fixed paraffin embedded (FFPE) surgical samples and 65 FFPE fine needle aspiration biopsy (FNAB) cell pellets of human thyroid nodular disease were retrospectively collected from patients treated at St. Paul's Hospital (Vancouver, BC, Canada) in accordance with an institutional review board-approved protocol. For a subset of 8 surgical specimens matched FNAB cell pellets were also available. For surgical specimens, a tissue microarrayer (Beecher Instruments, Silver Spring, Md.) was used to core each FFPE surgical specimen once with a 1.0 mm diameter cylinder punches ('FFPE cores'). Cell blocks were prepared by spinning down the FNAB, followed by formalin-fixation and embedding in paraffin. From cell blocks, 3 ten micron sections were obtained using a Lecia microtome. Samples were divided into two subsets consisting of a training cohort of surgical specimens for feature selection and model building (n=60) and a validation cohort of FNA cell block specimens (n=65) for validation of the model. Table 1 shows the composition of the subsets including their original cytology diagnosis (according to 2007 Bethesda classification scheme) as well as their 'gold-standard' pathological diagnosis. Pathology and cytology diagnoses were made through independent review by 2 pathologists. Any disagreements were resolved through discussion.

TABLE 1

| Subset | Specimens obtained for this study | |
|---|---|---|
| | Training | Validation |
| Specimen Type | Thyroidectomy | FNAB |
| Total Number | 60 | 65 |
| Specimens passed RNA QC | 60 | 56 |
| Specimens passed array QC | 57 | 31 |

RNA Extraction

RNA was extracted and purified from the FFPE cores using a modified protocol for the commercially available Formapure nucleic acid extraction kit (Agencourt Biosciences, Beverly Mass.). Principal modifications to the kit protocol included preheating the lysis buffer to 70° C. before immersing the FFPE sections in lysis buffer and subjecting FFPE lysates to incubation at 99° C. for 1 min. In addition, FFPE samples were incubated with Proteinase K (20 ul of 40 mg/mL) for 16 hrs in a water bath at 55° C. RNA was further purified using DNAse I treatment (Ambion, Austin, Tex.) to eliminate any contaminating DNA. RNA was eluted with 300 ul of RNAse-free water and subsequently concentrated and purified using sodium acetate precipitation and a series of ethanol washes and resuspended in 15 ul of water. RNA concentrations were calculated using a Nanodrop ND-1000 spectrophotometer (Nanodrop Technologies, Rockland, Del.). These additional purification steps significantly improved the yield of amplified material in subsequent steps described below (data not shown). Sufficient RNA (75 ng) was obtained using these procedures from all 60 FFPE cores and 56/65 FNA cell block specimens.

Nucleic Acid Amplification and GeneChip Hybridization

Purified RNA was subjected to whole-transcriptome amplification using the WT-Ovation FFPE system including the WT-Ovation Exon and FL-Ovation Biotin V2 labeling modules (NuGEN Technologies, San Carlos, Calif.), with the following modifications. Seventy-five (75) nanograms of RNA extracted from FFPE cores or FNA cell blocks was used to generate amplified Ribo-SPIA product. For the WT-Ovation Exon sense-target strand conversion kit 4 ug of Ribo-SPIA product were used. Additionally, four micrograms of WT-Ovation Exon product were used to fragment and label using the FL-Ovation Biotin V2 labeling module and labeled product was hybridized to Affymetrix Human Exon 1.0 ST GeneChips following manufacturer's recommendations (Affymetrix, Santa Clara, Calif.).

Microarray Analysis

Affymetrix.CEL files we first subjected to chip quality control (QC) filters using Affymetrix Power Tools. Chip QC was performed using two quality control metrics, the area under the curve metric (AUC) comparing positive vs negative controls setting a pass threshold of pos_vs_neg AUC of ≥0.56 and a GNUSE value of 1+/−0.2 (1 SD) SD. (McCall reference). From the training cohort of surgical specimens 57/60 samples passed chip QC whereas from the validation cohort of FNA specimens only 31/56 passed chip QC. Probe set modeling and data pre-processing were derived using the fRMA algorithm. Batch variability was corrected using the ComBat algorithm. From the ~1.4M probes sets on the array, 1.1M were kept after filtering for cross-hybridization. Feature selection was pursued using a bootstrapped t-test over 1,000 iterations keeping those features with p<0.001 across all iterations. A two-way normalization across samples and across features was applied on the final feature list matrix.

KNN Classifier

The classifier was generated using the k-nearest neighbor algorithm with a tuned k value of 7. Detailed description of the implementation can be found in the Supplementary Methods (Source: The Elements of Statistical Learning Data Mining, Inference, and Prediction. Second Edition, February 2009).

Results

FFPE Thyroidectomy Expression Analysis

The final study cohort was composed of specimens from 48 benign thyroid lesions and 40 thyroid cancers. The cohort was divided into a training subset comprised of FFPE thyroidectomy specimens (n=57, used to select features, build the classifier, optimize the tuning parameters and set the cut-points) and a validation subset of FFPE FNA cell blocks (n=31, used to evaluate the classifier model). Clinical and pathologic characteristics for the entire cohort and more detailed cancer patient data are summarized in Table 2.

TABLE 2

Sample Characteristics

| Subset | | Training | Validation |
|---|---|---|---|
| FNA Dx | Benign | 15 | 6 |
| | Suspicious for Cancer/indeterminate | 28 | 14 |
| | Malignant | 14 | 11 |
| Path Review Dx | Benign | 30 | 18 |
| | Malignant | 27 | 13 |
| Bethesda Score | Unsatisfactory | NA | 0 |
| | Benign | NA | 3 |
| | Atypia of Undetermined Significance | NA | 1 |
| | Suspicious for a Follicular Neoplasm | NA | 13 |
| | Suspicious for Malignancy | NA | 0 |
| | Malignant | NA | 12 |
| | Cyst fluid only | NA | 2 |
| Histology Final Diagnosis | Goiter | 15 | 5 |
| | Thyroiditis | 1 | 0 |
| | Hashimoto's Disease | 1 | 0 |
| | Hurthle Cell Adenoma | 4 | 6 |
| | Follicular Adenoma | 9 | 6 |
| | Adenoma | 0 | 1 |
| | Follicular Carcinoma | 6 | 0 |
| | Papillary Carcinoma | 21 | 13 |

Unsupervised clustering of training subset samples using principal component analysis (PCA plots shows some separation of benign (red dots) and malignant (blue dots) thyroid nodule disease, with samples clustering according to their final pathology diagnosis (FIG. 1A). In FIG. 1B, an overlay of the initial FNA diagnosis is shown with the indeterminate cytology samples highlighted in green. Indeterminate FNA diagnoses were distributed between the benign and malignant clusters. In contrast, unsupervised PCA analysis of the validation subset of samples, which were from FFPE FNA cytology (cell pellet) specimens, fails to show clear separation of the final pathology diagnosis or initial FNA diagnosis (FIGS. 1B and 1C). This unsupervised analysis suggests that the transcriptional profiles of pathologically confirmed benign and malignant lesions are very distinct and can be easily resolved in tissue specimens although not in FNAB cell pellet specimens.

In order to identify expressed markers for building of a classifier, we performed supervised differential expression analysis on the training subset (Table 3). Using a reiterative bootstrapping procedure with t-tests for significance (p<0.001, see methods for further details) we identified a final set of 92 and 157 probesets at increased expression in pathologically confirmed malignant and benign samples, respectively. FIG. 2A shows a heatmap from two-way hierarchical clustering of the 57 training samples and 249 probesets. The samples are divided among two branches of the dendrogram, the left branch (n=23) contains only malignant samples, while the right branch (n=34) contains all the benign samples and one malignant (an indeterminate FNAB cytology with a final pathological diagnosis of follicular carcinoma) sample. FIG. 2B shows a heatmap from two-way hierarchical clustering of the 31 validation samples and 249 probesets (subset of the 249 probeset sequences shown in Table 7). Using hierarchical clustering with the 249 probesets in the 31 sample FNAB cell pellet validation subset, the clustering wasn't as dichotomous. There were three main branches in the dendrogram, the first (from left to right) contained group of six malignant samples, the second a cluster consisted of ten benign samples and the third branch, a mix of malignant and benign samples. (FIG. 2C shows the heatmap of the indeterminate subset of the Validation subset). Applying a supervised clustering using multi-dimensional scaling (MDS) shows the similarity of the expression profiles of the 249-marker RNA expression signature between samples. FIG. 3A shows clear separation in the training samples (malignant in blue, benign in red dots) thyroid nodular disease. In FIG. 3B an overlay of their preoperative FNAB diagnosis is shown with the specimens with an indeterminate cytological diagnosis highlighted in blue (cancer (green), benign (red)). On the other hand the supervised clustering of the validation samples is less pronounced of the final histopathological diagnosis or initial FNAB diagnosis (FIG. 3 C and FIG. 3 D) than the Training subset.

TABLE 3

Differentially expressed features in the training subset

| | p < 0.001 | FDR < 0.05 | MFD ≥ 2 | MFD ≥ 2 and u ≥ 100 | t-test p = 0.001* |
|---|---|---|---|---|---|
| Malignant > Benign | 83687 | 10473 | 4836 | 2141 | 92 |
| Benign > Malignant | 65964 | 9094 | 11288 | 5311 | 157 |
| Total | 149651 | 19567 | 16124 | 7452 | 249 |

*features under bootstrapping 1000 iterations

KNN Classifier Analysis

In order to develop a classifier with potential clinical applicability, used the k-nearest neighbor algorithm) on the training set and applied the classifier to an independent validation set of FNA biopsy cell pellets (also FFPE). The KNN classifier assigns a probability for a given sample of being benign and malignant for each probeset in the model, returning an overall probability of a sample being malignant. Using receiver-operator characteristic curves, we found that the KNN 249-probeset classifier showed an AUC of 0.99 and 0.96 in the training and validation subsets, respectively (FIG. 4). We determined a cut-point in the training subset by maximizing the product of the sensitivity and specificity along the ROC curve for classification of benign and malignant disease. Overall the KNN 249-probeset classifier showed an accuracy of 0.93 and 0.90 in the training and validation subsets, respectively (Table 4). A sample-by-sample performance of the classifier together with observed and predicted labels can be seen in Table 5. In the training subset, 3 malignant samples (one of which that co-clustered with benign samples in FIG. 2A) were misclassified by the classifier resulting in a false-negative call. In the validation subset, 3 samples with a pathology review diagnosis of malignant were misclassified as benign. All three of these specimens were diagnosed as cancer by FNAB and were confirmed to be papillary carcinoma after histopathological review.

TABLE 4

Truth Table
249-marker set

A-Training Subset

| | | KNN | |
|---|---|---|---|
| | | Negative | Positive |
| Pathology Final Diagnosis | Benign | 30 | 4 |
| | Malignant | 0 | 23 |
| | AUC: | 0.998 | |
| | Accuracy: | 0.93 | |
| | 95% CI: | (0.83-0.98) | |
| | PPV | 100.0% | |
| | NPV | 88.2% | |
| | SENSITIVITY | 85.2% | |
| | SPECIFICITY | 100.0% | |

B-Validation SubSet

| | | KNN | |
|---|---|---|---|
| | | Negative | Positive |
| Pathology Final Diagnosis | Benign | 18 | 3 |
| | Malignant | 0 | 10 |
| | AUC: | 0.962 | |
| | Accuracy: | 0.903 | |
| | 95% CI: | (0.743-0.98) | |
| | PPV | 100.0% | |
| | NPV | 85.7% | |
| | SENSITIVITY | 76.9% | |
| | SPECIFICITY | 100.0% | |

Example 2. Method of Diagnosing a Leukemia in a Subject

A subject arrives at a doctor's office and complains of symptoms including bone and joint pain, easy bruising, and fatigue. The doctor examines the subject and also notices that the subject's lymph nodes are also swollen. Bone marrow and blood samples are obtained from the subject. The expression levels of ten targets selected from Table 6 are obtained by microarray analysis of the samples. Aberrant expression of the targets is observed and the subject is diagnosed with acute lymphoblastic leukemia.

Example 3. Method of Determining a Treatment for Breast Cancer in a Subject

A subject is diagnosed with breast cancer. A tissue sample is obtained from the subject. Nucleic acids are isolated from the tissue sample and the nucleic acids are applied to a probe set comprising at least twenty probes capable of detecting the expression of twenty targets selected from Table 7. Analysis of the expression level of the targets reveals the subject has a tamoxifen-resistant breast cancer and gefitinib is recommended as an alternative therapy.

Example 4. Method of Determining the Prognosis a Pancreatic Cancer in a Subject A subject is diagnosed with pancreatic cancer. A tissue sample is obtained from the subject. The tissue sample is assayed for the expression level of biomarkers comprising thirty targets selected from Table 6. Based on the expression level of the targets, it is determined that the pancreatic cancer has a high risk of recurrence.

Example 5. Method of Diagnosing a Prostate Cancer in a Subject

A subject arrives at a doctor's office and complains of symptoms including inability to urinate standing up, blood in urine, and dull, incessant pain in the pelvis and lower back. The doctor conducts a digital prostate exam and recommends that blood samples are obtained from the subject. The PSA is abnormal, a biopsy is ordered and microarray analysis of the blood and tissue samples obtained from the subject reveal aberrant expression of fifteen targets selected from Tables 6-7 and the subject is diagnosed with prostate cancer.

Example 6. Method of Modifying a Therapeutic Regimen for Lung Cancer in a Subject A subject is diagnosed with non-small cell lung cancer (NSCLC). Multiple tissue samples are obtained from the subject, one sample prior to treatment (e.g., pre-treatment sample) and one sample two weeks after treatment with cisplatin (e.g., post-treatment sample). Nucleic acids are isolated from the tissue samples and the nucleic acids are applied to a probe set comprising five probes capable of detecting the expression of five targets selected from Tables 6-7. Comparison of the expression level of the targets from pre-treatment sample and post-treatment sample reveals that the subject is non-responsive to cisplatin therapy and gemcitabine is recommended as an alternative therapy.

TABLE 5

| Specimen | Study | Tissue Type | KNN249 Score | Predicted Class | Path Dx | Bethesda Score | FNA Dx | Histology Dx | Secondary Dx | Sex | Age | QC |
|---|---|---|---|---|---|---|---|---|---|---|---|---|
| T007-A-HuEx-1_0-st-v2-01-1_10.CEL | Val | Cell Block | 0.00 | Benign | Ben | Sus Follicular | Benign | Goiter | none | F | 39 | Pass |
| T008-A-HuEx-1_0-st-v2-01-1_11.CEL | Val | Cell Block | 0.00 | Benign | Ben | Benign | Benign | Goiter | Hyperplastic Nodule | F | 37 | Pass |
| T009-A-HuEx-1_0-st-v2-01-1_12.CEL | Val | Cell Block | 0.00 | Benign | Ben | Sus Follicular | IND | Hurthle Cell Adenoma | Goiter | F | 47 | Pass |

TABLE 5-continued

| Specimen | Study | Tissue Type | KNN249 Score | Predicted Class | Path Dx | Bethesda Score | FNA Dx | Histology Dx | Secondary Dx | Sex | Age | QC |
|---|---|---|---|---|---|---|---|---|---|---|---|---|
| W145-HuEx-1_0-st-v2-01-1_3.CEL | Val | Cell Block | 0.00 | Benign | Ben | Sus Follicular | IND | Hurthle Cell Adenoma | none | NA | 56 | Pass |
| W162-HuEx-1_0-st-v2-01-1_19.CEL | Val | Cell Block | 0.00 | Benign | Ben | Sus Follicular | IND | Follicular Adenoma | none | NA | 24 | Pass |
| W179-HuEx-1_0-st-v2-01-1_33.CEL | Val | Cell Block | 0.14 | Benign | Ben | Sus Follicular | IND | Hurthle Cell Adenoma | none | NA | 68 | Pass |
| W193-HuEx-1_0-st-v2-01-1_47.CEL | Val | Cell Block | 0.14 | Benign | Ben | Sus Follicular | IND | Follicular Adenoma | none | NA | 36 | Pass |
| W194-HuEx-1_0-st-v2-01-1_48.CEL | Val | Cell Block | 0.14 | Benign | Ben | Sus Follicular | IND | Follicular Adenoma | none | NA | 67 | Pass |
| W146-HuEx-1_0-st-v2-01-1_4.CEL | Val | Cell Block | 0.29 | Benign | Ben | Benign | Benign | Goiter | none | NA | 35 | Pass |
| W147-HuEx-1_0-st-v2-01-1_5.CEL | Val | Cell Block | 0.29 | Benign | Ben | Sus Follicular | IND | Adenoma | none | NA | 49 | Pass |
| W157-HuEx-1_0-st-v2-01-1_14.CEL | Val | Cell Block | 0.29 | Benign | Ben | Sus Follicular | IND | Hurthle Cell Adenoma | none | NA | 67 | Pass |
| W186-HuEx-1_0-st-v2-01-1_40.CEL | Val | Cell Block | 0.29 | Benign | Ben | Cyst | Benign | Goiter | none | NA | 40 | Pass |
| W144-HuEx-1_0-st-v2-01-1_2.CEL | Val | Cell Block | 0.43 | Malignant | Ben | Sus Follicular | IND | Follicular Adenoma | none | NA | 45 | Pass |
| W152-HuEx-1_0-st-v2-01-1_10.CEL | Val | Cell Block | 0.43 | Malignant | Ben | Sus Follicular | IND | Follicular Adenoma | none | NA | 38 | Pass |
| W153-HuEx-1_0-st-v2-01-1_11A.CEL | Val | Cell Block | 0.43 | Malignant | Ben | AUS | IND | Hurthle Cell Adenoma | none | NA | 33 | Pass |
| W156-HuEx-1_0-st-v2-01-1_13.CEL | Val | Cell Block | 0.43 | Malignant | Ben | Sus Follicular | IND | Follicular Adenoma | none | NA | 82 | Pass |
| W158-HuEx-1_0-st-v2-01-1_15.CEL | Val | Cell Block | 0.43 | Malignant | Ben | Sus Follicular | IND | Hurthle Cell Adenoma | none | NA | 43 | Pass |
| W159-HuEx-1_0-st-v2-01-1_16.CEL | Val | Cell Block | 0.43 | Malignant | Ben | Benign | Benign | Goiter | none | NA | 57 | Pass |
| W148-HuEx-1_0-st-v2-01-1_6.CEL | Val | Cell Block | 0.43 | Malignant | Mal | Mal | Cancer | Papillary Carcinoma | none | NA | 28 | Pass |
| W151-HuEx-1_0-st-v2-01-1_9.CEL | Val | Cell Block | 0.43 | Malignant | Mal | Mal | Cancer | Papillary Carcinoma | none | NA | 23 | Pass |
| W155-HuEx-1_0-st-v2-01-1_12.CEL | Val | Cell Block | 0.43 | Malignant | Mal | Mal | Cancer | Papillary Carcinoma | none | NA | 50 | Pass |
| W164-HuEx-1_0-st-v2-01-1_21.CEL | Val | Cell Block | 0.57 | Malignant | Mal | Mal | Cancer | Papillary Carcinoma | none | NA | 36 | Pass |
| W149-HuEx-1_0-st-v2-01-1_7.CEL | Val | Cell Block | 0.71 | Malignant | Mal | Cyst | Benign | Papillary Carcinoma | none | NA | 25 | Pass |
| W196-HuEx-1_0-st-v2-01-1_50.CEL | Val | Cell Block | 0.71 | Malignant | Mal | Mal | Cancer | Papillary Carcinoma | none | NA | 33 | Pass |
| W197-HuEx-1_0-st-v2-01-1_51.CEL | Val | Cell Block | 0.71 | Malignant | Mal | Mal | Cancer | Papillary Carcinoma | none | NA | 71 | Pass |
| S997-A-HuEx-1_0-st-v2-01-1_1.CEL | Val | Cell Block | 1.00 | Malignant | Mal | Mal | Cancer | Papillary Carcinoma | Thyroiditis | F | 27 | Pass |
| S998-A-HuEx-1_0-st-v2-01-1_2.CEL | Val | Cell Block | 1.00 | Malignant | Mal | Mal | Cancer | Papillary Carcinoma | Goiter | F | 36 | Pass |

TABLE 5-continued

| Specimen | Study | Tissue Type | KNN249 Score | Predicted Class | Path Dx | Bethesda Score | FNA Dx | Histology Dx | Secondary Dx | Sex | Age | QC |
|---|---|---|---|---|---|---|---|---|---|---|---|---|
| T002-A-HuEx-1_0-st-v2-01-1_5.CEL | Val | Cell Block | 1.00 | Malignant | Mal | Mal | Cancer | Papillary Carcinoma | none | F | 30 | Pass |
| T003-A-HuEx-1_0-st-v2-01-1_6.CEL | Val | Cell Block | 1.00 | Malignant | Mal | Mal | Cancer | Papillary Carcinoma | Hashimoto's | F | 29 | Pass |
| T004-A-HuEx-1_0-st-v2-02-1_7.CEL | Val | Cell Block | 1.00 | Malignant | Mal | Mal | Cancer | Papillary Carcinoma | none | F | 41 | Pass |
| W175-HuEx-1_0-st-v2-01-1_30A.CEL | Val | Cell Block | 1.00 | Malignant | Mal | Mal | IND | Papillary Carcinoma | none | NA | 68 | Pass |
| P109-A-HuEx-1_0-st-v2-01-1_1A.CEL | Train | TMA Core | 0.00 | Benign | Ben | NA | IND | Follicular Adenoma | none | M | 51 | Pass |
| P111-A-HuEx-1_0-st-v2-01-1_3B.CEL | Train | TMA Core | 0.00 | Benign | Ben | NA | IND | Follicular Adenoma | Goiter | F | 36 | Pass |
| P113-A-HuEx-1_0-st-v2-01-1_5C.CEL | Train | TMA Core | 0.00 | Benign | Ben | NA | IND | Follicular Adenoma | Hashimoto's | F | 39 | Pass |
| P115-A-HuEx-1_0-st-v2-01-1_7D.CEL | Train | TMA Core | 0.00 | Benign | Ben | NA | IND | Follicular Adenoma | none | F | 47 | Pass |
| R033-A-HuEx-1_0-st-v2-01-1_19.CEL | Train | TMA Core | 0.00 | Benign | Ben | NA | IND | Follicular Adenoma | none | F | 44 | Pass |
| R034-A-HuEx-1_0-st-v2-01-1_20.CEL | Train | TMA Core | 0.00 | Benign | Ben | NA | IND | Hurthle Cell Adenoma | none | F | 44 | Pass |
| R035-A-HuEx-1_0-st-v2-01-1_21.CEL | Train | TMA Core | 0.00 | Benign | Ben | NA | IND | Follicular Adenoma | none | F | 47 | Pass |
| R036-A-HuEx-1_0-st-v2-01-1_22.CEL | Train | TMA Core | 0.00 | Benign | Ben | NA | IND | Goiter | none | F | 42 | Pass |
| R037-A-HuEx-1_0-st-v2-02-1_23.CEL | Train | TMA Core | 0.00 | Benign | Ben | NA | Benign | Goiter | none | F | 39 | Pass |
| R038-A-HuEx-1_0-st-v2-01-1_24.CEL | Train | TMA Core | 0.00 | Benign | Ben | NA | Benign | Goiter | none | F | 58 | Pass |
| R039-A-HuEx-1_0-st-v2-01-1_25.CEL | Train | TMA Core | 0.00 | Benign | Ben | NA | Benign | Goiter | none | F | 25 | Pass |
| R040-A-HuEx-1_0-st-v2-02-1_26.CEL | Train | TMA Core | 0.00 | Benign | Ben | NA | Benign | Goiter | none | F | 27 | Pass |
| R042-A-HuEx-1_0-st-v2-02-1_28.CEL | Train | TMA Core | 0.00 | Benign | Ben | NA | IND | Follicular Adenoma | none | F | 20 | Pass |
| R043-A-HuEx-1_0-st-v2-01-1_29.CEL | Train | TMA Core | 0.00 | Benign | Ben | NA | Benign | Goiter | none | F | 31 | Pass |
| R044-A-HuEx-1_0-st-v2-01-1_30.CEL | Train | TMA Core | 0.00 | Benign | Ben | NA | Benign | Goiter | none | F | 39 | Pass |

TABLE 5-continued

| Specimen | Study | Tissue Type | KNN249 Score | Predicted Class | Path Dx | Bethesda Score | FNA Dx | Histology Dx | Secondary Dx | Sex | Age | QC |
|---|---|---|---|---|---|---|---|---|---|---|---|---|
| R045-A-HuEx-1_0-st-v2-01-1_31.CEL | Train | TMA Core | 0.00 | Benign | Ben | NA | Benign | Goiter | none | F | 38 | Pass |
| R046-A-HuEx-1_0-st-v2-01-1_32.CEL | Train | TMA Core | 0.00 | Benign | Ben | NA | IND | Thyroiditis | none | M | 70 | Pass |
| R047-A-HuEx-1_0-st-v2-01-1_33.CEL | Train | TMA Core | 0.00 | Benign | Ben | NA | IND | Hurthle Cell Adenoma | none | F | 47 | Pass |
| R048-A-HuEx-1_0-st-v2-02-1_34.CEL | Train | TMA Core | 0.00 | Benign | Ben | NA | Benign | Goiter | none | F | 61 | Pass |
| R049-A-HuEx-1_0-st-v2-01-1_35.CEL | Train | TMA Core | 0.00 | Benign | Ben | NA | IND | Hurthle Cell Adenoma | none | F | 32 | Pass |
| R050-A-HuEx-1_0-st-v2-01-1_36.CEL | Train | TMA Core | 0.00 | Benign | Ben | NA | Benign | Goiter | none | F | 55 | Pass |
| R051-A-HuEx-1_0-st-v2-01-1_37.CEL | Train | TMA Core | 0.00 | Benign | Ben | NA | Benign | Goiter | none | F | 43 | Pass |
| R052-A-HuEx-1_0-st-v2-02-1_38.CEL | Train | TMA Core | 0.00 | Benign | Ben | NA | Benign | Goiter | Hyperplastic Nodule | F | 37 | Pass |
| R053-A-HuEx-1_0-st-v2-01-1_39.CEL | Train | TMA Core | 0.00 | Benign | Ben | NA | Benign | Goiter | none | F | 41 | Pass |
| R054-A-HuEx-1_0-st-v2-01-1_40.CEL | Train | TMA Core | 0.00 | Benign | Ben | NA | IND | Hurthle Cell Adenoma | Goiter | F | 47 | Pass |
| R055-A-HuEx-1_0-st-v2-01-1_41.CEL | Train | TMA Core | 0.00 | Benign | Ben | NA | Benign | Hashimoto's | none | M | 48 | Pass |
| R056-A-HuEx-1_0-st-v2-01-1_42.CEL | Train | TMA Core | 0.00 | Benign | Ben | NA | Benign | Goiter | none | F | 39 | Pass |
| P117-A-HuEx-1_0-st-v2-01-1_9E.CEL | Train | TMA Core | 0.14 | Benign | Ben | NA | IND | Follicular Adenoma | none | F | 40 | Pass |
| R032-A-HuEx-1_0-st-v2-01-1_18.CEL | Train | TMA Core | 0.14 | Benign | Ben | NA | Benign | Goiter | Thyroiditis | F | 52 | Pass |
| R041-A-HuEx-1_0-st-v2-01-1_27.CEL | Train | TMA Core | 0.14 | Benign | Ben | NA | IND | Follicular Adenoma | none | F | 27 | Pass |
| P127-A-HuEx-1_0-st-v2-01-1_19J.CEL | Train | TMA Core | 0.14 | Benign | Mal | NA | IND | Follicular Carcinoma | none | F | 75 | Pass |
| R029-A-HuEx-1_0-st-v2-01-1_15.CEL | Train | TMA Core | 0.43 | Malignant | Mal | NA | IND | Papillary Carcinoma | Goiter | F | 51 | Pass |
| R057-A-HuEx-1_0-st-v2-01-1_43.CEL | Train | TMA Core | 0.43 | Malignant | Mal | NA | IND | Follicular Carcinoma | none | M | 28 | Pass |
| R058-A-HuEx-1_0-st-v2-02-1_44.CEL | Train | TMA Core | 0.43 | Malignant | Mal | NA | IND | Follicular Carcinoma | Micropapillary Carcinoma | F | 47 | Pass |

TABLE 5-continued

| Specimen | Study | Tissue Type | KNN249 Score | Predicted Class | Path Dx | Bethesda Score | FNA Dx | Histology Dx | Secondary Dx | Sex | Age | QC |
|---|---|---|---|---|---|---|---|---|---|---|---|---|
| R059-A-HuEx-1_0-st-v2-01-1_45.CEL | Train | TMA Core | 0.86 | Malignant | Mal | NA | IND | Follicular Carcinoma | none | F | 33 | Pass |
| P119-A-HuEx-1_0-st-v2-01-1_11F.CEL | Train | TMA Core | 1.00 | Malignant | Mal | NA | IND | Follicular Carcinoma | none | F | 43 | Pass |
| P121-A-HuEx-1_0-st-v2-01-1_13G.CEL | Train | TMA Core | 1.00 | Malignant | Mal | NA | IND | Follicular Carcinoma | none | M | 59 | Pass |
| P123-A-HuEx-1_0-st-v2-01-1_15H.CEL | Train | TMA Core | 1.00 | Malignant | Mal | NA | IND | Papillary Carcinoma | Hashimoto's | F | 46 | Pass |
| P125-A-HuEx-1_0-st-v2-01-1_17I.CEL | Train | TMA Core | 1.00 | Malignant | Mal | NA | IND | Papillary Carcinoma | Thyroiditis | F | 48 | Pass |
| R015-A-HuEx-1_0-st-v2-01-1_1.CEL | Train | TMA Core | 1.00 | Malignant | Mal | NA | Cancer | Papillary Carcinoma | Hashimoto's | F | 47 | Pass |
| R016-A-HuEx-1_0-st-v2-01-1_2.CEL | Train | TMA Core | 1.00 | Malignant | Mal | NA | Cancer | Papillary Carcinoma | Thyroiditis | F | 27 | Pass |
| R017-A-HuEx-1_0-st-v2-02-1_3.CEL | Train | TMA Core | 1.00 | Malignant | Mal | NA | Cancer | Papillary Carcinoma | Goiter | F | 36 | Pass |
| R018-A-HuEx-1_0-st-v2-01-1_4.CEL | Train | TMA Core | 1.00 | Malignant | Mal | NA | Cancer | Papillary Carcinoma | Follicular | F | 25 | Pass |
| R019-A-HuEx-1_0-st-v2-01-1_5.CEL | Train | TMA Core | 1.00 | Malignant | Mal | NA | Cancer | Papillary Carcinoma | none | F | 42 | Pass |
| R021-A-HuEx-1_0-st-v2-01-1_7.CEL | Train | TMA Core | 1.00 | Malignant | Mal | NA | Cancer | Papillary Carcinoma | Hashimoto's | M | 21 | Pass |
| R022-A-HuEx-1_0-st-v2-01-1_8.CEL | Train | TMA Core | 1.00 | Malignant | Mal | NA | Cancer | Papillary Carcinoma | Hurthle cell | F | 60 | Pass |
| R023-A-HuEx-1_0-st-v2-01-1_9.CEL | Train | TMA Core | 1.00 | Malignant | Mal | NA | Cancer | Papillary Carcinoma | none | M | 53 | Pass |
| R024-A-HuEx-1_0-st-v2-01-1_10.CEL | Train | TMA Core | 1.00 | Malignant | Mal | NA | Cancer | Papillary Carcinoma | Follicular | F | 39 | Pass |
| R025-A-HuEx-1_0-st-v2-01-1_11.CEL | Train | TMA Core | 1.00 | Malignant | Mal | NA | Cancer | Papillary Carcinoma | none | M | 45 | Pass |
| R026-A-HuEx-1_0-st-v2-01-1_12.CEL | Train | TMA Core | 1.00 | Malignant | Mal | NA | Cancer | Papillary Carcinoma | Hashimoto's | F | 29 | Pass |
| R027-A-HuEx-1_0-st-v2-01-1_13.CEL | Train | TMA Core | 1.00 | Malignant | Mal | NA | Cancer | Papillary Carcinoma | none | F | 41 | Pass |
| R028-A-HuEx-1_0-st-v2-01-1_14.CEL | Train | TMA Core | 1.00 | Malignant | Mal | NA | Cancer | Papillary Carcinoma | Follicular | F | 65 | Pass |
| R030-A-HuEx-1_0-st-v2-01-1_16.CEL | Train | TMA Core | 1.00 | Malignant | Mal | NA | Cancer | Papillary Carcinoma | none | F | 55 | Pass |

TABLE 5-continued

| Specimen | Study | Tissue Type | KNN249 Score | Predicted Class | Path Dx | Bethesda Score | FNA Dx | Histology Dx | Secondary Dx | Sex | Age | QC |
|---|---|---|---|---|---|---|---|---|---|---|---|---|
| R031-A-HuEx-1_0-st-v2-01-1_17.CEL | Train | TMA Core | 1.00 | Malignant | Mal | NA | IND | Papillary Carcinoma | Goiter | F | 46 | Pass |
| R060-A-HuEx-1_0-st-v2-02-1_46.CEL | Train | TMA Core | 1.00 | Malignant | Mal | NA | IND | Papillary Carcinoma | Hashimoto's | F | 41 | Pass |
| R061-A-HuEx-1_0-st-v2-01-1_47.CEL | Train | TMA Core | 1.00 | Malignant | Mal | NA | IND | Papillary Carcinoma | Hashimoto's | F | 60 | Pass |
| R064-A-HuEx-1_0-st-v2-01-1_50.CEL | Train | TMA Core | 1.00 | Malignant | Mal | NA | IND | Papillary Carcinoma | none | M | 40 | Pass |
| R020-A-HuEx-1_0-st-v2-01-1_6.CEL | Train | TMA Core | Failed QC | | Mal | NA | Cancer | Papillary Carcinoma | none | F | 30 | Fail |
| R062-A-HuEx-1_0-st-v2-01-1_48.CEL | Train | TMA Core | Failed QC | | Mal | NA | IND | Papillary Carcinoma | Hashimoto's | F | 59 | Fail |
| R063-A-HuEx-1_0-st-v2-01-1_49.CEL | Train | TMA Core | Failed QC | | Mal | NA | IND | Papillary Carcinoma | Follicular | F | 15 | Fail |
| W163-HuEx-1_0-st-v2-01-1_20.CEL | Val | Cell Block | Failed QC | | Mal | Sus Mal | IND | Papillary Carcinoma | none | NA | 33 | Fail |
| W166-HuEx-1_0-st-v2-01-1_23.CEL | Val | Cell Block | Failed QC | | Mal | Mal | Cancer | Papillary Carcinoma | none | NA | 57 | Fail |
| W167-HuEx-1_0-st-v2-01-1_24.CEL | Val | Cell Block | Failed QC | | Mal | Sus Follicular | IND | Hurthle Cell Carcinoma | none | NA | 70 | Fail |
| W176-HuEx-1_0-st-v2-01-1_30B.CEL | Val | Cell Block | Failed QC | | Mal | Mal | IND | Papillary Carcinoma | none | NA | 69 | Fail |
| W177-HuEx-1_0-st-v2-01-1_31.CEL | Val | Cell Block | Failed QC | | Mal | Mal | Cancer | Papillary Carcinoma | none | NA | 49 | Fail |
| W180-HuEx-1_0-st-v2-01-1_34.CEL | Val | Cell Block | Failed QC | | Mal | Mal | Cancer | Papillary Carcinoma | none | NA | 45 | Fail |
| W181-HuEx-1_0-st-v2-01-1_35.CEL | Val | Cell Block | Failed QC | | Mal | Mal | Cancer | Papillary Carcinoma | none | NA | 47 | Fail |
| W184-HuEx-1_0-st-v2-01-1_38.CEL | Val | Cell Block | Failed QC | | Mal | Sus Mal | Cancer | Papillary Carcinoma | none | NA | 68 | Fail |
| W185-HuEx-1_0-st-v2-01-1_39.CEL | Val | Cell Block | Failed QC | | Mal | Mal | Cancer | Papillary Carcinoma | none | NA | 46 | Fail |
| W189-HuEx-1_0-st-v2-01-1_43.CEL | Val | Cell Block | Failed QC | | Mal | Mal | Cancer | Papillary Carcinoma | none | NA | 49 | Fail |
| W192-HuEx-1_0-st-v2-01-1_46.CEL | Val | Cell Block | Failed QC | | Mal | Mal | Cancer | Papillary Carcinoma | none | NA | 34 | Fail |
| W198-HuEx-1_0-st-v2-01-1_52.CEL | Val | Cell Block | Failed QC | | Mal | Mal | Cancer | Papillary Carcinoma | none | NA | 74 | Fail |
| W143-HuEx-1_0-st-v2-01-1_1.CEL | Val | Cell Block | Failed QC | | Ben | Sus Follicular | IND | Hurthle Cell Adenoma | none | NA | 80 | Fail |
| W150-HuEx-1_0-st-v2-01-1_8.CEL | Val | Cell Block | Failed QC | | Ben | Benign | Benign | Follicular Adenoma | none | NA | 53 | Fail |
| W154-HuEx-1_0-st-v2-01-1_11B.CEL | Val | Cell Block | Failed QC | | Ben | AUS | IND | Hurthle Cell Adenoma | none | NA | 34 | Fail |
| W160-HuEx-1_0-st-v2-01-1_17.CEL | Val | Cell Block | Failed QC | | Ben | Benign | Benign | Goiter | none | NA | 44 | Fail |

TABLE 5-continued

| Specimen | Study | Tissue Type | KNN249 Score | Predicted Class | Path Dx | Bethesda Score | FNA Dx | Histology Dx | Secondary Dx | Sex | Age | QC |
|---|---|---|---|---|---|---|---|---|---|---|---|---|
| W168-HuEx-1_0-st-v2-01-1_25.CEL | Val | Cell Block | Failed QC | | Ben | Benign | IND | Thyroiditis | none | NA | 49 | Fail |
| W169-HuEx-1_0-st-v2-01-1_26A.CEL | Val | Cell Block | Failed QC | | Ben | Sus Follicular | IND | Follicular Adenoma | none | NA | 49 | Fail |
| W170-HuEx-1_0-st-v2-01-1_26B.CEL | Val | Cell Block | Failed QC | | Ben | Sus Follicular | IND | Follicular Adenoma | none | NA | 50 | Fail |
| W171-HuEx-1_0-st-v2-01-1_27.CEL | Val | Cell Block | Failed QC | | Ben | Sus Follicular | IND | Hurthle Cell Adenoma | none | NA | 40 | Fail |
| W172-HuEx-1_0-st-v2-01-1_28.CEL | Val | Cell Block | Failed QC | | Ben | Benign | IND | Hyperplastic Nodule | Hyperplastic Nodule | NA | 24 | Fail |
| W173-HuEx-1_0-st-v2-01-1_29A.CEL | Val | Cell Block | Failed QC | | Ben | Sus Follicular | IND | Goiter | none | NA | 34 | Fail |
| W178-HuEx-1_0-st-v2-01-1_32.CEL | Val | Cell Block | Failed QC | | Ben | Sus Mal | IND | Follicular Adenoma | none | NA | 39 | Fail |
| W183-HuEx-1_0-st-v2-01-1_37.CEL | Val | Cell Block | Failed QC | | Ben | Benign | Benign | Goiter | none | NA | 36 | Fail |
| W188-HuEx-1_0-st-v2-01-1_42.CEL | Val | Cell Block | Failed QC | | Ben | Sus Follicular | IND | Goiter | none | NA | 45 | Fail |

TABLE 6

| Chromosome | Start | End | Category | Strand | Gene | Ensembl Gene ID |
|---|---|---|---|---|---|---|
| chr1 | 150967055 | 150967170 | CODING | 1 | ANXA9 | ENSG00000143412 |
| chr1 | 165513777 | 165514077 | CODING | 1 | LRRC52 | ENSG00000162763 |
| chr1 | 207237121 | 207237151 | CODING | 1 | PFKFB2 | ENSG00000123836 |
| chr1 | 207238398 | 207238498 | CODING | 1 | PFKFB2 | ENSG00000123836 |
| chr1 | 207240857 | 207240983 | CODING | 1 | PFKFB2 | ENSG00000123836 |
| chr1 | 207241542 | 207241627 | CODING | 1 | PFKFB2 | ENSG00000123836 |
| chr1 | 207242792 | 207242872 | CODING | 1 | PFKFB2 | ENSG00000123836 |
| chr1 | 207244869 | 207244918 | CODING | 1 | PFKFB2 | ENSG00000123836 |
| chr2 | 69734650 | 69734707 | CODING | −1 | AAK1 | ENSG00000115977 |
| chr2 | 121999944 | 122000045 | CODING | −1 | TFCP2L1 | ENSG00000115112 |
| chr4 | 86921632 | 86921858 | CODING | 1 | ARHGAP24 | ENSG00000138639 |
| chr4 | 114038540 | 114038571 | CODING | 1 | ANK2 | ENSG00000145362 |
| chr4 | 186548013 | 186548080 | CODING | −1 | SORBS2 | ENSG00000154556 |
| chr5 | 75886275 | 75886356 | CODING | 1 | IQGAP2 | ENSG00000145703 |
| chr5 | 43446493 | 43446659 | CODING | −1 | C5orf28 | ENSG00000151881 |
| chr5 | 160757891 | 160758028 | CODING | −1 | GABRB2 | ENSG00000145864 |
| chr5 | 160761760 | 160761906 | CODING | −1 | GABRB2 | ENSG00000145864 |
| chr8 | 133881975 | 133882045 | CODING | 1 | TG | ENSG00000042832 |
| chr8 | 133883637 | 133883728 | CODING | 1 | TG | ENSG00000042832 |
| chr8 | 133898807 | 133899109 | CODING | 1 | TG | ENSG00000042832 |
| chr8 | 133910415 | 133910491 | CODING | 1 | TG | ENSG00000042832 |
| chr8 | 133980051 | 133980205 | CODING | 1 | TG | ENSG00000042832 |
| chr8 | 134042115 | 134042261 | CODING | 1 | TG | ENSG00000042832 |
| chr8 | 134144099 | 134144190 | CODING | 1 | TG | ENSG00000042832 |
| chr8 | 21976699 | 21976793 | CODING | −1 | HR | ENSG00000168453 |
| chr8 | 134063061 | 134063159 | CODING | −1 | SLA | ENSG00000155926 |
| chr9 | 20360781 | 20360836 | CODING | −1 | MLLT3 | ENSG00000171843 |
| chr9 | 75538960 | 75539039 | CODING | −1 | ALDH1A1 | ENSG00000165092 |
| chr9 | 130674909 | 130674959 | CODING | −1 | ST6GALNAC4 | ENSG00000136840 |
| chr10 | 71161274 | 71161606 | CODING | 1 | HK1 | ENSG00000156515 |
| chr11 | 294110 | 294142 | CODING | 1 | ATHL1 | ENSG00000142102 |
| chr11 | 17336961 | 17336989 | CODING | 1 | NUCB2 | ENSG00000070081 |
| chr11 | 118916305 | 118916355 | CODING | −1 | HYOU1 | ENSG00000149428 |
| chr11 | 118916496 | 118916524 | CODING | −1 | HYOU1 | ENSG00000149428 |
| chr11 | 118918680 | 118918747 | CODING | −1 | HYOU1 | ENSG00000149428 |
| chr12 | 56489495 | 56489578 | CODING | 1 | ERBB3 | ENSG00000065361 |
| chr12 | 44917119 | 44917145 | CODING | −1 | NELL2 | ENSG00000184613 |
| chr12 | 101598298 | 101598340 | CODING | −1 | SLC5A8 | ENSG00000256870 |
| chr14 | 68040521 | 68040604 | CODING | 1 | PLEKHH1 | ENSG00000054690 |
| chr14 | 68053813 | 68053952 | CODING | 1 | PLEKHH1 | ENSG00000054690 |
| chr14 | 31602744 | 31602879 | CODING | −1 | HECTD1 | ENSG00000092148 |
| chr14 | 67817342 | 67817407 | CODING | −1 | ATP6V1D | ENSG00000100554 |

TABLE 6-continued

| Chromosome | Start | End | Category | Strand | Gene | Ensembl Gene ID |
|---|---|---|---|---|---|---|
| chr15 | 57815693 | 57815809 | CODING | 1 | CGNL1 | ENSG00000128849 |
| chr15 | 30700141 | 30700178 | CODING | −1 | AC019322.1 | ENSG00000186399 |
| chr15 | 53907866 | 53908047 | CODING | −1 | WDR72 | ENSG00000166415 |
| chr16 | 55608559 | 55608617 | CODING | 1 | LPCAT2 | ENSG00000087253 |
| chr17 | 36638325 | 36638354 | CODING | 1 | ARHGAP23 | ENSG0000225485 |
| chr17 | 52991132 | 52991191 | CODING | 1 | TOM1L1 | ENSG00000141198 |
| chr17 | 59115294 | 59115405 | CODING | 1 | BCAS3 | ENSG00000141376 |
| chr17 | 62291295 | 62291410 | CODING | −1 | TEX2 | ENSG00000136478 |
| chr18 | 22642676 | 22642705 | CODING | −1 | ZNF521 | ENSG00000198795 |
| chr19 | 13054376 | 13054442 | CODING | 1 | CALR | ENSG00000179218 |
| chrX | 47444696 | 47444722 | CODING | 1 | TIMP1 | ENSG00000102265 |
| chr1 | 207250152 | 207250474 | NON_CODING (CDS_ANTISENSE) | −1 | PFKFB2 | ENSG00000123836 |
| chr2 | 68461674 | 68461760 | NON_CODING (CDS_ANTISENSE) | 1 | PPP3R1 | ENSG00000221823 |
| chr2 | 135326995 | 135327233 | NON_CODING (CDS_ANTISENSE) | 1 | TMEM163 | ENSG00000152128 |
| chr3 | 97686119 | 97686433 | NON_CODING (CDS_ANTISENSE) | 1 | MINA | ENSG00000170854 |
| chr3 | 185270053 | 185270136 | NON_CODING (CDS_ANTISENSE) | 1 | LIPH | ENSG00000163898 |
| chr4 | 186603442 | 186603697 | NON_CODING (CDS_ANTISENSE) | 1 | SORBS2 | ENSG00000154556 |
| chr5 | 75858246 | 75858340 | NON_CODING (CDS_ANTISENSE) | −1 | IQGAP2 | ENSG00000145703 |
| chr5 | 75885496 | 75885553 | NON_CODING (CDS_ANTISENSE) | −1 | IQGAP2 | ENSG00000145703 |
| chr7 | 3827932 | 3828014 | NON_CODING (CDS_ANTISENSE) | −1 | SDK1 | ENSG00000146555 |
| chr8 | 134144098 | 134144157 | NON_CODING (CDS_ANTISENSE) | −1 | TG | ENSG00000042832 |
| chr14 | 103986078 | 103986271 | NON_CODING (CDS_ANTISENSE) | 1 | CKB | ENSG00000166165 |
| chr14 | 74525360 | 74526753 | NON_CODING (CDS_ANTISENSE) | −1 | C14orf45 | ENSG00000119636 |
| chr19 | 14651611 | 14651646 | NON_CODING (CDS_ANTISENSE) | −1 | TECR | ENSG00000099797 |
| chr1 | 63539464 | 63539495 | NON_CODING (INTERGENIC) | −1 | | |
| chr2 | 178491544 | 178491735 | NON_CODING (INTERGENIC) | −1 | | |
| chr2 | 190242379 | 190242413 | NON_CODING (INTERGENIC) | −1 | | |
| chr4 | 141781067 | 141781681 | NON_CODING (INTERGENIC) | −1 | | |
| chr5 | 64777768 | 64777810 | NON_CODING (INTERGENIC) | −1 | | |
| chr5 | 154317939 | 154317965 | NON_CODING (INTERGENIC) | −1 | | |
| chr6 | 116569802 | 116570125 | NON_CODING (INTERGENIC) | 1 | | |
| chr8 | 40384303 | 40384365 | NON_CODING (INTERGENIC) | 1 | | |
| chr9 | 110015200 | 110015261 | NON_CODING (INTERGENIC) | 1 | | |
| chr9 | 98951079 | 98951119 | NON_CODING (INTERGENIC) | −1 | | |
| chr12 | 56497250 | 56497274 | NON_CODING (INTERGENIC) | 1 | | |
| chr14 | 74098210 | 74098469 | NON_CODING (INTERGENIC) | 1 | | |
| chr14 | 67997492 | 67997690 | NON_CODING (INTERGENIC) | −1 | | |
| chr15 | 69863785 | 69863882 | NON_CODING (INTERGENIC) | 1 | | |
| chr16 | 9799693 | 9799739 | NON_CODING (INTERGENIC) | −1 | | |
| chr17 | 46060460 | 46060489 | NON_CODING (INTERGENIC) | 1 | | |
| chr18 | 10323538 | 10323687 | NON_CODING (INTERGENIC) | −1 | | |
| chr19 | 31292048 | 31292108 | NON_CODING (INTERGENIC) | −1 | | |
| chrX | 121608346 | 121608389 | NON_CODING (INTERGENIC) | 1 | | |
| chr1 | 76728480 | 76728504 | NON_CODING (INTRONIC) | 1 | ST6GALNAC3 | ENSG00000184005 |

TABLE 6-continued

| Chromosome | Start | End | Category | Strand | Gene | Ensembl Gene ID |
|---|---|---|---|---|---|---|
| chr2 | 25517222 | 25517315 | NON_CODING (INTRONIC) | −1 | DNMT3A | ENSG00000119772 |
| chr2 | 142875777 | 142875812 | NON_CODING (INTRONIC) | −1 | LRP1B | ENSG00000168702 |
| chr2 | 216295326 | 216295393 | NON_CODING (INTRONIC) | −1 | FN1 | ENSG00000115414 |
| chr3 | 49757336 | 49757463 | NON_CODING (INTRONIC) | 1 | RNF123 | ENSG00000164068 |
| chr4 | 964874 | 964904 | NON_CODING (INTRONIC) | −1 | DGKQ | ENSG00000145214 |
| chr6 | 159146270 | 159146424 | NON_CODING (INTRONIC) | 1 | SYTL3 | ENSG00000164674 |
| chr6 | 90656323 | 90656369 | NON_CODING (INTRONIC) | −1 | BACH2 | ENSG00000112182 |
| chr8 | 12811197 | 12811530 | NON_CODING (INTRONIC) | 1 | AC135352.2 AC135352.1 | ENSG00000250305 ENSG00000170941 |
| chr8 | 102663912 | 102663950 | NON_CODING (INTRONIC) | 1 | GRHL2 | ENSG00000083307 |
| chr8 | 134061160 | 134061479 | NON_CODING (INTRONIC) | −1 | SLA | ENSG00000155926 |
| chr8 | 134096052 | 134096099 | NON_CODING (INTRONIC) | −1 | SLA | ENSG00000155926 |
| chr10 | 11184698 | 11184764 | NON_CODING (INTRONIC) | 1 | CELF2 | ENSG00000048740 |
| chr10 | 17706435 | 17706637 | NON_CODING (INTRONIC) | 1 | STAM | ENSG00000136738 |
| chr11 | 34356412 | 34356736 | NON_CODING (INTRONIC) | −1 | ABTB2RP1-145M24.1 | ENSG00000166016 ENSG00000254708 |
| chr12 | 8909824 | 8909852 | NON_CODING (INTRONIC) | 1 | RIMKLB | ENSG00000166532 |
| chr12 | 52446608 | 52446664 | NON_CODING (INTRONIC) | 1 | NR4A1 | ENSG00000123358 |
| chr12 | 4752021 | 4752047 | NON_CODING (INTRONIC) | −1 | AKAP3 | ENSG00000111254 |
| chr18 | 12258190 | 12258251 | NON_CODING (INTRONIC) | 1 | CIDEA | ENSG00000176194 |
| chr20 | 44846848 | 44846915 | NON_CODING (INTRONIC) | −1 | CDH22 | ENSG00000149654 |
| chrX | 50513401 | 50513469 | NON_CODING (INTRONIC) | −1 | SHROOM4 | ENSG00000158352 |
| chr2 | 105368792 | 105368851 | NON_CODING (INTRONIC_ANTISENSE) | 1 | AC068057.2 | ENSG00000234177 |
| chr2 | 192782864 | 192782954 | NON_CODING (INTRONIC_ANTISENSE) | −1 | AC098617.2 | ENSG00000233766 |
| chr3 | 46519685 | 46519752 | NON_CODING (INTRONIC_ANTISENSE) | 1 | LTF | ENSG00000012223 |
| chr5 | 170178577 | 170178642 | NON_CODING (INTRONIC_ANTISENSE) | 1 | CTC-455F18.1 | ENSG00000253348 |
| chr7 | 50821823 | 50821852 | NON_CODING (INTRONIC_ANTISENSE) | 1 | GRB10 | ENSG00000106070 |
| chr8 | 19455543 | 19455613 | NON_CODING (INTRONIC_ANTISENSE) | 1 | CSGALNACT1 | ENSG00000147408 |
| chr4 | 3937246 | 3937271 | NON_CODING (ncTRANSCRIPT) | 1 | AC226119.1 | ENSG00000251271 |
| chr4 | 186596260 | 186596514 | NON_CODING (ncTRANSCRIPT) | 1 | RP11-626E13.1 | ENSG00000235902 |
| chr4 | 186695668 | 186696175 | NON_CODING (ncTRANSCRIPT) | −1 | SORBS2 | ENSG00000154556 |
| chr5 | 112227300 | 112227325 | NON_CODING (ncTRANSCRIPT) | 1 | SRP19 | ENSG00000153037 |
| chr12 | 121134928 | 121135044 | NON_CODING (ncTRANSCRIPT) | −1 | RP11-173P15.3 | ENSG00000256364 |
| chr17 | 70067185 | 70067316 | NON_CODING (ncTRANSCRIPT) | −1 | AC005152.2 | ENSG00000234899 |
| chr1 | 41237103 | 41237256 | NON_CODING (NON_UNIQUE) | 1 | | |
| chr11 | 62392841 | 62392931 | NON_CODING (NON_UNIQUE) | −1 | | |
| chr15 | 30856564 | 30856589 | NON_CODING (NON_UNIQUE) | 1 | | |
| chr15 | 32880513 | 32880756 | NON_CODING (NON_UNIQUE) | −1 | | |
| chr1 | 207245729 | 207245863 | NON_CODING (UTR) | 1 | PFKFB2 | ENSG00000123836 |
| chr1 | 207249337 | 207250181 | NON_CODING (UTR) | 1 | PFKFB2 | ENSG00000123836 |
| chr1 | 220955244 | 220955269 | NON_CODING (UTR) | 1 | MOSC2 | ENSG00000117791 |

TABLE 6-continued

| Chromosome | Start | End | Category | Strand | Gene | Ensembl Gene ID |
|---|---|---|---|---|---|---|
| chr2 | 1546441 | 1546465 | NON_CODING (UTR) | 1 | TPO | ENSG00000115705 |
| chr2 | 219501335 | 219501605 | NON_CODING (UTR) | 1 | PLCD4 | ENSG00000115556 |
| chr4 | 186508583 | 186508614 | NON_CODING (UTR) | −1 | SORBS2 | ENSG00000154556 |
| chr4 | 186508623 | 186508708 | NON_CODING (UTR) | −1 | SORBS2 | ENSG00000154556 |
| chr4 | 186508719 | 186508748 | NON_CODING (UTR) | −1 | SORBS2 | ENSG00000154556 |
| chr5 | 72861452 | 72861487 | NON_CODING (UTR) | 1 | UTP15 | ENSG00000164338 |
| chr5 | 76003269 | 76003782 | NON_CODING (UTR) | 1 | IQGAP2 | ENSG00000145703 |
| chr5 | 136954991 | 136955154 | NON_CODING (UTR) | −1 | KLHL3 | ENSG00000146021 |
| chr11 | 8502091 | 8502161 | NON_CODING (UTR) | −1 | STK33 | ENSG00000130413 |
| chr11 | 62518475 | 62518581 | NON_CODING (UTR) | −1 | ZBTB3 | ENSG00000185670 |
| chr11 | 65816523 | 65816648 | NON_CODING (UTR) | −1 | GAL3ST3 | ENSG00000175229 |
| chr12 | 51325694 | 51326114 | NON_CODING (UTR) | 1 | METTL7A | ENSG00000185432 |
| chr14 | 75483207 | 75483414 | NON_CODING (UTR) | −1 | MLH3 | ENSG00000119684 |
| chr15 | 57842742 | 57842912 | NON_CODING (UTR) | 1 | CGNL1 | ENSG00000128849 |
| chr16 | 56693090 | 56693114 | NON_CODING (UTR) | 1 | MT1F | ENSG00000198417 |
| chr17 | 16284451 | 16284484 | NON_CODING (UTR) | 1 | UBB | ENSG00000170315 |
| chr17 | 56566950 | 56567688 | NON_CODING (UTR) | −1 | MTMR4 | ENSG00000108389 |
| chr17 | 76105004 | 76105032 | NON_CODING (UTR) | −1 | AC021593.1 | ENSG00000204282 |
| chr18 | 54265010 | 54265231 | NON_CODING (UTR) | −1 | TXNL1 | ENSG00091164 |
| chr1 | 1477083 | 1477357 | NON_CODING (UTR_ANTISENSE) | 1 | SSU72 | ENSG00000160075 |
| chr2 | 223186154 | 223186395 | NON_CODING (UTR_ANTISENSE) | −1 | AC010980.2 | ENSG00000237732 |
| chr6 | 166778506 | 166778894 | NON_CODING (UTR_ANTISENSE) | 1 | BRP44L | ENSG00000060762 |
| chr12 | 51325636 | 51326143 | NON_CODING (UTR_ANTISENSE) | −1 | METTL7A | ENSG00000185432 |
| chr14 | 68055259 | 68055326 | NON_CODING (UTR_ANTISENSE) | −1 | PLEKHH1 | ENSG00000054690 |
| chr14 | 68055450 | 68055755 | NON_CODING (UTR_ANTISENSE) | −1 | PLEKHH1 | ENSG00000054690 |
| chr16 | 3072266 | 3072544 | NON_CODING (UTR_ANTISENSE) | −1 | TNFRSF12A | ENSG00000006327 |
| chr16 | 58079588 | 58079614 | NON_CODING (UTR_ANTISENSE) | −1 | MMP15 | ENSG00000102996 |
| chr19 | 17462708 | 17462776 | NON_CODING (UTR_ANTISENSE) | 1 | PLVAP | ENSG00000130300 |

TABLE 7

| SEQ ID NO: | SEQUENCE |
|---|---|
| 1 | AACTGAGCCCAATTACCAAGTCCTGATTCGCATCCTTATCTCTCGATGTGAGACTGACCTTCTGAGTATCAGAGCTGAGTTCAGGAAGAAATTTGGGAAGTCCCTCTACTCTTCTC |
| 2 | TTGGACTGTCAGAACAACCGGATTCGAGAGGTGATGGATTATACCTTCATCGGGGTCTTCAAACTCATCTACCTTGACCTCAGCTCCAACAACCTAACCTCGATCTCCCCATTCACTTTCTCGGTGCTCAGCAACCTGGTGCAGCTGAACATTGCCAACAACCCTCACCTGTTATCGCTTCACAAGTTCACCTTTGCCAACACCACCTCTTTGAGGTACCTGGACCTCAGAAATACCGGCTTGCAGACCCTGGACAGTGCTGCCTTATACCACCTCACTACTCTGGAGACCCTGTTTCTGA |
| 3 | TTCTTTGTGGAATCCGTCTGTGATGATCCTG |

TABLE 7-continued

| SEQ ID NO: | SEQUENCE |
|---|---|
| 4 | CCCTGACTATCCTGAAAGGAACAGAGAGAACGTGATGGAGGACTTCCTGAAGA GAATTGAATGCTACAAAGTTACCTACCGACCTCTTGACCCAGACAACT |
| 5 | ATCAAGGTGATAAACGTGGGCCAGCGATTTTTAGTCAACAGAGTCCAGGACTAC ATCCAGAGCAAGATAGTCTACTACCTCATGAATATCCACGTCCAGCCTCGCACC ATTTACCTTTGCCGGCATG |
| 6 | AGGAAATAACAGACCTCAAAGTGTGGACAAGCCAGTTGAAGAGGACCATACAG ACTGCTGAATCTCTCGGGGTGCCCTATGAGCAG |
| 7 | TGCAGAGATTGAGAAACGGTACCCAGAAGAGTTTGCACTTCGAGATCAAGAGA AGTATCTGTATCGATATCCTGGTGGGGA |
| 8 | CAATTAAACTTAACGTGGAGGCTGTGAACACGCACCGTGACAAGCCAACT |
| 9 | TGCAACCACCACTCCATCAGGCTCTCCTCGGACCTCTCAACAAAACGTTTATAA TCCT |
| 10 | CCGAAGGGAGCCGATCGGAAACAGAAGACTGACCGGGAGAAGATGGAGAAAA GAACTGCCCAAGAGAAGGAGAAATACCAGCCGTCCTATGAAACCACCATC |
| 11 | CTTAGAACAGCGAAACTTGACTTTGGAAACAGAAATGATGAGCCTCCATGATG AACTGGATCAGGAGAGGAAAAAGTTCACAATGATAGAAATAAAAATGCGAAAT GCCGAGCGAGCAAAAGAAGATGCCGAGAAAAGAAATGACATGCTACAGAAAG AAATGGAGCAGTTTTTTTCCACGTTTGGAGAACTGACAGTGGAACCCAGGAGAA CCGAGAGAGGAAACA |
| 12 | AAATCCCCAGAGAACGTATGGAACGAAAAAGA |
| 13 | GACTAGCCCAGGCCGAGTGGACCTCCCAGGATCAAGCACCACTCTTACAAAGTC TTTCACTAGCTCTT |
| 14 | GAATAGCAGAGCAAACCGTTGTAACACTAAGAAACCCAAATGCGGTTTTAACTT TAGTGGATGACAACCTTGCACCAGAATA |
| 15 | GCTGCTTTGACTCTCCCGCGAAGACCTTTCCTTCACTGTTCTACTGTGATTCCCG TTGTGGTTCTGACCCTGAAATTTACTATGCACCTTTTCAAGCTCAAAGACTCATG GTGCTTTCTTCCCTGGATGTTATTTATATCCTGGACTTCACATCATATCCGAGAT GG |
| 16 | TGTCTTCGTTTTCATGGCCCTTCTGGAATATGCCCTAGTCAACTACATCTTCTTTG GGAGGGGGCCCCAACGCCAAAAGAAAGCAGCTGAGAAGGCTGCCAGTGCCAA CAATGAGAAGATGCGCCTGGATGTCAACAA |
| 17 | TATCCCAGGTTATCCCTCAGCTTTAAGCTTAAGAGAAACATTGGCTACTTTATCC TGCAAACATACATGCCTTCCATCCTGATTACCATCCTCTCCTGGGTCTCCTTCTG GATTAATTACGATGCTTCAGCTGCAAGGGTGGCATTA |
| 18 | ACTGTCCAGTGCCAGAACGACGGCCGCTCCTGCTGGTGTGTGGGTGCCAACGGC AGTGAAGTGCTGGGCAG |
| 19 | GGCTACATTAACAGCACAGACACCTCCTACCTCCCTCAGTGTCAGGATTCAGGG GACTACGCGCCTGTTCAGTGTGATGTGCAGCAGGTCCA |
| 20 | CCTCTCCAAGAGTAGCCAGATTTGCCACATCCTGCCCACCCACGATCAAGGAGC TCTTTGTGGACTCTGGGCTTCTCCGCCCAATGGTGGAGGGACAGAGCCAACAGT TTTCTGTCTCAGAAAATCTTCTCAAAGAAGCCATCCGAGCAATTTTTCCCTCCCG AGGGCTGGCTCGTCTTGCCCTTCAGTTTACCACCAACCCAAAGAGACTCCAGCA AAACCTTTTTGGAGGGAAATTTTTGGTGAATGTTGGCCAGTTTAACTTGTCTGGA GCCCTTGGCACAAGAGGCACATTTAACTTCA |
| 21 | GCACTGCTGGTGTGTAGATGAGAAAGGAGGGTTCATCCCTGGCTCACTGACTGC CCGCTCTCTGCAGATTCCACAGT |
| 22 | AGCACTCTTTCTGTCAGCTCGCAGAGATAACAGAGAGTGCATCCTTGTACTTCA CCTGCACCCTCTACCCAGAGGCACAGGTGTGTGATGACATCATGGAGTCCAATG CCCAGGGCTGCAGACTGATCCTGCCTCAGATGCCAAAGGCCCTGTTC |
| 23 | TCTGACCTGGGTGCAGACCCACATCCGAGGATTTGGCGGGGACCCTCGGCGCGT GTCCCTGGCAGCAGACCGTGGCGGGGCTGATGTGGCCAGCATCCACCTTCTCAC GGCCAGGGCCACCAACTCCCAACTTTTCCGGAGAGCTGT |
| 24 | TTCTACCCAGCCTACGAGGGGCAGTTTTCTCTGGAGGAGAAGAGCCTGTCGCTG AAAATCATGCAGTACTTTTCCCACTTCATCAGATACGG |

TABLE 7-continued

| SEQ ID NO: | SEQUENCE |
|---|---|
| 25 | TGAGCCCGCACCGGGGACACCTGGGGACCAAGAACCTCTGTGTGGAGGTGGCCGACCTGGTCAGCATCCTGGTGCATGCCGACACACCACTGCCT |
| 26 | ACTGGATAGCGACTTCCTTGCCGTGCTAAGTGACTACCCGTCTCCTGACATCAGCCCCCCGATATTCCGCCGAGGGGAGAAACTGCGTGTGATTTCTGA |
| 27 | TAGCTTAAGTGATGGCAGCGATAGTGAAAGCAGTTCTGCTTCTTCACCCCTACATC |
| 28 | CCTCCTGGAGTAGTGAATATTGTTCCTGGTTATGGGCCTACAGCAGGGGCAGCCATTTCTTCTCACATGGATATAGACAA |
| 29 | CCGCTGGTCCGCGAGCCCTGCCGCAGCTGTGCCGTGGTGTCCAGCTCCGGC |
| 30 | CCCTCCCTGTGTGAAATGTATTATCACCAGCAGACACTGCCGGGCCTCCCTCCCGGGGGCACTGCCTGAAGGCGAGTGTGGGCATAGCATTAGCTGCTTCCTCCCCTCCTGGCACCCACTGTGGCCTGGCATCGCATCGTGGTGTGCAATGCCACAAAATCGTGTGTCCGTGGAACCAGTCCTAGCCGCGTGTGACAGTCTTGCATTCTGTTTGTCTCGTGGGGGAGGTGGACAGTCCTGCGGAAATGTGTCTTGTCTCCATTTGGATAAAAGGAACCAACCAACAAACAATGCCATCACTGGAATTTCCCACCGCTTTGTGAGCCGTGTC |
| 31 | GAATGCAGACGGGTCAGGCGCTGTGAACTTCCT |
| 32 | CTCTGGAGGAGTTTTTGAAAGCCACAGAA |
| 33 | AAAGAACAATCGACAGGACAGAAGCGGCCTTTGAAGAACGACGAACTATAA |
| 34 | TGAGCCTTTGGAGTTAGGAGGTCCTGGAG |
| 35 | CTGTTTTTTCGGGTAGAGGAGCGCAAGAAGTGGCCCGAACGGCTGTCTGCCCTCGATAATCTCCTCAA |
| 36 | GTGATTTTCATGATGCTGGGCGGCACTTTTCTCTACTGGCGTGGGCGCCGGATTCAGAATAAAAGGGCTATGAGGCGATACTTG |
| 37 | GATGGAAAAGTTAAGCACAATGGTCAG |
| 38 | TTAGAACTTCGATTTAACAAATGTGTTCGTCTCTGTGGAACAG |
| 39 | GATGTCATCCGGAAACCTCAAGGCCAAGTGGATCTGAACTCCCGCTGCCAAATTGTTCGAGGGGAGGGTTCACAGACGTTTCAG |
| 40 | TGGCCAGCTATATGAACCATTGCACTACAACTGTGAACCCCCCCACCAACCCACCCGGAGCCTGCCAGCTGTGGGAACTGGATGGACGACAGTTCTTTTCTTCTGTTTCCTGTGCTACCAAGGGGCCAACGTTGCTGTGA |
| 41 | CAACTGCAACTTGGCCTCTTGATCCACCAAAGGATGAGAAACAAGGGTGGAGACATGTGAGAATTAAACAGATGGGAAAAATGCCAGTGGACAAACACACTACCTCTCATTATCTGGATTCGAACTTTATGGCAC |
| 42 | ACTAAAATGTTGATGGGCGAAGTGATGAGAGAAGCTGCCTTTTCACTAGCTGAAGCCAAGTTCACA |
| 43 | CTGAGTCAGACTACCCAGGAGCAGAAGCAGTTGTCTGAGAAGCTCAAAGAGGAGAGTGAGCAGAAGGAGCAGCTAAGAAGGTTGAAGAACGAGATGGAGAATGAGCGGTGGCACCTG |
| 44 | AGAGAAGCAGGATATGCGTTGGGTAGAGCAGCTGGAGT |
| 45 | GTAGATGCCAGTCTCACAATAGACACAGCAAAATTGTTTCTGTCTTGCCTTTTGCCATGGGGAGTGGATAAAGATTTAGATTATCTTTGCATTAAGCACCTCAATATTTTAAAGCTTCAGGGTCCTATTTCTTTGGGAATTTCTTTGAATGAAGATAATTTCTCACTGATGTTGCCAGGTTG |
| 46 | TTGACTTCCGAGAGTATGTGATTGGCCTGGCTGTCTTGTGCAACCCTTCCAACACAGAG |
| 47 | GCCGCTCCGAGGGCGTTTGGGGTCAGGCTG |
| 48 | AGGTGTGGATGTAAGCGAAGTCAAAGAAGTATACCTCGACCTGGTTAAGAAAGGCGTTCA |
| 49 | TGCTATGGCACCTTAGTGGAACACATGATGGAGCCGCGACCCCTCAGCACTGCACCCAAGATTAGTGACGACACACCACTGGAAATGATGACATCGCCTCGAGCCAGCTGGA |

TABLE 7-continued

| SEQ ID NO: | SEQUENCE |
|---|---|
| 50 | TGAGGAGGGGCTGGATGACCAAAGCATTGTAACAGGGCTGGAAGCCAAGGAAG<br>ACCTCTATCTTGAACCCCAAGTTGGCCATGACCCCGCCGGCCCTGCTGCCTCGC<br>CTGTCCTGG |
| 51 | AATCATACAATGACCCAACACAGCAGTTAG |
| 52 | ACTTCCTCATCACCAACGATGAGGCATACGCTGAGGAGTTTGGCAACGAGACGT<br>GGGGCGTAACAAA |
| 53 | GTCCCACAACCGCAGCGAGGAGTTTCT |
| 54 | GTAAAGGTAACAACTCCAGGCTCTGAACAGGCATTCCCTTAGCTGAGTTCACAA<br>AATACCATAAAAGTGATGCATAACCTTTATCTTGTACAAAATAATGAGAATTTG<br>GCCACTACTATATAAGAAATATCTATTTAAAATCATAGTGTACAGAACTCCCCT<br>ATAAAGAAAACACGTGGAGTGCTTAATTCCTTCCTTTGTTAGACACATTTAATA<br>GACAGAGAATTACCATAATGTACATACACTTCAATGGATACAATCAGAAAGCA<br>GGCAGACTGTCAGCTTACAGACCCTAGACCGTTAGTCAGGCAACACCCAAATTT |
| 55 | AAGTGGCTTGTTACTGCCAACTCACACTGGCATAGCAATTTTAAATGTCTTCCAT<br>ATATCTAAAACAGCAGTCACAATCGCAGAAAC |
| 56 | GCGAGAGTTATGTCAAAGATTTACCTGCAAAGATTTAGCTAAAAAGAACACTTG<br>GAAAACACATATAAATGAAACACATATGAATGAAGACCCCCTAGCCACATTCA<br>TCCTTGTAGTTAGGACTGGAATTCTAGCCATAGTCACATCCCCAGTCCCTGGCCC<br>AGATCGAACCTCTAATATAATTATTACCCACCAAGAAAATAAGATCGTATTCTG<br>TTTCAGTACTCAGAGACGGTTC |
| 57 | TGACACACCGGCAGACATTCACATCTCTTCCATAGTACATCCCCGGCTGCACA<br>GACTCTTCAGATCTGTTAGCTTGAACAGGGACCCATAGTATGTGGCCAGTGCAG<br>GGTCATCTCTCTGAATGAGAAGGGGCTTCTGCTCCCAGAATTCCTTGAAAAAAG<br>TCTCTGTCTTGATGGGCGAGATTAAACTTTCAAAGAGACTACTGGGACTGTCAA<br>AGTTTAAAGCTGAAGGCCCCCCAGCTGCTTCTAACTTCATCTGCTTACAGGGAG<br>CCGGCCCCTCTTCCTTCCCACTCCCTGTAGGCTTTGCTTTCTTTG |
| 58 | TGTTAAGGAAATGATACAGGCTTCCTATATCTTTTTCCTTAAAAACGACTCTATG<br>GACTTAAGTTCACCGAAGGAAGTGGAATG |
| 59 | ACTGCGGCATTCCTTTAGGCTGACAAGGGGTTTTGGTGAAATAAAATGTTTTCA<br>ATTGTTTCTCAATAGTCATTGTCTTGGTTTTGGCATAGGTTTAAAATATCCGTGT<br>GTGCTCTGATGGATTGTCCAGTGGGAATTTACTTCTTATAAAAGGAAAAGAGAA<br>AGACAGACTGACTCAGGGGACAAATAGGTGGTGACTCAGATTGACTGTCTGAT<br>CAGAGAAGGGAGTGAAAATGGCTTGGGACCTTTTCTGGAG |
| 60 | TCTGATACCATTTTCGGGGCAAAGAACTTGGCTAACTTTGCAAGGTAAACTCCA<br>TTCCGGAGCCCTTCTTCCAATTCAGTGGTTGGTGGCAATTC |
| 61 | ATGCAGCTTCATCCACGGACAGTTCATTGGCCAGAATACCACCTATTTTGCTGA<br>AAGA |
| 62 | GCTAGAAAGCACGAGACTGCATTTCTCAAACTCCTTGTGGAGTTTCACACACTG<br>ACCGCACACCCTGTTATGGGCGATGGAGG |
| 63 | ATTTTCAGCGACAGGCTCTTCTCCTCCAGAGAAAACTGCCCCTCGTAGGCTGGG<br>TAGAAG |
| 64 | GACGGAAGTCTCTACAGCAAGGCTAAGGGCTCGCCAGACGGCGAACATCAGGG<br>GTGCATGGTGGGCACTGCCCAGGCAATAAGTTAGGAAGCAGCAGGGCTGGTGT<br>CGGGTGTGGGCCGGGCTTCATTTCTGGGCAGGCATGAGGTCGTCGATGGCCTGG<br>CCCTGCTCCAGCCGCTGCTCCATCTCGATGAGCA |
| 65 | GCGCTACCTAAATGCCACTGGGAGAGACCTCCTGCAAAGTTTTCTTTAGCCCCT<br>CTTTTATCCCACAATACACAAGATATAATCCATTTTTATATATCCCAAAGTTGTG<br>GCAACAGCTTCTTTCTTTTCTGCTCAATGCCACTTTGTTTCCTAGTAATTCATGAC<br>CACTATTAATTCTATCATTGTCACTGCTCCTGCTTAAGATCACTTCTCAAGGATA<br>CCTCAGTAAGCAATGGATAAATCAACTTTTTGTTATATGTGCCAAGTACTAAGTT<br>TCAGGGTTCTCTTCAGCAATCATTAATTAATACTTCAGCCATTAATTCAGATGCA<br>AATAATTTTCTTTTTTCTTTTTTTGAGATGGAGTTTCACTCTTGTTGCCCAGGCT<br>GGAGTGCAATGGCGTGATCTCAGCTCACCGCAACCTCCGCCTCCCAGGTTCAAG<br>CGATTCTCCTGCCTCAGCCCCCCTAGTAGCTGGGATTACAGGCATGCGCCACCA<br>CACCCAGCTAATTTGTATTTTTAGTAGAGACGGGGTTTCTCCGTGTTGGTCAGG<br>CTGGTCTCGAACTCCTGACCTCAGGTGATCCGCCTGCCTCGGCCTCCCAAAGTG<br>CTGGGATTACAGGCATGAGCCACCACACCCAGCCAGATGCAAATAATTTTCTTA<br>GAAAATTATTTCAAAAGTTATTTTAGGCCCAGAAATCAAGGATTGTTCCAACCA<br>TGAAAATGGGTAAGACACCTGCCTTAAGCAAATCTAACCTGCTATTACTTGCCA<br>AATTTTATATATTCTTTTCTCTTGCCTGTATTTCTAATTAGTGATTTGTTTAATGA |

TABLE 7-continued

| SEQ ID NO: | SEQUENCE |
|---|---|
| | AGAACTCTTCATGTAGAGCAATTAACTGGGCCTAAGAAATTTCGAAGCTTTCCA<br>TGACATAAAGTGGTTAAAAAAAATGCTTTGACAGTCTTCTTCTGCCATTAGTTC<br>AACTGCCTTTACGCTTTTTTTTTTTTTTTTTTTGAGATGGAGTTTCACTCTTGT<br>TGCCCAGGCTAGAGTGCAATGGCGTGATCTTGGCTCACTGCAACCTCTGCCTCC<br>CGGGTTCAAGCAATTCTCCTGCCTCAGCCTCCTGAGTAGCTGGGATTTCAGGCA<br>TACGCCACCATGCCTGGCTAATTTTGTATTTTTAGTAGAGACAGGGTTTCTCCAT<br>GTTGGTCAGGCTGGTCTCGAACTCCCGACCTCAGGTGATCTGCCTGCCTTGGCCT<br>CCCAAAGTGCTGGGATTACAGGTGTGAGCCACCACCCCCAGCCGCCTCTATGCT<br>TTTTGTTTCTTTGATATATCTAAACTTAAGGTCAGAACAGAAATTCATGTGCTGA<br>ACAGAATGGATTCTTTTTGCAGTACCAATCCAATTGAATCCTCTTTTTATTTTCCT<br>GCGTCCTTACCAGTCACTTTGATA |
| 66 | AAAAGCAGCCAGACATAGTGATACACACCTGCAGTC |
| 67 | ATGTGGTAAGAATTGCACACCTCAAATCTACC |
| 68 | GACTAAGAGGGGAATAAAAGCAAGAAGAAAAAGAAACGTAAGAACACCAGTA<br>AAGGAAAGACAGGGACCGAGACAGGTGGTTAAGGGAAATGAAAAAAAAAAAA<br>AAAAGGTGAAAGTCAATCCAAACAAAGAAAAATGGCACTTCCAACCAAAAAAA<br>ATGAAGGTGTAGAACCCTGTCATCAATTGCTCAGA |
| 69 | AAGATTGTCACTTTTGGTGGATCTGCAAAAAAAGT |
| 70 | TCTGCAGGTAGTAGATGATGGTTCCATCTCGGCATTGTCTATCCTCTCCATATTC<br>AGACTGTGTGACTGAGCTTCCTTGATTTATATAGCATCTGACCCAAAATCACAA<br>AAAAGTCACTCCTGATGACATTTGCATGGGGAGTCTTTCATTTGGACTTCAGTTC<br>TTAATTGCCGAAATAAGTACTAGTGAATTATGTAGCGTTTTTACCCAAAACTAA<br>TCTTCTGTACAAAGTTGTGTGCATATTGAGATGATTAGTTAAGGCAGTGTAGTTT<br>TTTAAATTTTTTCTGTATAAATTTCCTTCCTTCTTCCCCACCTCAGGCACCTACCC<br>TACTCCTTTCAGAGCACTTTATATCCCTCTTGAAATACAAAGAAATTGAAAAAA<br>AAAAAAAGTAACTGTCTTTAAAGGAATTTGTCTTCTATTAGGAGACACAGACT<br>TTTATTTTGCTTTATTCTATTCTCTTTGTACTTGGAGAGCGTAATCAACTTGTCTC<br>ATAATGGGCTAGTGATGAAACAAGGGTGATAGTTGGAAACAGTCATTACAACA<br>TGGTTATTTTTGTTATATAGAAGACTATCATGTAAATAAGTGCAATCGTGTTCTT<br>ACGTACTGGCTAAA |
| 71 | CACGTGACGACCCAGGACACATGCGCACCCGACGCAGCCCAGG |
| 72 | GCTCAGGCAGCACCTGACCCTAGCCAG |
| 73 | CCAGGGTAATTATGCAGTGTCACCACTACTCACAGGGATTATGGCCTGAGAAAC<br>TAAAATGATACTTCTTAGGTGACCAGAGGATGGAGAACTTCTTAACTGGTTTG<br>GAGGTCCACATAAAGAATAATTGGGGTCTAGAATTAAGGAAGGAAAAGCAATA<br>CAAAGAAATGGAGCAGGGCTATAGCAGTGAACCAATTGGTTGGTAAGTGAAAC<br>CTGTAAGATGCCTAATTGAGTAATTTAATGACTAATTTTATTAGGCTAAACAGA<br>ACAGAAACCATGCTAATCTGTAACAAATAAGTGGCGCCAGCCTATTACAGTGA<br>ATG |
| 74 | ATAGGGGCTGCTGTAGAATGCCTTCCTTGCATAGTGACTGTCCGTGATTCCATTA<br>TTCTCAAA |
| 75 | CTCAAAGAAACTAGTGATGGCAGAGCCCTTTAAGCAAGGACGTAGAATGGATG<br>TTCAAAAAG |
| 76 | GTGTGAGAACAAAAGCTGTGTTGGGGCCAAGCCTCTGTGT |
| 77 | TTTATACGTGTCTGAATAAAAATGC |
| 78 | TCTAGTGGCCGCAAAGGGCATCCCAGAATGTGATGCCACTGGGTGCACAGACA<br>GCCTCCCACATTACCAAGGGCATGCTCCCGGGGCCCTAACCTAAGACCCCAGAA<br>GAACGGGTCGCTGCCACCAAGAAGTATAAATATGTGTGGAAGACTACGAGC<br>CTTATTCGAATGACGGCATGGGGTATGGGACTACCTGAAGCTCCCTGACCACT<br>TATAGCAGAAGAGGGATCTGTGGTATAACTGAGACCACCTGGCCCTG |
| 79 | CTGGTCTGAGCCAATTTAGTCCTTCAATGATTGTATTAGCTGCCATGGGACGTGA<br>GAGGTGAGAGGAGGCCATTCGTCTTCTTTTCTGTAATCTCCTGCAGGTGGGATA<br>TTAAAAATAGTTAAGGCCAAATTCTGCCAAATATACATGTATTGGCAAGCTGGC<br>ACAAAACAGTCACACAGCCTGCTTCAAGAAAATGGG |
| 80 | CTCTCTGTCTATATACACACCTGCATGCATATATACATATATATATGTATGCATC<br>TATATATTTATATCTAATCTCGTATTGCTTATTGGTTCTGTTT |
| 81 | CTTCATGATACAGGATGTTGTATGTATGTGGAACCATCCTCACTCAC |
| 82 | CCCTGCGCTTGCAGATGAGCACCTGACCTG |

TABLE 7-continued

| SEQ ID NO: | SEQUENCE |
|---|---|
| 83 | TCGGTGCTCACCCAGTATGAGGATCATACGAATTGGTGGTTGGAAAAGCATTGA<br>AATGTCACTGACTTTGACTGTCAGATGTGTGGGGTCAGGCAGGCATGTGTTTCT<br>CGGATGCTCATTGTAGCTCTTGCTTATCCATTTTTATTAACT |
| 84 | GTTGGCCTATGTCAGTCTCTGCTGGTGTCTGGATGAAGATGGACAAGGGGCCAC<br>CACTCTC |
| 85 | AAAGATAATGGACAACAGTGCCGTGACTCCCATGTATTGTCTCA |
| 86 | GGAGATTGGAAACATGCACGCACAC |
| 87 | TTCCTGCGAGCCTGCATCAGTACACGCTGCTGCCCACTCTGTCTCCTCATGTTTT<br>GGAAGGCATGAGGAAGACAGGCCGACACACTGCTTGTGA |
| 88 | TCACGACATTGTAAACCCAAGCCCGAGAGTCACTAT |
| 89 | TTCTGGATTCCTAGAGAGAAGGGTAATACTATGTTACTCAGAACACATCCAGTA<br>TATCAGCATGCTTT |
| 90 | CTGGAAGAATGTCTCCAAGCTGCTGTTAGTGTTTATTTGAAGTGACTTTGAAGG<br>ACTGATAATATTATGGGGCAGGCAGACTCTCACTATCTTAAGGTGGTTCGCCTG<br>AGCCTTCTTAAAGTGGTACC |
| 91 | TTGGGTAGGACAGGGGCCAACTCACACAGTG |
| 92 | CCCATGACTGTTCATGACTATCCCAAAGCTGGATGTTGTCTGTCTCTGGGCCCTG<br>TGTGCTCGCATGCGCGTGTGTGGTGTGTGTGCGTGTGTGTGTGTGCGCA<br>CGTGCACGCATTTACCAAATGCAGGTGTGTCCTCCTACTCAGAAG |
| 93 | GCTGTAGGTCGATCACACAGGGCCAAGACATGTTTCTCCAATATCTC |
| 94 | TGGCTGGCTGAGAATACAGGGTAAAGAACTGTCCAGTGTTGTGAGTGGTGCCTT<br>AGAGTTGCTCATAGCAAGAAAATCACTTGGGAGGGTGGAAGTGGCTCTCAGAT<br>GGTCATTGGTTACCTATAACTTATTTAAAGAAGACCTTGAGAAGTTGGGACATA<br>TCTTGTCACTGAGGAAATTGTGCCAAAGAACTGCTGCTTTATTAACGCATTTGAT<br>CAGATTTGAAAAGAGAGCTCTGTATACACTCTTTTTCTAACTCCAAAGAAATTTT<br>GTTTCTAGAAAGATTCAATTACCGTAATGATGTTCTTTGGAAATGTGCCTTTTTG<br>CGTGTATA |
| 95 | GGGAGCTCATTACACCTGCCTCACTTTGGTTAGCTGAAG |
| 96 | GAAAACTAGGCTCAACAGATAAGAAAATAAGCACCCTGCTTTCCCCTGTAGTCG<br>TTCCAGTGAGGCCTCTGCAGCCTCCTGGGTGGCTTTGGAGCCCTGAACACCTGG<br>GCACAAATCTTGGCTTCCTTCCTTCCATGTGAGGGTCCTGTAAAAGTCGCTTCAC<br>CTCCTGGAGTTACATTATCCTCATCTGTCAAGTGTCGGAAGCTGGAAGTTGGCA<br>AAGAAATGCAAAGCACATTGGAAATGGAAAAGAAAGAAGGAGGCATCCATTG<br>ATAAACACTAAGTTACTTCTTCATGTCCAGAGGACTCTACATGCCACATGC |
| 97 | GGTGGCTTCACTAGAACCTGGACGGGGCAGTAGGGCACTGGATGAGAA |
| 98 | CACAGGATCCGAGAAATACACACCTGTAGTTAGGAAAAAGAACTCAGTAGTGG<br>TGCGTGGAATGAAT |
| 99 | GCTCCTCTTAAACATTTGTAGTTTGCCTTTAATATTTTAAATTATTTTATAATTAG<br>TATATATGGACAACTTATAGAAATCTGGTTTATGTTTTGGAGGAAACTGTGATT<br>GGATATGGGTTGCTGATGGTCGCATAAGAATGTTGAACAGTATTGTAGGCTGCC<br>ATTGAGGTATTCTAAATACCTGATGTGCTTTAGAGAAGA |
| 100 | CCGTGTAGTTGTAGGAAGCATCTTCACTAATGCAACACCAGACAGCCATATTAT<br>GAAGAAATTAAGTGGAAATTAGCGGAAATGTCCATTCATTTGCTGTATTATTTG<br>TATGTAATATTTGGGTTGATCTATAAACACTGTCAGACTAAAGTTTTTAAAATAT<br>ACTTATTTCTATTTATTTCAGCATTTATGAATTTACAACATTGGTAAGTGATATG<br>GGATTTTAAAATTGCAAATGTTCATTATTCATATCATTGAATACATGTTGAGCAC<br>ACCCACATTGTATAGGTTGTGGTAATTAGCTTGTAACTAGGGTATTATCTGT |
| 101 | AGTTTGTTTTGAGGTCAGGTGCTGTGGCT |
| 102 | TGTCCTAGTGCAGGCAGATGTGGCCACCCTCACCTCTCGCAGGGTGCTGCATGC<br>CTG |
| 103 | ACTATCTGAAAATGGGCAGGTGGTGCA |
| 104 | ATGGCAATCTTGAGGGCAGGTGAAGGCAGGGAGAACCAGAAATGGTTGCCAGC<br>TCTTATCTT |

TABLE 7-continued

| SEQ ID NO: | SEQUENCE |
|---|---|
| 105 | AAATGCAGGTGCAATGTGTGTGAGCAAGTGTGTTTGAAAGTGTATGTATTTGAGACCAAGTGCAGTGG |
| 106 | TGTCACTGCTGACTGTGTATGTATGCTGCTGCCTTGAAACACAGTATGTTGGACTTATTCATTCACCTT |
| 107 | GTGATCAACAAGTTCACGCCAAGCCCCAACAGCCCAGCGCTAAGGAAGGCCACAGTGTCC |
| 108 | TCCAGGGCAACAAGGGACAAGATGAAAAAGCTTTCAGGGACAGGCAGTGGGCACCTGTGGGACCCCGCTTCCATTACAGCATGACACTCTG |
| 109 | CCCCACTGCCCTGAGACTTTTCCTAATGGCCCCTCTCAGCAGCCTGGGCAGCCTCCTTGAATTTCTGC |
| 110 | GTTCTGTAAGATCACCGTCCTGACCCCCAGGAGCACACTCACCCATGGGTCAGGCTGCTATTAGA |
| 111 | GCTGCCTTCCTGAAGCTCGCACACCTGCCT |
| 112 | GGAGTGAGAATCTGGAGGGTCAAGAGGAAGGGGAAGGCACTGCAGATATGGGACAGCAGAATAAGACATGG |
| 113 | TTCATGAAGCTCAGCGGCACACACTC |
| 114 | GTGCCGATACCCTGGGGATAATATAATCAAACTAACCGTCTCTGCGCAGCCTGGATAAAACCATGCAAAACGAAAGGTATCAGCTTGTTTTCAAACATCACAAAACCATTCTGAAGAAGCAAACCAGGTTGGATGAGTCCAATGACTGATATGTGTTCCTATGACTTCTCCTACACCTGCTTCCTGGCGTGCCCATCCTGGGACACTGGCGAGTCTGCTCACTGACACTGGCACGGGCCTGTCTGTACAGTCACA |
| 115 | ACCTGCAGTACACGCTTGACTATGACTAAGCCATGGATCAGAGGTCTAATTAAGCCTGATTGCCAGAGCAATGAGAGGATGTTTCAGACATCATATTTTTGTTGTTTAGACTGCTTTATTTTTAACTTTCCAGGGGCATTAAAAAAAAAAAAAGAGGAAAAAGATGCAACCATCCACCTGAGTAAAGATAATATATATAAGTAATTGTTCTTTAAGGGCAATGAGCGAGCCGTATTGTATAATGTTCTCCTTTCATCACTGTTTCGTTCATTGCTCGTGTGGAATTAGAGTGGTTGATTTGGGGGAATCTGGGGGTTTTGTTTTTGTTATTGTTGTTTTGTATGTTCCTAGCACATTTTAGGGGACAGTGTTGAGGATTCCTTACTAAGCTGACTGTCTTTTGCTGGGTACATCTGCTGGCAGGTTTCTCTAACGTGACAATGTGATACTTCGGGTCAGTTTCTGTGGCTCCCCTCTCCCCCTCGTTACGCTTGCACTTGACATTTTG |
| 116 | GTTAAGAATGTCTGAGGGGTCAGGCG |
| 117 | AGGCGATCTGAGGACCCGACATAACCGAAACGTCTTGGATGCTGGACAGTCTATAACTGGCACATGCCAGGGAGACAAGCAATGACAAAGCTCAAACACTAAAGGTGGGACCATCAC |
| 118 | CAAGTTTTCGATGTGTCTCTTTTTCCCGTAAAGTGGCTGAAATCTGAAGCTGAATCTGCAAGTGTCATGGAGTCATTGAATCTCACAGTCTCAACTGATAAAAGTTATTAAAGGTCGTCTGGTTCAGCCTTC |
| 119 | GAGAGTGGGTGGATTCATTGCCACACTCTTTTCTCCCAGGGACCCAGGAAACTAGGACTTTGTGTGTTTGCTGCCCACCTCCCTTTTATTTTTTAAATGCATTAAAAACTGTGCTAGTCTCCTTTGCATGGACTTCAAGCTGCATGAAATGCAA |
| 120 | TGCCTCTTGTATGTTGATGCCACTTCTTGGAAGAAGATGAGGGCAATGAGTTAGGGCTCCTTTTCCCCTTCCCTCCCACCAGATTGCTCTC |
| 121 | CAAAATATTCGGTCCTTGTGACTTCCA |
| 122 | TCCTCAACCTAGAAATACGTAATCAAGCAAACTATCAATCAAGTGTGAGGGTAGAATATGAGAGACGTGAATACTGATGGGGATGTGATATGCAGCAGGCACTGTTCTAAATGGTTTACATGTACCAACCCAATTAAGAAACTTAAAATACACACGTGCACACACACACACACACACACACACACACACACACACAGTTTTTCCTGCTAATCATTTTACGATGAAACAGCCAAGTAGC |
| 123 | GTCAGCATTCCGGTGGTGTAACTGTGTGTTTCCCTCCAGCCCTGGCCTCCTGCCCTTGTCACTAATCACCAAGGAGTCATTAACTTCCTCCCTCTATGCCCACCCCTGACACTTCACCATTAATCTTAACACAGA |
| 124 | ACTTGCATTGTGCTAGGGATCTGCCCTATATCTTTGCCTCTGGTGTTTCGTTGTTGTTGTTATTGTTTGTTTGTTTCCAAAGAAGTTGGAGTTAAGGACACAATATATTTGTACCCCTAGACTGAATGGGTGAGTATTCCATATGAGGATCTGGGTAATCCTCTTTGCAACCCACATTTGGTCTTCAGAGACACTGGCATTTTGAAGAAACATATGATAT |

TABLE 7-continued

| SEQ ID NO: | SEQUENCE |
|---|---|
| | AGCTGTTTGGAAATAAATTCATCTATGTTACTTTTTTTTCTTTTTTTTTTTTTTT<br>ATGAGCAGGAGATCTTAATTGACAGAAACTCATTGGTGGTTGGAGTGGCCAATG<br>GGCACGGGAAAAAGTATCCAGTAATCAGAAGAATTGTATCTGGGTTATGTAATC<br>TTATGCACATTCCATTGTCTTTGCCAAGCCCAGAAGCCATGTTGTGTTCATTGTT<br>AAGAAATTTGATAGATTTACCCAGCTTTTCTATGTATTTTGACTTATTGAAAATA<br>TGTAACAACTGAGTCGGGTTGCAGCACTGGTGGGGTAGAATCGACTTTCCCTGA<br>AGGTGACACAGATGTCAGAATTGTGTCCAGGGATTTAATTTAGACCCATACTGT<br>CCAGGAGACTGTCTCTAGTTGGATCTCTGTGCTGACTGACTGACAGACAGACTT<br>TAGTGTCTGTGTGCTGACTGACAGACTCTAGTAGTGTCTATATGTTGACCAACTG<br>GTAGACCAGGAGGATCTGTGTGCTGATTGACTCTAGTAGGATCTGTTTGTCACT<br>GACAGACTGTAGTAGTGTCTGTGTGCTGACTGATAGATAGACTATAGTAAAATT<br>TGGGTGTTGCCTGACTAACGGTCTA |
| 125 | TGATGAGTGATGGATCCACTAGGGTG |
| 126 | TAAACATTGCCTGATTTGTTCCTTC |
| 127 | CTTTAGACGGGGAGAAACATCTGGAAGGATGCTCGAGAGAACAAATGGAGGTG<br>GTGAAAATCAAGCTTTGGATTGTGCATTCCTAGGCACAAAATTACCTCATTCTTC<br>CTAACAAGCAATCTGGGACCTGATTTTCCACCTTTTTTCTCTTTTCTTCCCTTCCT<br>TTGTTTTCATAAGCCTTTGGTATCTTTCCTGCCCTTTTCCTTTGTGTACTCTATAC<br>TGGAGTTCCCTTCTTCCTCTTGCTGTAGGCTCAATCCCATACCGACATCTA |
| 128 | GCCTGGGGACGACATGGCAGGCTGGTCCCCCT |
| 129 | GGGCCTCCCGTTGTCATGCCTTACGGTTTCCAATGCGCCGTCACCATCTCCACCT<br>GCCACCAAACCACCAGCAGAGTAGCCGCCGC |
| 130 | CCAGCCATGCACCTGCGTCAACGCGCCTGA |
| 131 | GAGCAGAGGAAGCCCCAATTTCGCCCTCCGGTCACA |
| 132 | GTTCTGAAGAATGTACCCAGGTGCCTTTTTGCTAATTTGATACTATAATAGAATG<br>AGACATAAAATGAATTAATGGAAACATATCCACACTGTACTGTGATATAGGTAC<br>TCTGATTTAAAACTTTGGACATCCTGTGATCTGTTTTAAAGTTGGGGGGTGGGA<br>AATTTAGCTGACTAGGGACAAACATGTAAACCTATTTTCCTATGAAAAAAATTT<br>TAAATGTCCCACTTGAATAACGTAATTCTTCATAGTTTTTTTAATCTATGGATAA<br>ATGGAAACCTAATTATTTGTAATGAATTATTTAGACAGTTCTAAGCCCTGTCTTC<br>TGGGAGTTATCAATTTTAAAGAGAACTTTTGTGCAATTCAAATGAAGTTTTTATA<br>AGTAATTGAAAATGACAACACAATAACACTTTCTGTATAAAAGTATATATTTTA<br>TGTGATTTATTCCTACTAAATGAAAGTGCACTACTGCCTCATGTAAAGACTCTTG<br>CACGCAGAGCCTTTAAGTGACTA |
| 133 | CTGTCATCTGATTGCGGTGGTGAAATGGAATTGAGGCCCAAGGTTAGAAGCAGC<br>CGAGACGCCACTTGGATACTGATTTGAACAATGTAGAAGTCAGATTCTGAATTC<br>CAAAGTTATTTCTCATAAGTACCCAATGGCATCTCTCCATCTACAAAGTTGCAGT<br>A |
| 134 | GCAGGGCCACTACTTCTCAGCACATCCGGCCTTCTGGCTCATCTCCTCCCTGCAT<br>CTCACTACGCCCCTCC |
| 135 | TTTCTTTGCCCAGCCAGATAAGCAGGACTTTATGGGGCAAAGCCTATGTCAGCT<br>CTCTCCAAGGGCACTGGGAATTTTCCTGAGGTGTAATCGCTTCTCACTGTATG |
| 136 | GCGGACGCTGCCACCTGATCCCATCCAGGCGCTGAGAGGCAAGCCACCGGCAC<br>TCGGCGCGCAGGGCCCCGGGCACCCTCGGACCCCGTGCGGATTTCGAGACAAG<br>GGTCCAGAGATAGCGGCGGC |
| 137 | TCTTAGCGTCACTGGTCTGGCTTTCAGAATTAACATACAAGGTTGCCACACCTA<br>GTTCTGCCCAGCTTTATGTCTTTTATTCCAGTATTCCACCAAAGTTTGTTTTCCTG<br>CATTCCAGTTCTCAAGTCTTAAGATAAAGATTGTACTTGACAGTTTAGTATATCC<br>ATAAAACTATTTGAGGTGGTTAAGGTTCTTGGGTTCATTTTCCTTAATACTTTGC<br>TGAATATTGTAGATTGTAGGCAATGAAAAAGTCTACTAAATTAGGAAAACCTTG<br>AATAATTAGGTATCCTAGGTAAGAGCCCCTAAACATCAAGCAATCTGTGAGTCT<br>GTAAAGAAATAAATATTTTTTGGATTATTCTTATCTAATTCCACCCCTGTTGGAA<br>GATGATTTCTTGTTCTTTGCAACTATGGAAGCTGTGA |
| 138 | TGCGTGTATCTAATTCAGCTGATGCTCAAGTCCAAGGGGTAGTCTGCCTTCCCA<br>GGCTGCCCCCAGGGTTTCTGCACTGGTCCCCTCTTTTCCCTTCAGTCTTCTTCACT<br>TCCCTATGCTGCTGCTTCATGTGCTACATCTCAGACTTAAAGAGTTTCTCTACTA<br>CAGTGAAAACATTCTCTAGGGTCTTTCATCAGGCCTTTAGTTA |
| 139 | AGTGTCGTTCTACAATGCCCGTTGACTTATTCCATTGCGTCTCTGCTTTAGGGTA<br>TGGTTTGGTCGCTTTGGTTGTCATGAGAAAGAGACATTCTCCTTGCAGCTACCTC<br>CATGTGAGTGAATTCCTGGATAAAGCAAGATTTCCTTTCAATAAACGCTGTCAC<br>CCAATGG |

TABLE 7-continued

| SEQ ID NO: | SEQUENCE |
|---|---|
| 140 | TTTCTCCCAGATGTAAACAGAGAGA |
| 141 | TGGGTGGACGTGGTTGGTGATTGGCAGGATCCTG |
| 142 | AGTCTCCTTGGCCTATAATGAAACCACTAGGACTTTATACAGTTTTCCTTAATTT<br>GTTGACATATAAATGGTAAATTATATTTAGGCTTATCCTGTTTTGAAATGATGGT<br>AGTCATCTTTCTTACTGCTACTTTCATGTTGCTTTCTAGAAAACAGCATTTCATTC<br>CAAAATAACTAGGATCTGCATTTAGAACAAGAATCATTATTTGTCCTGACCTTTT<br>CAGTCCTACAGAGACGCATCTGTGGTTCTTTTGTACTTGCCATAGATGTAACCTA<br>AAAAGTTTTGGCATATTTAGGTCAGCCTAGCGGAACTTTTTTTTTCATTTAAATG<br>GAGCTGAATAATGGAGATTTTGTGTCTGCAAAATTCCTGAGATCATTGAAAAAG<br>TAACAAGCTGTTCCTTGTTTCTGATACATAAAATTATTTTAAGCATTTTATCAAT<br>CATTAAAATTTACTGCCAGTTGTGAGTGGCTTTTTAATTAACTTGTCTTTCATTG<br>CACTTCACTCTGCCTGTTTTCAAGGGGAGTAAGATTGGTAACATTTGGGGAGAC<br>TGTATCTGTCTACTTAGCGTGGCTGTTTTGAGGGACTGTCCCATCAGTGAACAAA<br>CTGCATGGCCTTGGAGAGAGACTCTGGGCTCTTGGCTCAGATGTGTTCATCAAA<br>TACTCCTTTCAGAGCTGTTGTGGGTGTAAGTGACATGATGTGGCCAAAAATCCA<br>AACTGTGCAGTTGCGTTGTGACAAACA |
| 143 | GATCGCTGGAGCTTAACCTTGAGGTCAAG |
| 144 | CTCCTCTTGCCATGTGAAAGAGATCAAACTTTCTCCTTAATTTATGGGAGGAGC<br>GAGCATAGAGAAGTCTGTGATGTCTCACAAGGTTCTCACTTTTACAATTGAATA<br>TAGAAGTAGCTCTTAGGAGAAGCAGAACGTTCAGAGGGGAAGATGAATATGGT<br>TTTGGGTACATTGCCTTAAATTGCATTTTTGGTATTTGGGTGGCGATGTCTAGTA<br>AGTAAA |
| 145 | AGGTCATTCCTAACACGCCGCAGCAGGGCTCTGTACAGTCCGGCCCGGTGGGGA<br>GGAGGGAGGGAAGGCAGGCACACGAAGACACAGGTATGTCGGGAAGTGCACA<br>CAAACCGTTGTCTTTCCTTTTTGGTTAAAGAAGAAAAACTTTGTAATCAATATCC<br>TGCTCATAAGTAAAAGTGGAAAAGAAGAAACTTGATTGCTTTCATCTGGCGTTT<br>TGGCATCTCCTCTCCCATTTCATATGCACAGTTTATTTGGGTAATGCTACCGTCA<br>CCAGC |
| 146 | TGAAGACATCACATTCACTATTAGCATGGAGTAAAACATTTATTTTCAAATGTC<br>ATAGAAACAATATTTATAAGTCCTCTTCTCCACCTCTTGTGTGGTGATTTACTGA<br>TTTCTCTCTTTCTTTCCTTCTTTTTCTTCAGCTTGCTTCCCATCCAGTCATCCTTTT<br>TCACAAACATTCCCTGGGGCATCTTGCTGTCTTCTGCAGAGAAACTGAAAAAAA<br>AGTAGGAACATTCCCAGCTGTG |
| 147 | AAAATTTTAAGTACGTGGCCAGCTGTTGGTTGTCTTGTGGTCATTAAAGACAAT<br>GTTAAGAATCAGGAGTACTTAAGTGCTAGTGGTTACAAATTTTGTTCTCTTCAGT<br>TTTTCATTAAGTAAATTCTAATAGATGATATACATATTACTGCAGATAAAACCAT<br>CATCAGAAATTATTAAATTAATTGCATATTTTGAGCTACTCTTTATGGAAAGAA<br>GTAAAATATTTAATACTTGTAAGGCAGCAGAGAGTTGGTTTAGAAACTCTCAGC<br>TATTTCTATAAAAATAGAATGGTTAGTAAAAATAGCATTCAGTGTATTTTCCTTA<br>GGGAGGCTATTTATAATGAAATCTGTGACTCAGCAGCAGCTGGCAATGCTGTCC<br>CTTCAAGA |
| 148 | CTCGCTTTCAGAGGCACTTGTGATGATTTTCACAGCTTCCATAGTTGCAAAGAA<br>CAAAGAAATCATCTTCCAACAGGGGTGGAATTAGATAAGAATAATCCAAAAAA<br>TATTTATTTCTTTACAGACTCACAGATTGCTTGATGTTTAGGGGCTCTTACCTAG<br>GATACCTAATTATTCAAGGTTTTCCTAATTTAGTAGACTTTTTCATTGCCTACAA<br>TCTACAATATTCAGCAAAGTATTAAGGAAAATGAACCCAAGAACCITAACCACC<br>TCAAATAGTTTTATGGATATACTAAACTGTCAAGTACAATCTTTATCTTAAGACT<br>TGAGAACTGGAATGCAGGAAAACAAACTTTGGTGGAATACTGGAATAAAAGAC<br>ATAAAGCTGGGCAGAACTAGGTGTGGCAACCTTGTATGTTAATTCTGAAAGCCA<br>GACCAGTGACGCTAAGAATAACAAATAGATTCAGATTTGTTTTTCAGAAACTTG<br>AGCTATTTCGGCCAGGTGCAC |
| 149 | AGGGTGTGTCTACAACCTGTCTAGAGGAGACTGTCTAGTCTCCTCTGCACTCAA<br>TCAGAAGGTCTGAA |
| 150 | CCTGTGGTACATGTGACTTGTTCGAGGTAGAAATGTCTCAGCTAGATCCCAAG<br>TTGTGGGGTGAAAAGTGTGAACAGAAATGGCTGTAAAACTACTTGCCTTGCAAA<br>GTCAAGTACATTTAAAAGAGGCAGAACTTGGATGTGCTTCTTTTTTCATCATGC<br>TTGTCAGTTTACGGGGTGAGAGAGGAGAAGCTTACAGCAGCTGAGGTGTTCAG<br>ATAAACTAGTTCTGGCCTCGCAGTTTTTGCTGTGCAAAAGATACACACATTGTTG<br>GGGTTAAAGGCTTGGTTTTGGGTGCTACTGCTAAA |
| 151 | TCCCTGGAAAACTGTTAGGGCCAGCCAGGTCCTTGCCGGCTGAGTTCCAGGCAT<br>TGAGAATGTGTGAGTCAGAGCCTCACCCCCGCCCCCGCGGCTGGCTGACTCACT<br>CCCTCCCTCCAGCTCAGGGGAGTCAGTCGGGGATCACTGCCTCTCCAAACCATT<br>TAAAGTTAAAGATTCTTTTATTAATAAATTCTCCCTCCCCTCCAAACTCTCCCCA |

TABLE 7-continued

| SEQ ID NO: | SEQUENCE |
|---|---|
|  | AAATAAATATCTCCTCCCCGCTTTGGGGAGTTGGGGGGGTCTGTATCTTAGGGC CAGCCCTC |
| 152 | ATGGGGGCCTAATTCCCTGTCTGGAGC |
| 153 | TGTGACATCATCACCGTCTGTGTGATGCCATCGCCGCGTCTGTGTGACATTAATA TGTGTGACGTCGAC |

What is claimed is:

1. A method comprising:
   (a) obtaining a sample from a subject with thyroid, leukemia, breast, pancreatic, prostate or lung cancer;
   (b) detecting the expression level in the sample for a plurality of targets, wherein:
      (i) the plurality of targets comprises at least two targets comprising a sequence selected from the group consisting of SEQ ID NOs: 53, 58, 76, 83, 102, 110, 117, 124, 145 and 152;
      (ii) the plurality of targets comprises at least two targets comprises a sequence that is a complement of a sequence selected from the group consisting of SEQ ID NOs: 53, 58, 76, 83, 102, 110, 117, 124, 145 and 152;
      (iii) the plurality of targets comprises at least two targets comprises a sequence that is a reverse complement of a sequence selected from the group consisting of SEQ ID NOs: 53, 58, 76, 83, 102, 110, 117, 124, 145 and 152; or
      a combination of (i-iii); and
   (c) administering a chemotherapeutic agent or radiation treatment to the subject.

2. A method of determining a treatment for a thyroid, leukemia, breast, pancreatic, prostate or lung cancer in a subject, comprising:
   (a) obtaining a sample from a subject having thyroid, leukemia, breast, pancreatic, prostate or lung cancer;
   (b) detecting the expression level in the sample from the subject for a plurality of targets, wherein:
      (i) the plurality of targets comprises at least two targets comprising a sequence selected from the group consisting of SEQ ID NOs: 53, 58, 76, 83, 102, 110, 117, 124, 145 and 152;
      (ii) the plurality of targets comprises at least two targets comprises a sequence that is a complement of a sequence selected from the group consisting of SEQ ID NOs: 53, 58, 76, 83, 102, 110, 117, 124, 145 and 152;
      (iii) the plurality of targets comprises at least two targets comprises a sequence that is a reverse complement of a sequence selected from the group consisting of SEQ ID NOs: 53, 58, 76, 83, 102, 110, 117, 124, 145 and 152; or
      a combination of (i-iii); and
   (c) administering a chemotherapeutic agent or radiation treatment to the subject.

3. The method of any of claims 1-2, wherein the plurality of targets comprises a nucleic acid sequence.

4. The method of claim 3, wherein the nucleic acid sequence is a DNA sequence.

5. The method of claim 3, wherein the nucleic acid sequence is an RNA sequence.

6. The method of any of claims 1-2 further comprising assaying an expression level of a miRNA.

7. The method of any of claims 1-2, further comprising assaying an expression level of a siRNA.

8. The method of any of claims 1-2 further comprising assaying an expression level of a snoRNA.

9. The method of any of claims 1-2 further comprising assaying an expression level of a lincRNA.

10. The method of claim 1 or 2, wherein the expression level of the plurality of targets is determined by nucleic acid hybridization or nucleic acid amplification.

11. A method, comprising:
    (a) assaying by sequencing, array hybridization or nucleic acid amplification the expression level of at least two targets in a fine needle aspirate thyroid, leukemia, breast, pancreatic, prostate or lung sample from a subject, wherein the at least two targets is selected from the group consisting of comprising a sequence selected from the group consisting of SEQ ID NOs: 53, 58, 76, 83, 102, 110, 117, 124, 145 and 152;
    (b) in a programmed computer classify said thyroid, leukemia, breast, pancreatic, prostate or lung sample as malignant if there is an increase in an expression level of the at least two targets relative to the expression of the at least two targets in a control sample; and
    (c) administering a chemotherapeutic agent or radiation treatment to the subject.

* * * * *

SEQUENCE LISTING

<160> NUMBER OF SEQ ID NOS: 153

<210> SEQ ID NO 1
<211> LENGTH: 116
<212> TYPE: DNA
<213> ORGANISM: Homo sapiens

<400> SEQUENCE: 1

```
aactgagccc aattaccaag tcctgattcg catccttatc tctcgatgtg agactgacct      60
tctgagtatc agagctgagt tcaggaagaa atttgggaag tccctctact cttctc        116
```

<210> SEQ ID NO 2
<211> LENGTH: 301
<212> TYPE: DNA
<213> ORGANISM: Homo sapiens

<400> SEQUENCE: 2

```
ttggactgtc agaacaaccg gattcgagag gtgatggatt ataccttcat cggggtcttc      60
aaactcatct accttgacct cagctccaac aacctaacct cgatctcccc attcactttc     120
tcggtgctca gcaacctggt gcagctgaac attgccaaca accctcacct gttatcgctt     180
cacaagttca cctttgccaa caccacctct ttgaggtacc tggacctcag aaataccggc     240
ttgcagaccc tggacagtgc tgccttatac cacctcacta ctctggagac cctgtttctg     300
a                                                                     301
```

<210> SEQ ID NO 3
<211> LENGTH: 31
<212> TYPE: DNA
<213> ORGANISM: Homo sapiens

<400> SEQUENCE: 3

```
ttctttgtgg aatccgtctg tgatgatcct g                                     31
```

<210> SEQ ID NO 4
<211> LENGTH: 101
<212> TYPE: DNA
<213> ORGANISM: Homo sapiens

<400> SEQUENCE: 4

```
ccctgactat cctgaaagga acagagagaa cgtgatggag gacttcctga agagaattga      60
atgctacaaa gttacctacc gacctcttga cccagacaac t                         101
```

<210> SEQ ID NO 5
<211> LENGTH: 127
<212> TYPE: DNA
<213> ORGANISM: Homo sapiens -continued

```
<400> SEQUENCE: 5
atcaaggtga taaacgtggg ccagcgattt ttagtcaaca gagtccagga ctacatccag      60
agcaagatag tctactacct catgaatatc cacgtccagc ctcgcaccat ttacctttgc     120
cggcatg                                                               127

<210> SEQ ID NO 6
<211> LENGTH: 86
<212> TYPE: DNA
<213> ORGANISM: Homo sapiens

<400> SEQUENCE: 6
aggaaataac agacctcaaa gtgtggacaa gccagttgaa gaggaccata cagactgctg      60
aatctctcgg ggtgccctat gagcag                                           86

<210> SEQ ID NO 7
<211> LENGTH: 81
<212> TYPE: DNA
<213> ORGANISM: Homo sapiens

<400> SEQUENCE: 7
tgcagagatt gagaaacggt acccagaaga gtttgcactt cgagatcaag agaagtatct      60
gtatcgatat cctggtgggg a                                                81

<210> SEQ ID NO 8
<211> LENGTH: 50
<212> TYPE: DNA
<213> ORGANISM: Homo sapiens

<400> SEQUENCE: 8
caattaaact taacgtggag gctgtgaaca cgcaccgtga caagccaact                 50

<210> SEQ ID NO 9
<211> LENGTH: 58
<212> TYPE: DNA
<213> ORGANISM: Homo sapiens

<400> SEQUENCE: 9
tgcaaccacc actccatcag gctctcctcg gacctctcaa caaaacgttt ataatcct        58

<210> SEQ ID NO 10
<211> LENGTH: 102
<212> TYPE: DNA
<213> ORGANISM: Homo sapiens

<400> SEQUENCE: 10
ccgaagggag ccgatcggaa acagaagact gaccgggaga agatggagaa aagaactgcc      60
caagagaagg agaaatacca gccgtcctat gaaaccacca tc                        102

<210> SEQ ID NO 11
<211> LENGTH: 227
<212> TYPE: DNA
<213> ORGANISM: Homo sapiens

<400> SEQUENCE: 11
cttagaacag cgaaacttga ctttggaaac agaaatgatg agcctccatg atgaactgga      60
tcaggagagg aaaaagttca caatgataga aataaaaatg cgaaatgccg agcgagcaaa    120
agaagatgcc gagaaaagaa atgacatgct acagaaagaa atggagcagt ttttttccac    180
gtttggagaa ctgacagtgg aacccaggag aaccgagaga ggaaaca                  227
```

<210> SEQ ID NO 12
<211> LENGTH: 32
<212> TYPE: DNA
<213> ORGANISM: Homo sapiens

<400> SEQUENCE: 12
aaatccccag agaacgtatg gaacgaaaaa ga                           32

<210> SEQ ID NO 13
<211> LENGTH: 68
<212> TYPE: DNA
<213> ORGANISM: Homo sapiens

<400> SEQUENCE: 13
gactagccca ggccgagtgg acctcccagg atcaagcacc actcttacaa agtctttcac    60
tagctctt                                                             68

<210> SEQ ID NO 14
<211> LENGTH: 82
<212> TYPE: DNA
<213> ORGANISM: Homo sapiens

<400> SEQUENCE: 14
gaatagcaga gcaaaccgtt gtaacactaa gaaacccaaa tgcggtttta actttagtgg    60
atgacaacct tgcaccagaa ta                                             82

<210> SEQ ID NO 15
<211> LENGTH: 167
<212> TYPE: DNA
<213> ORGANISM: Homo sapiens

<400> SEQUENCE: 15
gctgctttga ctctcccgcg aagacctttc cttcactgtt ctactgtgat tcccgttgtg    60
gttctgaccc tgaaatttac tatgcacctt ttcaagctca aagactcatg gtgctttctt   120
ccctggatgt tatttatatc ctggacttca catcatatcc gagatgg                 167

<210> SEQ ID NO 16
<211> LENGTH: 138
<212> TYPE: DNA
<213> ORGANISM: Homo sapiens

<400> SEQUENCE: 16
tgtcttcgtt ttcatggccc ttctggaata tgccctagtc aactacatct tctttgggag    60
ggggccccaa cgccaaaaga aagcagctga aaggctgcc agtgccaaca atgagaagat    120
gcgcctggat gtcaacaa                                                 138

<210> SEQ ID NO 17
<211> LENGTH: 147
<212> TYPE: DNA
<213> ORGANISM: Homo sapiens

<400> SEQUENCE: 17
tatcccaggt tatccctcag ctttaagctt aagagaaaca ttggctactt tatcctgcaa    60
acatacatgc cttccatcct gattaccatc ctctcctggg tctccttctg gattaattac   120
gatgcttcag ctgcaagggt ggcatta                                       147

<210> SEQ ID NO 18

```
<211> LENGTH: 71
<212> TYPE: DNA
<213> ORGANISM: Homo sapiens

<400> SEQUENCE: 18
actgtccagt gccagaacga cggccgctcc tgctggtgtg tgggtgccaa cggcagtgaa      60
gtgctgggca g                                                          71

<210> SEQ ID NO 19
<211> LENGTH: 92
<212> TYPE: DNA
<213> ORGANISM: Homo sapiens

<400> SEQUENCE: 19
ggctacatta acagcacaga cacctcctac ctccctcagt gtcaggattc aggggactac      60
gcgcctgttc agtgtgatgt gcagcaggtc ca                                    92

<210> SEQ ID NO 20
<211> LENGTH: 303
<212> TYPE: DNA
<213> ORGANISM: Homo sapiens

<400> SEQUENCE: 20
cctctccaag agtagccaga tttgccacat cctgcccacc cacgatcaag gagctctttg      60
tggactctgg gcttctccgc caatggtgg agggacagag ccaacagttt tctgtctcag      120
aaaatcttct caaagaagcc atccgagcaa ttttttccctc ccgagggctg gctcgtcttg    180
cccttcagtt taccaccaac ccaaagagac tccagcaaaa ccttttttgga gggaaatttt   240 tggtgaatgt tggccagttt aacttgtctg agcccttgg cacaagaggc acatttaact      300
tca                                                                   303

<210> SEQ ID NO 21
<211> LENGTH: 77
<212> TYPE: DNA
<213> ORGANISM: Homo sapiens

<400> SEQUENCE: 21
gcactgctgg tgtgtagatg agaaaggagg gttcatccct ggctcactga ctgcccgctc      60
tctgcagatt ccacagt                                                    77

<210> SEQ ID NO 22
<211> LENGTH: 155
<212> TYPE: DNA
<213> ORGANISM: Homo sapiens

<400> SEQUENCE: 22
agcactcttt ctgtcagctc gcagagataa cagagagtgc atccttgtac ttcacctgca      60
ccctctaccc agaggcacag gtgtgtgatg acatcatgga gtccaatgcc cagggctgca    120
gactgatcct gcctcagatg ccaaaggccc tgttc                                155

<210> SEQ ID NO 23
<211> LENGTH: 147
<212> TYPE: DNA
<213> ORGANISM: Homo sapiens

<400> SEQUENCE: 23
tctgacctgg gtgcagaccc acatccgagg atttggcggg gaccctcggc gcgtgtccct      60
ggcagcagac cgtggcgggg ctgatgtggc cagcatccac cttctcacgg ccagggccac    120
```

```
caactcccaa cttttccgga gagctgt                                      147
```

\<210\> SEQ ID NO 24
\<211\> LENGTH: 92
\<212\> TYPE: DNA
\<213\> ORGANISM: Homo sapiens

\<400\> SEQUENCE: 24

```
ttctacccag cctacgaggg gcagttttct ctggaggaga agagcctgtc gctgaaaatc    60
atgcagtact tttcccactt catcagatca gg                                  92
```

\<210\> SEQ ID NO 25
\<211\> LENGTH: 95
\<212\> TYPE: DNA
\<213\> ORGANISM: Homo sapiens

\<400\> SEQUENCE: 25

```
tgagcccgca ccggggacac ctggggacca agaacctctg tgtggaggtg gccgacctgg    60
tcagcatcct ggtgcatgcc gacacaccac tgcct                               95
```

\<210\> SEQ ID NO 26
\<211\> LENGTH: 99
\<212\> TYPE: DNA
\<213\> ORGANISM: Homo sapiens

\<400\> SEQUENCE: 26

```
actggatagc gacttccttg ccgtgctaag tgactacccg tctcctgaca tcagcccccc    60
gatattccgc cgaggggaga aactgcgtgt gatttctga                           99
```

\<210\> SEQ ID NO 27
\<211\> LENGTH: 56
\<212\> TYPE: DNA
\<213\> ORGANISM: Homo sapiens

\<400\> SEQUENCE: 27

```
tagcttaagt gatggcagcg atagtgaaag cagttctgct tcttcacccc tacatc        56
```

\<210\> SEQ ID NO 28
\<211\> LENGTH: 80
\<212\> TYPE: DNA
\<213\> ORGANISM: Homo sapiens

\<400\> SEQUENCE: 28

```
cctcctggag tagtgaatat tgttcctggt tatgggccta cagcaggggc agccatttct    60
tctcacatgg atatagacaa                                                80
```

\<210\> SEQ ID NO 29
\<211\> LENGTH: 51
\<212\> TYPE: DNA
\<213\> ORGANISM: Homo sapiens

\<400\> SEQUENCE: 29

```
ccgctggtcc gcgagccctg ccgcagctgt gccgtggtgt ccagctccgg c              51
```

\<210\> SEQ ID NO 30
\<211\> LENGTH: 333
\<212\> TYPE: DNA
\<213\> ORGANISM: Homo sapiens

\<400\> SEQUENCE: 30

```
ccctccctgt gtgaaatgta ttatcaccag cagacactgc cgggcctccc tcccgggggc    60
actgcctgaa ggcgagtgtg ggcatagcat tagctgcttc ctcccctcct ggcacccact   120
gtggcctggc atcgcatcgt ggtgtgtcaa tgccacaaaa tcgtgtgtcc gtggaaccag   180
tcctagccgc gtgtgacagt cttgcattct gtttgtctcg tggggggagg tggacagtcc   240
tgcggaaatg tgtcttgtct ccatttggat aaaaggaacc aaccaacaaa caatgccatc   300
actggaattt cccaccgctt tgtgagccgt gtc                                333
```

<210> SEQ ID NO 31
<211> LENGTH: 33
<212> TYPE: DNA
<213> ORGANISM: Homo sapiens

<400> SEQUENCE: 31

```
gaatgcagac gggtcaggcg ctgtgaactt cct                                 33
```

<210> SEQ ID NO 32
<211> LENGTH: 29
<212> TYPE: DNA
<213> ORGANISM: Homo sapiens

<400> SEQUENCE: 32

```
ctctggagga gtttttgaaa gccacagaa                                      29
```

<210> SEQ ID NO 33
<211> LENGTH: 51
<212> TYPE: DNA
<213> ORGANISM: Homo sapiens

<400> SEQUENCE: 33

```
aaagaacaat cgacaggaca gaagcggcct ttgaagaacg acgaactata a             51
```

<210> SEQ ID NO 34
<211> LENGTH: 29
<212> TYPE: DNA
<213> ORGANISM: Homo sapiens

<400> SEQUENCE: 34

```
tgagcctttg gagttaggag gtcctggag                                      29
```

<210> SEQ ID NO 35
<211> LENGTH: 68
<212> TYPE: DNA
<213> ORGANISM: Homo sapiens

<400> SEQUENCE: 35

```
ctgttttttc gggtagagga gcgcaagaag tggcccgaac ggctgtctgc cctcgataat    60
ctcctcaa                                                             68
```

<210> SEQ ID NO 36
<211> LENGTH: 84
<212> TYPE: DNA
<213> ORGANISM: Homo sapiens

<400> SEQUENCE: 36

```
gtgattttca tgatgctggg cggcactttt ctctactggc gtgggcgccg gattcagaat    60
aaaagggcta tgaggcgata cttg                                           84
```

<210> SEQ ID NO 37
<211> LENGTH: 27

```
<212> TYPE: DNA
<213> ORGANISM: Homo sapiens

<400> SEQUENCE: 37
gatggaaaag ttaagcacaa tggtcag                                           27

<210> SEQ ID NO 38
<211> LENGTH: 43
<212> TYPE: DNA
<213> ORGANISM: Homo sapiens

<400> SEQUENCE: 38
ttagaacttc gatttaacaa atgtgttcgt ctctgtggaa cag                         43

<210> SEQ ID NO 39
<211> LENGTH: 84
<212> TYPE: DNA
<213> ORGANISM: Homo sapiens

<400> SEQUENCE: 39
gatgtcatcc ggaaacctca aggccaagtg gatctgaact cccgctgcca aattgttcga       60
ggggagggtt cacagacgtt tcag                                              84

<210> SEQ ID NO 40
<211> LENGTH: 140
<212> TYPE: DNA
<213> ORGANISM: Homo sapiens

<400> SEQUENCE: 40
tggccagcta tatgaaccat tgcactacaa ctgtgaaccc ccccaccaac ccacccggag       60
cctgccagct gtgggaactg gatggacgac agttcttttc ttctgtttcc tgtgctacca     120
aggggccaac gttgctgtga                                                  140

<210> SEQ ID NO 41
<211> LENGTH: 136
<212> TYPE: DNA
<213> ORGANISM: Homo sapiens

<400> SEQUENCE: 41
caactgcaac ttggcctctt gatccaccaa aggatgagaa acaagggtgg agacatgtga       60
gaattaaaca gatggggaaa aatgccagtg gacaaacaca ctacctctca ttatctggat     120
tcgaacttta tggcac                                                     136

<210> SEQ ID NO 42
<211> LENGTH: 66
<212> TYPE: DNA
<213> ORGANISM: Homo sapiens

<400> SEQUENCE: 42
actaaaatgt tgatgggcga agtgatgaga gaagctgcct tttcactagc tgaagccaag       60
ttcaca                                                                  66

<210> SEQ ID NO 43
<211> LENGTH: 117
<212> TYPE: DNA
<213> ORGANISM: Homo sapiens

<400> SEQUENCE: 43
ctgagtcaga ctacccagga gcagaagcag ttgtctgaga agctcaaaga ggagagtgag       60
```
cagaaggagc agctaagaag gttgaagaac gagatggaga atgagcggtg gcacctg 117

<210> SEQ ID NO 44
<211> LENGTH: 38
<212> TYPE: DNA
<213> ORGANISM: Homo sapiens

<400> SEQUENCE: 44
agagaagcag gatatgcgtt gggtagagca gctggagt 38

<210> SEQ ID NO 45
<211> LENGTH: 182
<212> TYPE: DNA
<213> ORGANISM: Homo sapiens

<400> SEQUENCE: 45
gtagatgcca gtctcacaat agacacagca aaattgtttc tgtcttgcct tttgccatgg 60
ggagtggata aagatttaga ttatctttgc attaagcacc tcaatatttt aaagcttcag 120
ggtcctattt ctttgggaat ttctttgaat gaagataatt tctcactgat gttgccaggt 180
tg 182

<210> SEQ ID NO 46
<211> LENGTH: 59
<212> TYPE: DNA
<213> ORGANISM: Homo sapiens

<400> SEQUENCE: 46
ttgacttccg agagtatgtg attggcctgg ctgtcttgtg caacccttcc aacacagag 59

<210> SEQ ID NO 47
<211> LENGTH: 30
<212> TYPE: DNA
<213> ORGANISM: Homo sapiens

<400> SEQUENCE: 47
gccgctccga gggcgtttgg ggtcaggctg 30

<210> SEQ ID NO 48
<211> LENGTH: 60
<212> TYPE: DNA
<213> ORGANISM: Homo sapiens

<400> SEQUENCE: 48
aggtgtggat gtaagcgaag tcaaagaagt atacctcgac ctggttaaga aaggcgttca 60

<210> SEQ ID NO 49
<211> LENGTH: 112
<212> TYPE: DNA
<213> ORGANISM: Homo sapiens

<400> SEQUENCE: 49
tgctatggca ccttagtgga acacatgatg gagccgcgac ccctcagcac tgcacccaag 60
attagtgacg acacaccact ggaaatgatg acatcgcctc gagccagctg ga 112

<210> SEQ ID NO 50
<211> LENGTH: 116
<212> TYPE: DNA
<213> ORGANISM: Homo sapiens

<400> SEQUENCE: 50
tgaggagggg ctggatgacc aaagcattgt aacagggctg gaagccaagg aagacctcta 60
tcttgaaccc caagttggcc atgaccccgc cggccctgct gcctcgcctg tcctgg    116

<210> SEQ ID NO 51
<211> LENGTH: 30
<212> TYPE: DNA
<213> ORGANISM: Homo sapiens

<400> SEQUENCE: 51
aatcatacaa tgacccaaca cagcagttag    30

<210> SEQ ID NO 52
<211> LENGTH: 67
<212> TYPE: DNA
<213> ORGANISM: Homo sapiens

<400> SEQUENCE: 52
acttcctcat caccaacgat gaggcatacg ctgaggagtt tggcaacgag acgtggggcg    60
taacaaa    67

<210> SEQ ID NO 53
<211> LENGTH: 27
<212> TYPE: DNA
<213> ORGANISM: Homo sapiens

<400> SEQUENCE: 53
gtcccacaac cgcagcgagg agtttct    27

<210> SEQ ID NO 54
<211> LENGTH: 323
<212> TYPE: DNA
<213> ORGANISM: Homo sapiens

<400> SEQUENCE: 54
gtaaaggtaa caactccagg ctctgaacag gcattcccgtt agctgagttc acaaaatacc    60
ataaaagtga tgcataacct ttatcttgta caaaataatg agaatttggc cactactata    120
taagaaatat ctatttaaaa tcatagtgta cagaactccc ctataaagaa aacacgtgga    180
gtgcttaatt ccttcctttg ttagacacat ttaatagaca gagaattacc ataatgtaca    240
tacacttcaa tggatacaat cagaaagcag gcagactgtc agcttacaga ccctagaccg    300
ttagtcaggc aacacccaaa ttt    323

<210> SEQ ID NO 55
<211> LENGTH: 87
<212> TYPE: DNA
<213> ORGANISM: Homo sapiens

<400> SEQUENCE: 55
aagtggcttg ttactgccaa ctcacactgg catagcaatt ttaaatgtct tccatatatc    60
taaaacagca gtcacaatcg cagaaac    87

<210> SEQ ID NO 56
<211> LENGTH: 238
<212> TYPE: DNA
<213> ORGANISM: Homo sapiens

<400> SEQUENCE: 56
gcgagagtta tgtcaaagat ttacctgcaa agatttagct aaaagaacaa cttggaaaac    60
acatataaat gaaacacata tgaatgaaga cccccctagcc acattcatcc ttgtagttag    120

```
gactggaatt ctagccatag tcacatcccc agtccctggc ccagatcgaa cctctaatat    180
aattattacc caccaagaaa ataagatcgt attctgtttc agtactcaga gacggttc     238
```

<210> SEQ ID NO 57
<211> LENGTH: 315
<212> TYPE: DNA
<213> ORGANISM: Homo sapiens

<400> SEQUENCE: 57

```
tgacacaccg gcagacattc acatctcttc catagtacat cccccggctg cacagactct    60
tcagatctgt tagcttgaac agggacccat agtatgtggc cagtgcaggg tcatctctct   120
gaatgagaag gggcttctgc tcccagaatt ccttgaaaaa agtctctgtc ttgatgggcg   180
agattaaact ttcaaagaga ctactgggac tgtcaaagtt taaagctgaa ggccccccag   240
ctgcttctaa cttcatctgc ttacagggag ccggcccctc ttccttccca ctccctgtag   300
gctttgcttt ctttg                                                   315
```

<210> SEQ ID NO 58
<211> LENGTH: 84
<212> TYPE: DNA
<213> ORGANISM: Homo sapiens

<400> SEQUENCE: 58

```
tgttaaggaa atgatacagg cttcctatat cttttccctt aaaaacgact ctatggactt    60
aagttcaccg aaggaagtgg aatg                                          84
```

<210> SEQ ID NO 59
<211> LENGTH: 256
<212> TYPE: DNA
<213> ORGANISM: Homo sapiens

<400> SEQUENCE: 59

```
actgcggcat tcctttaggc tgacaagggg ttttggtgaa ataaaatgtt ttcaattgtt    60
tctcaatagt cattgtcttg gttttggcat aggtttaaaa tatccgtgtg tgctctgatg   120
gattgtccag tgggaattta cttcttataa aaggaaaaga gaaagacaga ctgactcagg   180
ggacaaatag gtggtgactc agattgactg tctgatcaga gaagggagtg aaaatggctt   240
gggacctttt ctggag                                                  256
```

<210> SEQ ID NO 60
<211> LENGTH: 95
<212> TYPE: DNA
<213> ORGANISM: Homo sapiens

<400> SEQUENCE: 60

```
tctgatacca ttttcggggc aaagaacttg gctaactttg caaggtaaac tccattccgg    60
agcccttctt ccaattcagt ggttggtggc aattc                              95
```

<210> SEQ ID NO 61
<211> LENGTH: 58
<212> TYPE: DNA
<213> ORGANISM: Homo sapiens

<400> SEQUENCE: 61

```
atgcagcttc atccacggac agttcattgg ccagaatacc acctatttg ctgaaaga      58
```

<210> SEQ ID NO 62
<211> LENGTH: 83

<212> TYPE: DNA
<213> ORGANISM: Homo sapiens

<400> SEQUENCE: 62

```
gctagaaagc acgagactgc atttctcaaa ctccttgtgg agtttcacac actgaccgca      60
caccctgtta tgggcgatgg agg                                              83
```

<210> SEQ ID NO 63
<211> LENGTH: 60
<212> TYPE: DNA
<213> ORGANISM: Homo sapiens

<400> SEQUENCE: 63

```
attttcagcg acaggctctt ctcctccaga gaaaactgcc cctcgtaggc tgggtagaag      60
```

<210> SEQ ID NO 64
<211> LENGTH: 194
<212> TYPE: DNA
<213> ORGANISM: Homo sapiens

<400> SEQUENCE: 64

```
gacggaagtc tctacagcaa ggctaagggc tcgccagacg gcgaacatca ggggtgcatg      60
gtgggcactg cccaggcaat aagttaggaa gcagcagggc tggtgtcggg tgtgggccgg     120
gcttcatttc tgggcaggca tgaggtcgtc gatggcctgg ccctgctcca gccgctgctc     180
catctcgatg agca                                                       194
```

<210> SEQ ID NO 65
<211> LENGTH: 1394
<212> TYPE: DNA
<213> ORGANISM: Homo sapiens

<400> SEQUENCE: 65

```
gcgctaccta aatgccactg ggagagacct cctgcaaagt tttctttagc ccctctttta      60
tcccacaata cacaagatat aatccatttt tatatatccc aaagttgtgg caacagcttc     120
tttcttttct gctcaatgcc actttgtttc ctagtaattc atgaccacta ttaattctat     180
cattgtcact gctcctgctt aagatacact ctcaaggata cctcagtaag caatggataa     240 atcaacttt tgttatatgt gccaagtact aagtttcagg gttctcttca gcaatcatta     300
attaatactt cagccattaa ttcagatgca ataattttc ttttttcttt ttttttgagat     360 ggagtttcac tcttgttgcc caggctggag tgcaatggcg tgatctcagc tcaccgcaac     420
ctccgcctcc caggttcaag cgattctcct gcctcagccc cctagtagc tgggattaca     480 ggcatgcgcc accacaccca gctaattttg tattttagt agagacgggg tttctccgtg     540
ttggtcaggc tggtctcgaa ctcctgacct caggtgatcc gcctgcctcg gcctcccaaa     600
gtgctgggat tacaggcatg agccaccaca cccagccaga tgcaaataat tttcttagaa     660
aattatttca aaagttattt taggcccaga atcaaggat tgttccaacc atgaaaatgg     720
gtaagacacc tgccttaagc aaatctaacc tgctattact tgccaaattt tatatattct     780
tttctcttgc ctgtatttct aattagtgat ttgtttaatg aagaactctt catgtagagc     840
aattaactgg gcctaagaaa tttcgaagct ttccatgaca taaagtggtt aaaaaaaaat     900
gctttgacag tcttcttctg ccattagttc aactgccttt acgctttttt tttttttttt     960
ttttttgaga tggagtttca ctcttgttgc ccaggctaga gtgcaatggc gtgatcttgg    1020
ctcactgcaa cctctgcctc ccgggttcaa gcaattctcc tgcctcagcc tcctgagtag    1080
```

| | |
|---|---|
| ctgggatttc aggcatacgc caccatgcct ggctaatttt gtattttag tagagacagg | 1140 |
| gtttctccat gttggtcagg ctggtctcga actcccgacc tcaggtgatc tgcctgcctt | 1200 |
| ggcctcccaa agtgctggga ttacaggtgt gagccaccac ccccagccgc ctctatgctt | 1260 |
| tttgtttctt tgatatatct aaacttaagg tcagaacaga aattcatgtg ctgaacagaa | 1320 |
| tggattcttt ttgcagtacc aatccaattg aatcctcttt ttattttcct gcgtccttac | 1380 |
| cagtcacttt gata | 1394 |

<210> SEQ ID NO 66
<211> LENGTH: 36
<212> TYPE: DNA
<213> ORGANISM: Homo sapiens

<400> SEQUENCE: 66

| | |
|---|---|
| aaaagcagcc agacatagtg atacacacct gcagtc | 36 |

<210> SEQ ID NO 67
<211> LENGTH: 32
<212> TYPE: DNA
<213> ORGANISM: Homo sapiens

<400> SEQUENCE: 67

| | |
|---|---|
| atgtggtaag aattgcacac ctcaaatcta cc | 32 |

<210> SEQ ID NO 68
<211> LENGTH: 192
<212> TYPE: DNA
<213> ORGANISM: Homo sapiens

<400> SEQUENCE: 68

| | |
|---|---|
| gactaagagg ggaataaaag caagaagaaa aagaaacgta agaacaccag taaaggaaag | 60 |
| acagggaccg agacaggtgg ttaagggaaa tgaaaaaaaa aaaaaaaagg tgaaagtcaa | 120 |
| tccaaacaaa gaaaaatggc acttccaacc aaaaaaaatg aaggtgtaga accctgtcat | 180 |
| caattgctca ga | 192 |

<210> SEQ ID NO 69
<211> LENGTH: 35
<212> TYPE: DNA
<213> ORGANISM: Homo sapiens

<400> SEQUENCE: 69

| | |
|---|---|
| aagattgtca cttttggtgg atctgcaaaa aaagt | 35 |

<210> SEQ ID NO 70
<211> LENGTH: 615
<212> TYPE: DNA
<213> ORGANISM: Homo sapiens

<400> SEQUENCE: 70

| | |
|---|---|
| tctgcaggta gtagatgatg gttccatctc ggcattgtct atcctctcca tattcagact | 60 |
| gtgtgactga gcttccttga tttatatagc atctgaccca aaatcacaaa aaagtcactc | 120 |
| ctgatgacat ttgcatgggg agtctttcat ttggacttca gttcttaatt gccgaaataa | 180 |
| gtactagtga attatgtagc gttttaccc aaaactaatc ttctgtacaa agttgtgtgc | 240 |
| atattgagat gattagttaa ggcagtgtag ttttttaaat ttttctgta taaatttctt | 300 |
| tccttcttcc ccacctcagg cacctaccct actcctttca gagcacttta tatccctctt | 360 |
| gaaatacaaa gaaattgaaa aaaaaaaaaa agtaactgtc tttaaaggaa tttgtcttct | 420 |

```
attaggagac acagactttt attttgcttt attctattct ctttgtactt ggagagcgta    480
atcaacttgt ctcataatgg gctagtgatg aaacaagggt gatagttgga aacagtcatt    540
acaacatggt tattttgtt atatagaaga ctatcatgta aataagtgca atcgtgttct     600
tacgtactgg ctaaa                                                     615

<210> SEQ ID NO 71
<211> LENGTH: 43
<212> TYPE: DNA
<213> ORGANISM: Homo sapiens

<400> SEQUENCE: 71
cacgtgacga cccaggacac atgcgcaccc gacgcagccc agg                       43

<210> SEQ ID NO 72
<211> LENGTH: 27
<212> TYPE: DNA
<213> ORGANISM: Homo sapiens

<400> SEQUENCE: 72
gctcaggcag cacctgaccc tagccag                                         27

<210> SEQ ID NO 73
<211> LENGTH: 324
<212> TYPE: DNA
<213> ORGANISM: Homo sapiens

<400> SEQUENCE: 73
ccagggtaat tatgcagtgt caccactact cacagggatt atggcctgag aaactaaaat    60
gatacttctt aggtgaccag aggatgggag aacttcttaa ctggtttgga ggtccacata   120
aagaataatt ggggtctaga attaaggaag gaaaagcaat acaaagaaat ggagcagggc   180
tatagcagtg aaccaattgg ttggtaagtg aaacctgtaa gatgcctaat tgagtaattt   240
aatgactaat tttattaggc taaacagaac agaaaccatg ctaatctgta acaaataagt   300
ggcgccagcc tattacagtg aatg                                          324

<210> SEQ ID NO 74
<211> LENGTH: 63
<212> TYPE: DNA
<213> ORGANISM: Homo sapiens

<400> SEQUENCE: 74 atagggctg ctgtagaatg ccttccttgc atagtgactg tccgtgattc cattattctc     60
aaa                                                                  63

<210> SEQ ID NO 75
<211> LENGTH: 62
<212> TYPE: DNA
<213> ORGANISM: Homo sapiens

<400> SEQUENCE: 75
ctcaaagaaa ctagtgatgg cagagcccct taagcaagga cgtagaatgg atgttcaaaa    60
ag                                                                   62

<210> SEQ ID NO 76
<211> LENGTH: 41
<212> TYPE: DNA
<213> ORGANISM: Homo sapiens
```

<400> SEQUENCE: 76
gtgtgagaac aaaaagctgt gttggggcca agcctctgtg t        41

<210> SEQ ID NO 77
<211> LENGTH: 25
<212> TYPE: DNA
<213> ORGANISM: Homo sapiens

<400> SEQUENCE: 77
tttatacgtg tctgaataaa aatgc        25

<210> SEQ ID NO 78
<211> LENGTH: 260
<212> TYPE: DNA
<213> ORGANISM: Homo sapiens

<400> SEQUENCE: 78
tctagtggcc gcaagggca tcccagaatg tgatgccact gggtgcacag acagcctccc        60
acattaccaa gggcatgctc ccggggccct aacctaagac cccagaagaa cgggtcgctg        120
ccaccaagaa gtataaatat gtgtgtggaa gactacgagc cttattcgaa tgacggcatg        180
gggtatgggg actacctgaa gctccctgac cacttatagc agaagaggga tctgtggtat        240
aactgagacc acctggcctg        260

<210> SEQ ID NO 79
<211> LENGTH: 199
<212> TYPE: DNA
<213> ORGANISM: Homo sapiens

<400> SEQUENCE: 79
ctggtctgag ccaatttagt ccttcaatga ttgtattagc tgccatggga cgtgagaggt        60
gagaggaggc cattcgtctt cttttctgta atctcctgca ggtgggatat taaaaatagt        120
taaggccaaa ttctgccaaa tatacatgta ttggcaagct ggcacaaaac agtcacacag        180
cctgcttcaa gaaaatggg        199

<210> SEQ ID NO 80
<211> LENGTH: 98
<212> TYPE: DNA
<213> ORGANISM: Homo sapiens

<400> SEQUENCE: 80
ctctctgtct atatacacac ctgcatgcat atatacatat atatatgtat gcatctatat        60
atttatatct aatctcgtat tgcttattgg ttctgttt        98

<210> SEQ ID NO 81
<211> LENGTH: 47
<212> TYPE: DNA
<213> ORGANISM: Homo sapiens

<400> SEQUENCE: 81
cttcatgata caggatgttg tatgtatgtg gaaccatcct cactcac        47

<210> SEQ ID NO 82
<211> LENGTH: 30
<212> TYPE: DNA
<213> ORGANISM: Homo sapiens

<400> SEQUENCE: 82
ccctgcgctt gcagatgagc acctgacctg        30

<210> SEQ ID NO 83
<211> LENGTH: 150
<212> TYPE: DNA
<213> ORGANISM: Homo sapiens

<400> SEQUENCE: 83
tcggtgctca cccagtatga ggatcatacg aattggtggt tggaaaagca ttgaaatgtc    60
actgactttg actgtcagat gtgtggggtc aggcaggcat gtgtttctcg gatgctcatt   120
gtagctcttg cttatccatt tttattaact                                    150

<210> SEQ ID NO 84
<211> LENGTH: 61
<212> TYPE: DNA
<213> ORGANISM: Homo sapiens

<400> SEQUENCE: 84
gttggcctat gtcagtctct gctggtgtct ggatgaagat ggacaagggg ccaccactct    60
c                                                                    61

<210> SEQ ID NO 85
<211> LENGTH: 44
<212> TYPE: DNA
<213> ORGANISM: Homo sapiens

<400> SEQUENCE: 85
aaagataatg gacaacagtg ccgtgactcc catgtattgt ctca                     44

<210> SEQ ID NO 86
<211> LENGTH: 25
<212> TYPE: DNA
<213> ORGANISM: Homo sapiens

<400> SEQUENCE: 86
ggagattgga aacatgcacg cacac                                          25

<210> SEQ ID NO 87
<211> LENGTH: 94
<212> TYPE: DNA
<213> ORGANISM: Homo sapiens

<400> SEQUENCE: 87
ttcctgcgag cctgcatcag tacacgctgc tgcccactct gtctcctcat gttttggaag    60
gcatgaggaa gacaggccga cacactgctt gtga                                94

<210> SEQ ID NO 88
<211> LENGTH: 36
<212> TYPE: DNA
<213> ORGANISM: Homo sapiens

<400> SEQUENCE: 88
tcacgacatt gtaaacccaa gcccgagagt cactat                              36

<210> SEQ ID NO 89
<211> LENGTH: 68
<212> TYPE: DNA
<213> ORGANISM: Homo sapiens

<400> SEQUENCE: 89
ttctggattc ctagagagaa gggtaatact atgttactca gaacacatcc agtatatcag    60

```
catgcttt                                                                    68

<210> SEQ ID NO 90
<211> LENGTH: 128
<212> TYPE: DNA
<213> ORGANISM: Homo sapiens

<400> SEQUENCE: 90
ctggaagaat gtctccaagc tgctgttagt gtttatttga agtgactttg aaggactgat     60
aatattatgg ggcaggcaga ctctcactat cttaaggtgg ttcgcctgag ccttcttaaa    120
gtggtacc                                                              128

<210> SEQ ID NO 91
<211> LENGTH: 31
<212> TYPE: DNA
<213> ORGANISM: Homo sapiens

<400> SEQUENCE: 91
ttgggtagga cagggccaa ctcacacagt g                                      31

<210> SEQ ID NO 92
<211> LENGTH: 155
<212> TYPE: DNA
<213> ORGANISM: Homo sapiens

<400> SEQUENCE: 92
cccatgactg ttcatgacta tcccaaagct ggatgttgtc tgtctctggg ccctgtgtgc     60
tcgcatgcgc gtgtgtggtg tgtgtgtgcg tgtgtgtgtg tgtgtgcgca cgtgcacgca    120
tttaccaaat gcaggtgtgt cctcctactc agaag                                155

<210> SEQ ID NO 93
<211> LENGTH: 47
<212> TYPE: DNA
<213> ORGANISM: Homo sapiens

<400> SEQUENCE: 93
gctgtaggtc gatcacacag ggccaagaca tgtttctcca atatctc                    47

<210> SEQ ID NO 94
<211> LENGTH: 334
<212> TYPE: DNA
<213> ORGANISM: Homo sapiens

<400> SEQUENCE: 94
tggctggctg agaatacagg gtaaagaact gtccagtgtt gtgagtggtg ccttagagtt     60
gctcatagca agaaaatcac tgggagggt ggaagtggct ctcagatggt cattggttac    120
ctataactta tttaaagaag accttgagaa gttgggacat atcttgtcac tgaggaaatt    180
gtgccaaaga actgctgctt tattaacgca tttgatcaga tttgaaaaga gagctctgta    240
tacactcttt ttctaactcc aaagaaattt tgtttctaga aagattcaat taccgtaatg    300
atgttctttg gaaatgtgcc ttttttgcgtg tata                                334

<210> SEQ ID NO 95
<211> LENGTH: 39
<212> TYPE: DNA
<213> ORGANISM: Homo sapiens

<400> SEQUENCE: 95
gggagctcat tacacctgcc tcactttggt tagctgaag                             39
```

<210> SEQ ID NO 96
<211> LENGTH: 320
<212> TYPE: DNA
<213> ORGANISM: Homo sapiens

<400> SEQUENCE: 96

```
gaaaactagg ctcaacagat aagaaaataa gcaccctgct ttcccctgta gtcgttccag      60
tgaggcctct gcagcctcct gggtggcttt ggagccctga acacctgggc acaaatcttg     120
gcttccttcc ttccatgtga gggtcctgta aaagtcgctt cacctcctgg agttacatta    180
tcctcatctg tcaagtgtcg gaagctggaa gttggcaaag aaatgcaaag cacattggaa    240
atggaaaaga aagaaggagg catccattga taaacactaa gttacttctt catgtccaga    300
ggactctaca tgccacatgc                                                320
```

<210> SEQ ID NO 97
<211> LENGTH: 48
<212> TYPE: DNA
<213> ORGANISM: Homo sapiens

<400> SEQUENCE: 97

```
ggtggcttca ctagaacctg gacggggcag tagggcactg gatgagaa                  48
```

<210> SEQ ID NO 98
<211> LENGTH: 67
<212> TYPE: DNA
<213> ORGANISM: Homo sapiens

<400> SEQUENCE: 98

```
cacaggatcc gagaaataca cacctgtagt taggaaaaag aactcagtag tggtgcgtgg      60
aatgaat                                                               67
```

<210> SEQ ID NO 99
<211> LENGTH: 203
<212> TYPE: DNA
<213> ORGANISM: Homo sapiens

<400> SEQUENCE: 99

```
gctcctctta aacatttgta gtttgccttt aatattttaa attattttat aattagtata      60
tatggacaac ttatagaaat ctggtttatg ttttggagga aactgtgatt ggatatgggt    120
tgctgatggt cgcataagaa tgttgaacag tattgtaggc tgccattgag gtattctaaa    180
tacctgatgt gctttagaga aga                                            203
```

<210> SEQ ID NO 100
<211> LENGTH: 325
<212> TYPE: DNA
<213> ORGANISM: Homo sapiens

<400> SEQUENCE: 100

```
ccgtgtagtt gtaggaagca tcttcactaa tgcaacacca gacagccata ttatgaagaa      60
attaagtgga aattagcgga aatgtccatt catttgctgt attatttgta tgtaatattt    120
gggttgatct ataaacactg tcagactaaa gttttttaaaa tatacttatt ctatttatt    180
tcagcattta tgaatttaca acattggtaa gtgatatggg attttaaaat tgcaaatgtt    240
cattattcat atcattgaat acatgttgag cacacccaca ttgtataggt tgtggtaatt    300
agcttgtaac tagggtatta tctgt                                          325
```

<210> SEQ ID NO 101
<211> LENGTH: 29
<212> TYPE: DNA
<213> ORGANISM: Homo sapiens

<400> SEQUENCE: 101
agtttgtttt gaggtcaggt gctgtggct                              29

<210> SEQ ID NO 102
<211> LENGTH: 57
<212> TYPE: DNA
<213> ORGANISM: Homo sapiens

<400> SEQUENCE: 102
tgtcctagtg caggcagatg tggccaccct cacctctcgc agggtgctgc atgcctg    57

<210> SEQ ID NO 103
<211> LENGTH: 27
<212> TYPE: DNA
<213> ORGANISM: Homo sapiens

<400> SEQUENCE: 103
actatctgaa aatgggcagg tggtgca                                27

<210> SEQ ID NO 104
<211> LENGTH: 62
<212> TYPE: DNA
<213> ORGANISM: Homo sapiens

<400> SEQUENCE: 104
atggcaatct tgagggcagg tgaaggcagg gagaaccaga aatggttgcc agctcttatc    60
tt                                                                  62

<210> SEQ ID NO 105
<211> LENGTH: 68
<212> TYPE: DNA
<213> ORGANISM: Homo sapiens

<400> SEQUENCE: 105
aaatgcaggt gcaatgtgtg tgagcaagtg tgtttgaaag tgtatgtatt tgagaccaag    60
tgcagtgg                                                            68

<210> SEQ ID NO 106
<211> LENGTH: 69
<212> TYPE: DNA
<213> ORGANISM: Homo sapiens

<400> SEQUENCE: 106
tgtcactgct gactgtgtat gtatgctgct gccttgaaac acagtatgtt ggacttattc    60
attcacctt                                                           69

<210> SEQ ID NO 107
<211> LENGTH: 60
<212> TYPE: DNA
<213> ORGANISM: Homo sapiens

<400> SEQUENCE: 107
gtgatcaaca agttcacgcc aagccccaac agcccagcgc taaggaaggc cacagtgtcc    60

<210> SEQ ID NO 108
<211> LENGTH: 91

```
<212> TYPE: DNA
<213> ORGANISM: Homo sapiens

<400> SEQUENCE: 108
tccagggcaa caagggacaa gatgaaaaag ctttcaggga caggcagtgg gcacctgtgg      60
gaccccgctt ccattacagc atgacactct g                                    91

<210> SEQ ID NO 109
<211> LENGTH: 68
<212> TYPE: DNA
<213> ORGANISM: Homo sapiens

<400> SEQUENCE: 109
ccccactgcc ctgagacttt tcctaatggc ccctctcagc agcctgggca gcctccttga      60
atttctgc                                                              68

<210> SEQ ID NO 110
<211> LENGTH: 66
<212> TYPE: DNA
<213> ORGANISM: Homo sapiens

<400> SEQUENCE: 110
gttctgtaag atcaccgtcc tgaccccag gagcacactc acccatgggg tcaggctgct       60
attaga                                                                66

<210> SEQ ID NO 111
<211> LENGTH: 30
<212> TYPE: DNA
<213> ORGANISM: Homo sapiens

<400> SEQUENCE: 111
gctgccttcc tgaagctcgc acacctgcct                                      30

<210> SEQ ID NO 112
<211> LENGTH: 71
<212> TYPE: DNA
<213> ORGANISM: Homo sapiens

<400> SEQUENCE: 112
ggagtgagaa tctggagggt caagaggaag gggaaggcac tgcagatatg ggacagcaga      60
ataagacatg g                                                          71

<210> SEQ ID NO 113
<211> LENGTH: 26
<212> TYPE: DNA
<213> ORGANISM: Homo sapiens

<400> SEQUENCE: 113
ttcatgaagc tcagcggcac acactc                                          26

<210> SEQ ID NO 114
<211> LENGTH: 255
<212> TYPE: DNA
<213> ORGANISM: Homo sapiens

<400> SEQUENCE: 114
gtgccgatac cctggggata atataatcaa actaaccgtc tctgcgcagc ctggataaaa      60
ccatgcaaaa cgaaaggtat cagcttgttt tcaaacatca caaaaccatt ctgaagaagc     120
aaaccaggtt ggatgagtcc aatgactgat atgtgttcct atgacttctc ctacacctgc     180
```

```
ttcctggcgt gcccatcctg ggacactggc gagtctgctc actgacactg gcacgggcct      240
gtctgtacag tcaca                                                       255

<210> SEQ ID NO 115
<211> LENGTH: 508
<212> TYPE: DNA
<213> ORGANISM: Homo sapiens

<400> SEQUENCE: 115
acctgcagta cacgcttgac tatgactaag ccatggatca gaggtctaat taagcctgat      60
tgccagagca atgagaggat gtttcagaca tcatattttt gttgtttaga ctgctttatt     120
tttaactttc cagggcatt aaaaaaaaaa aagaggaaa aagatgcaac catccacctg        180
agtaaagata atatatataa gtaattgttc tttaagggca atgagcgagc cgtattgtat     240
aatgttctcc tttcatcact gtttcgttca ttgctcgtgt ggaattagag tggttgattt     300
gggggaatct gggggttttg tttttgttat tgttgttttg tatgttccta gcacatttta     360
ggggacagtg ttgaggattc cttactaagc tgactgtctt ttgctgggta catctgctgg     420
caggtttctc taacgtgaca atgtgatact tcgggtcagt ttctgtggct cccctctccc     480
cctcgttacg cttgcacttg acattttg                                        508

<210> SEQ ID NO 116
<211> LENGTH: 26
<212> TYPE: DNA
<213> ORGANISM: Homo sapiens

<400> SEQUENCE: 116
gttaagaatg tctgagggt caggcg                                            26

<210> SEQ ID NO 117
<211> LENGTH: 117
<212> TYPE: DNA
<213> ORGANISM: Homo sapiens

<400> SEQUENCE: 117
aggcgatctg aggacccgac ataaccgaaa cgtcttggat gctggacagt ctataactgg      60
cacatgccag ggagacaagc aatgacaaag ctcaaacact aaaggtggga ccatcac        117

<210> SEQ ID NO 118
<211> LENGTH: 132
<212> TYPE: DNA
<213> ORGANISM: Homo sapiens

<400> SEQUENCE: 118
caagttttcg atgtgtctct ttttcccgta aagtggctga aatctgaagc tgaatctgca      60
agtgtcatgg agtcattgaa tctcacagtc tcaactgata aaagttatta aaggtcgtct    120
ggttcagcct tc                                                         132

<210> SEQ ID NO 119
<211> LENGTH: 154
<212> TYPE: DNA
<213> ORGANISM: Homo sapiens

<400> SEQUENCE: 119
gagagtgggt ggattcattg ccacactctt ttctcccagg gacccaggaa actaggactt      60
tgtgtgtttg ctgcccacct ccctttatt ttttaaatgc attaaaaact gtgctagtct     120
cctttgcatg gacttcaagc tgcatgaaat gcaa                                 154
```

<210> SEQ ID NO 120
<211> LENGTH: 91
<212> TYPE: DNA
<213> ORGANISM: Homo sapiens

<400> SEQUENCE: 120
tgcctcttgt atgttgatgc cacttcttgg aagaagatga gggcaatgag ttagggctcc     60 ttttccccctt ccctcccacc agattgctct c                                    91

<210> SEQ ID NO 121
<211> LENGTH: 26
<212> TYPE: DNA
<213> ORGANISM: Homo sapiens

<400> SEQUENCE: 121
caaatattcg gtccttgtga cttcca                                           26

<210> SEQ ID NO 122
<211> LENGTH: 244
<212> TYPE: DNA
<213> ORGANISM: Homo sapiens

<400> SEQUENCE: 122
tcctcaacct agaaatacgt aatcaagcaa actatcaatc aagtgtgagg gtagaatatg     60
agagacgtga atactgatgg ggatgtgata tgcagcaggc actgttctaa atggtttaca    120
tgtaccaacc caattaagaa acttaaaata cacacgtgca cacacacaca cacacacaca    180
cacacacaca cacacacaca cagttttttcc tgctaatcat tttacgatga aacagccaag    240
tagc                                                                  244

<210> SEQ ID NO 123
<211> LENGTH: 135
<212> TYPE: DNA
<213> ORGANISM: Homo sapiens

<400> SEQUENCE: 123
gtcagcattc cggtggtgta actgtgtgtt tccctccagc cctggcctcc tgcccttgtc     60
actaatcacc aaggagtcat taacttcctc cctctatgcc caccctgac acttcaccat    120 taatcttaac acaga                                                     135

<210> SEQ ID NO 124
<211> LENGTH: 845
<212> TYPE: DNA
<213> ORGANISM: Homo sapiens

<400> SEQUENCE: 124
acttgcattg tgctagggat ctgccctata tctttgcctc tggtgtttcg ttgttgttgt     60
tattgtttgt ttgttttccaa agaagttgga gttaaggaca caatatatttt gtaccctag    120 actgaatggg tgagtattcc atatgaggat ctgggtaatc ctctttgcaa cccacatttg    180
gtcttcagag acactggcat tttgaagaaa catatgatat agctgtttgg aaataaattc    240
atctatgtta cttttttttt cttttttttt tttttttatg agcaggagat cttaattgac    300
agaaactcat tggtggttgg agtggccaat gggcacggga aaaagtatcc agtaatcaga    360
agaattgtat ctgggttatg taatcttatg cacattccat tgtctttgcc aagcccagaa    420
gccatgttgt gttcattgtt aagaaatttg atagatttac ccagcttttc tatgtatttt    480

```
gacttattga aaatatgtaa caactgagtc gggttgcagc actggtgggg tagaatcgac      540
tttccctgaa ggtgacacag atgtcagaat tgtgtccagg gatttaattt agacccatac      600
tgtccaggag actgtctcta gttggatctc tgtgctgact gactgacaga cagactttag      660
tgtctgtgtg ctgactgaca gactctagta gtgtctatat gttgaccaac tggtagacca      720
ggaggatctg tgtgctgatt gactctagta ggatctgttt gtcactgaca gactgtagta      780
gtgtctgtgt gctgactgat agatagacta tagtaaaatt gggtgttgc ctgactaacg       840 gtcta                                                                   845
```

<210> SEQ ID NO 125
<211> LENGTH: 26
<212> TYPE: DNA
<213> ORGANISM: Homo sapiens

<400> SEQUENCE: 125

```
tgatgagtga tggatccact agggtg                                            26
```

<210> SEQ ID NO 126
<211> LENGTH: 25
<212> TYPE: DNA
<213> ORGANISM: Homo sapiens

<400> SEQUENCE: 126

```
taaacattgc ctgatttgtt ccttc                                             25
```

<210> SEQ ID NO 127
<211> LENGTH: 271
<212> TYPE: DNA
<213> ORGANISM: Homo sapiens

<400> SEQUENCE: 127

```
ctttagacgg ggagaaacat ctggaaggat gctcgagaga acaaatggag gtggtgaaaa      60
tcaagctttg gattgtgcat tcctaggcac aaaattacct cattcttcct aacaagcaat      120
ctgggacctg attttccacc tttttttctct tttcttccct tcctttgttt tcataagcct     180
ttggtatctt tcctgccctt ttcctttgtg tactctatac tggagttccc ttcttcctct     240
tgctgtaggc tcaatcccat accgacatct a                                     271
```

<210> SEQ ID NO 128
<211> LENGTH: 32
<212> TYPE: DNA
<213> ORGANISM: Homo sapiens

<400> SEQUENCE: 128

```
gcctggggac gacatggcag gctggtcccc ct                                     32
```

<210> SEQ ID NO 129
<211> LENGTH: 86
<212> TYPE: DNA
<213> ORGANISM: Homo sapiens

<400> SEQUENCE: 129

```
gggcctcccg ttgtcatgcc ttacggtttc caatgcgccg tcaccatctc cacctgccac      60
caaaccacca gcagagtagc cgccgc                                            86
```

<210> SEQ ID NO 130
<211> LENGTH: 30
<212> TYPE: DNA
<213> ORGANISM: Homo sapiens

```
<400> SEQUENCE: 130
ccagccatgc acctgcgtca acgcgcctga                                  30

<210> SEQ ID NO 131
<211> LENGTH: 36
<212> TYPE: DNA
<213> ORGANISM: Homo sapiens

<400> SEQUENCE: 131
gagcagagga agccccaatt tcgccctccg gtcaca                           36

<210> SEQ ID NO 132
<211> LENGTH: 514
<212> TYPE: DNA
<213> ORGANISM: Homo sapiens

<400> SEQUENCE: 132
gttctgaaga atgtacccag gtgcctttt gctaatttga tactataata gaatgagaca  60
taaaatgaat taatggaaac atatccacac tgtactgtga tataggtact ctgatttaaa 120
actttggaca tcctgtgatc tgttttaaag ttgggggtg ggaaatttag ctgactaggg  180
acaaacatgt aaacctattt tcctatgaaa aaaattttaa atgtcccact tgaataacgt 240
aattcttcat agttttttta atctatggat aaatggaaac ctaattattt gtaatgaatt 300
atttagacag ttctaagccc tgtcttctgg gagttatcaa ttttaaagag aacttttgtg 360
caattcaaat gaagttttta taagtaattg aaaatgacaa cacaataaca ctttctgtat 420
aaaagtatat attttatgtg atttattcct actaaatgaa agtgcactac tgcctcatgt 480
aaagactctt gcacgcagag cctttaagtg acta                            514

<210> SEQ ID NO 133
<211> LENGTH: 164
<212> TYPE: DNA
<213> ORGANISM: Homo sapiens

<400> SEQUENCE: 133
ctgtcatctg attgcggtgg tgaaatggaa ttgaggccca aggttagaag cagccgagac  60
gccacttgga tactgatttg aacaatgtag aagtcagatt ctgaattcca aagttatttc  120
tcataagtac ccaatggcat ctctccatct acaaagttgc agta                  164

<210> SEQ ID NO 134
<211> LENGTH: 71
<212> TYPE: DNA
<213> ORGANISM: Homo sapiens

<400> SEQUENCE: 134
gcagggccac tacttctcag cacatccggc cttctggctc atctcctccc tgcatctcac  60
tacgcccctc c                                                      71

<210> SEQ ID NO 135
<211> LENGTH: 107
<212> TYPE: DNA
<213> ORGANISM: Homo sapiens

<400> SEQUENCE: 135
tttctttgcc cagccagata agcaggactt tatggggcaa agcctatgtc agctctctcc  60
aagggcactg ggaattttcc tgaggtgtaa tcgcttctca ctgtatg               107
```

```
<210> SEQ ID NO 136
<211> LENGTH: 126
<212> TYPE: DNA
<213> ORGANISM: Homo sapiens

<400> SEQUENCE: 136
gcggacgctg ccacctgatc ccatccaggc gctgagaggc aagccaccgg cactcggcgc      60
gcagggcccc gggcaccctc ggaccccgtg cggatttcga gacaagggtc cagagatagc     120
ggcggc                                                                126

<210> SEQ ID NO 137
<211> LENGTH: 421
<212> TYPE: DNA
<213> ORGANISM: Homo sapiens

<400> SEQUENCE: 137
tcttagcgtc actggtctgg ctttcagaat taacatacaa ggttgccaca cctagttctg      60
cccagcttta tgtcttttat tccagtattc caccaaagtt tgtttcctg cattccagtt     120 ctcaagtctt aagataaaga ttgtacttga cagtttagta tatccataaa actatttgag    180
gtggttaagg ttcttgggtt cattttcctt aatactttgc tgaatattgt agattgtagg    240
caatgaaaaa gtctactaaa ttaggaaaac cttgaataat taggtatcct aggtaagagc    300
ccctaaacat caagcaatct gtgagtctgt aaagaaataa atattttttg gattattctt    360
atctaattcc acccctgttg aagatgatt tctttgttct ttgcaactat ggaagctgtg     420
a                                                                    421

<210> SEQ ID NO 138
<211> LENGTH: 208
<212> TYPE: DNA
<213> ORGANISM: Homo sapiens

<400> SEQUENCE: 138
tgcgtgtatc taattcagct gatgctcaag tccaaggggt agtctgcctt cccaggctgc      60
ccccagggtt tctgcactgg tcccctcttt tccottcagt cttcttcact tcccatgct     120 gctgcttcat gtgctacatc tcagacttaa agagtttctc tactacagtg aaaacattct    180
ctagggtctt tcatcaggcc tttagtta                                       208

<210> SEQ ID NO 139
<211> LENGTH: 171
<212> TYPE: DNA
<213> ORGANISM: Homo sapiens

<400> SEQUENCE: 139
agtgtcgttc tacaatgccc gttgacttat tccattgcgt ctctgcttta gggtatggtt      60
tggtcgcttt ggttgtcatg agaaagagac attctccttg cagctacctc catgtgagtg     120
aattcctgga taaagcaaga tttcctttca ataaacgctg tcacccaatg g              171

<210> SEQ ID NO 140
<211> LENGTH: 25
<212> TYPE: DNA
<213> ORGANISM: Homo sapiens

<400> SEQUENCE: 140
tttctcccag atgtaaacag agaga                                           25
```

```
<210> SEQ ID NO 141
<211> LENGTH: 34
<212> TYPE: DNA
<213> ORGANISM: Homo sapiens

<400> SEQUENCE: 141
tgggtggacg tggttggtga ttggcaggat cctg                            34

<210> SEQ ID NO 142
<211> LENGTH: 739
<212> TYPE: DNA
<213> ORGANISM: Homo sapiens

<400> SEQUENCE: 142
agtctccttg gcctataatg aaaccactag gactttatac agttttcctt aatttgttga    60
catataaatg gtaaattata tttaggctta tcctgttttg aaatgatggt agtcatcttt   120
cttactgcta ctttcatgtt gctttctaga aaacagcatt tcattccaaa ataactagga   180
tctgcattta gaacaagaat cattatttgt cctgaccttt tcagtcctac agagacgcat   240
ctgtggttct tttgtacttg ccatagatgt aacctaaaaa gttttggcat atttaggtca   300
gcctagcgga actttttttt tcatttaaat ggagctgaat aatggagatt ttgtgtctgc   360
aaaattcctg agatcattga aaaagtaaca agctgttcct tgtttctgat acataaaatt   420
attttaagca ttttatcaat cattaaaatt tactgccagt tgtgagtggc ttttttaatta  480 acttgtcttt cattgcactt cactctgcct gttttcaagg ggagtaagat tggtaacatt   540
tggggagact gtatctgtct acttagcgtg gctgttttga gggactgtcc catcagtgaa   600
caaactgcat ggccttggag agagactctg ggctcttggc tcagatgtgt tcatcaaata   660
ctcctttcag agctgttgtg ggtgtaagtg acatgatgtg gccaaaaatc caaactgtgc   720
agttgcgttg tgacaaaca                                               739

<210> SEQ ID NO 143
<211> LENGTH: 29
<212> TYPE: DNA
<213> ORGANISM: Homo sapiens

<400> SEQUENCE: 143
gatcgctgga gcttaacctt gaggtcaag                                   29

<210> SEQ ID NO 144
<211> LENGTH: 222
<212> TYPE: DNA
<213> ORGANISM: Homo sapiens

<400> SEQUENCE: 144
ctcctcttgc catgtgaaag agatcaaact ttctccttaa tttatgggag gagcgagcat    60
agagaagtct gtgatgtctc acaaggttct cacttttaca attgaatata gaagtagctc   120
ttaggagaag cagaacgttc agaggggaag atgaatatgg ttttgggtac attgccttaa   180
attgcatttt tggtatttgg gtggcgatgt ctagtaagta aa                     222

<210> SEQ ID NO 145
<211> LENGTH: 275
<212> TYPE: DNA
<213> ORGANISM: Homo sapiens

<400> SEQUENCE: 145
aggtcattcc taacacgccg cagcagggct ctgtacagtc cggcccggtg gggaggaggg    60
```

```
agggaaggca ggcacacgaa gacacaggta tgtcgggaag tgcacacaaa ccgttgtctt    120
tcctttttgg ttaaagaaga aaaactttgt aatcaatatc ctgctcataa gtaaaagtgg    180
aaaagaagaa acttgattgc tttcatctgg cgttttggca tctcctctcc catttcatat    240
gcacagttta tttgggtaat gctaccgtca ccagc                               275
```

<210> SEQ ID NO 146
<211> LENGTH: 242
<212> TYPE: DNA
<213> ORGANISM: Homo sapiens

<400> SEQUENCE: 146

```
tgaagacatc acattcacta ttagcatgga gtaaaacatt tattttcaaa tgtcatagaa     60
acaatattta taagtcctct tctccacctc ttgtgtggtg attactgat ttctctcttt     120 ctttccttct ttttcttcag cttgcttccc atccagtcat ccttttttcac aaacattccc    180 tggggcatct tgctgtcttc tgcagagaaa ctgaaaaaaa agtaggaaca ttcccagctg    240
tg                                                                   242
```

<210> SEQ ID NO 147
<211> LENGTH: 389
<212> TYPE: DNA
<213> ORGANISM: Homo sapiens

<400> SEQUENCE: 147

```
aaaatttaa gtacgtggcc agctgttggt tgtcttgtgg tcattaaaga caatgttaag      60
aatcaggagt acttaagtgc tagtggttac aaatttgtt ctcttcagtt tttcattaag     120
taaattctaa tagatgatat acatattact gcagataaaa ccatcatcag aaattattaa    180
attaattgca tattttgagc tactctttat ggaaagaagt aaaatattta atacttgtaa    240
ggcagcagag agttggtttta gaaactctca gctatttcta taaaaataga atggttagta    300
aaaatagcat tcagtgtatt ttccttaggg aggctattta taatgaaatc tgtgactcag    360
cagcagctgg caatgctgtc ccttcaaga                                      389
```

<210> SEQ ID NO 148
<211> LENGTH: 508
<212> TYPE: DNA
<213> ORGANISM: Homo sapiens

<400> SEQUENCE: 148

```
ctcgctttca gaggcacttg tgatgatttt cacagcttcc atagttgcaa agaacaaaga     60
aatcatcttc caacaggggt ggaattagat aagaataatc caaaaaatat ttatttcttt    120
acagactcac agattgcttg atgtttaggg gctcttacct aggataccta attattcaag    180
gttttcctaa tttagtagac ttttttcattg cctacaatct acaatattca gcaaagtatt    240
aaggaaaatg aacccaagaa ccttaaccac ctcaaatagt tttatggata tactaaactg    300
tcaagtacaa tctttatctt aagacttgag aactggaatg caggaaaaca aactttggtg    360
gaatactgga ataaaagaca taaagctggg cagaactagg tgtggcaacc ttgtatgtta    420
attctgaaag ccagaccagt gacgctaaga ataacaaata gattcagatt tgttttcag    480 aaacttgagc tatttcggcc aggtgcac                                       508
```

<210> SEQ ID NO 149
<211> LENGTH: 68
<212> TYPE: DNA
<213> ORGANISM: Homo sapiens

<400> SEQUENCE: 149
agggtgtgtc tacaacctgt ctagaggaga ctgtctagtc tcctctgcac tcaatcagaa    60
ggtctgaa                                                             68

<210> SEQ ID NO 150
<211> LENGTH: 306
<212> TYPE: DNA
<213> ORGANISM: Homo sapiens

<400> SEQUENCE: 150
cctgtggtac atgtgacttg ttcgaggtag aaatgtctca gctagatccc caagttgtgg    60
ggtgaaaagt gtgaacagaa atggctgtaa aactacttgc cttgcaaagt caagtacatt   120
taaaagaggc agaaacttgg atgtgcttct tttttcatca tgcttgtcag tttacggggt   180
gagagaggag aagcttacag cagctgaggt gttcagataa actagttctg gcctcgcagt   240
ttttgctgtg caaagatac acacattgtt ggggttaaag gcttggtttt gggtgctact    300
gctaaa                                                              306

<210> SEQ ID NO 151
<211> LENGTH: 279
<212> TYPE: DNA
<213> ORGANISM: Homo sapiens

<400> SEQUENCE: 151
tccctggaaa actgttaggg ccagccaggt ccttgccggc tgagttccag gcattgagaa    60
tgtgtgagtc agagcctcac ccccgccccc gcggctggct gactcactcc ctccctccag   120
ctcaggggag tcagtcgggg atcactgcct ctccaaacca tttaaagtta agattctttt   180
tattaataaa ttctccctcc cctccaaact ctccccaaaa taaatatctc ctccccgctt   240
tggggagttg gggggtctg tatcttaggg ccagccctc                           279

<210> SEQ ID NO 152
<211> LENGTH: 27
<212> TYPE: DNA
<213> ORGANISM: Homo sapiens

<400> SEQUENCE: 152
atgggggcct aattccctgt ctggagc                                        27

<210> SEQ ID NO 153
<211> LENGTH: 69
<212> TYPE: DNA
<213> ORGANISM: Homo sapiens

<400> SEQUENCE: 153
tgtgacatca tcaccgtctg tgtgatgcca tcgccgcgtc tgtgtgacat taatatgtgt    60
gacgtcgac                                                            69